US008728814B2

(12) United States Patent
Miyazaki et al.

(10) Patent No.: US 8,728,814 B2
(45) Date of Patent: May 20, 2014

(54) TECHNIQUE FOR CULTURE OF MESENCHYMAL STEM CELL UTILIZING LAMININ-5

(75) Inventors: Kaoru Miyazaki, Kanagawa (JP); Junko Hashimoto, Kanagawa (JP); Yoshinobu Kariya, Ibaraki (JP)

(73) Assignee: Oriental Yeast Co., Ltd., Tokyo (JP)

( * ) Notice: Subject to any disclaimer, the term of this patent is extended or adjusted under 35 U.S.C. 154(b) by 24 days.

(21) Appl. No.: 12/064,626

(22) PCT Filed: Aug. 17, 2006

(86) PCT No.: PCT/JP2006/316545
§ 371 (c)(1),
(2), (4) Date: Feb. 22, 2008

(87) PCT Pub. No.: WO2007/023875
PCT Pub. Date: Mar. 1, 2007

(65) Prior Publication Data
US 2009/0269848 A1 Oct. 29, 2009

(30) Foreign Application Priority Data
Aug. 23, 2005 (JP) ................................ 2005-240814

(51) Int. Cl.
*C12N 5/00* (2006.01)
*C12N 5/02* (2006.01)
*C12N 15/00* (2006.01)
*C12N 5/071* (2010.01)

(52) U.S. Cl.
CPC ............ *C12N 5/0663* (2013.01); *C12N 5/0668* (2013.01); *C12N 2501/999* (2013.01); *C12N 2533/90* (2013.01)
USPC ........................... 435/383; 435/384; 435/325

(58) Field of Classification Search
CPC .................................................... C12N 5/0663
See application file for complete search history.

(56) References Cited

U.S. PATENT DOCUMENTS

2003/0211604 A1 11/2003 Brown

FOREIGN PATENT DOCUMENTS

WO WO 00/27996 A 5/2000
WO WO0189709 11/2001

OTHER PUBLICATIONS

Masunaga, T et al, Journal of Histochemistry and Cytochemistry, 1996, 44:1223-1230.*
International Search Report for application No. PCT/JP2006/316545 mailed Dec. 5, 2006.
Klees et al., Laminin-5 Induces Osteogenic Gene Expression in Human Mesenchymal Stem Cells through an ERK-dependent Pathway, Molecular Biology of the Cell, Feb. 2005, 881-889, vol. 16.
Tsutsumi et al., Retention of Multilineage Differentiation Potential of Mesenchymal Cells During Proliferation in Response to FGF, Biochemical and Biophysical Research Communications 288, 413-419 (2001).
Mizushima, et al., Identification of Integrin-dependent and -independent Cell Adhesion Domains in COOH-Terminal Globular Region of Laminin-5 α 3 Chain, Cell growth & Differentiation, vol. 8, 979-987, Sep. 1997.
International Preliminary Report on Patentability for PCT/JP2006/316545.
Matsubara et al., A New Technique to Expand Human Mesenchymal Stem Cells Using Basement Membrane Extracellular Matrix, Bioichemical and Biophysical Research Communications 313 (2004) 503-508.
English Translation of International Preliminary Report on Patentability for PCT/JP2006/316545, mailed May 22, 2008.
Extended European search report for PCT/JP2006/316545, mailed Nov. 14, 2008.
Miyasaki, K. et al., A Large Cell-Adhesive Scatter Factor Secreted by Human Gastric Carcinoma Cells, Proc. Natl. Acad. Sci. USA 90 (1993) pp. 11767-11771.
Yoshinobu, K. et al., Characterization of Laminin 5B and NH2-terminal Proteolytic Fragment of its Alpha3B Chain—Promotion of Cellular Adhesion, Migration, and Proliferation, J. Bio Chem USA vol. 279, No. 23, 2004 pp. 24774-24784.
Matsubara T. et al., A New Technique to Expand Human Mesenchymal Stem Cells Using Basement Membrane Extracellular Matrix, Biochem & Biophysical Research Communications 313 (2004) pp. 503-508.

* cited by examiner

*Primary Examiner* — Valarie Bertoglio
(74) *Attorney, Agent, or Firm* — Bingham McCutchen LLP

(57) ABSTRACT

Disclosed is an agent for improving at least one activity selected from the group consisting of the growth activity, adhesion activity and extension activity of mesenchymal stem cells, which comprises laminin-5 as an active ingredient. A method of culturing mesenchymal stem cells; a method of isolating mesenchymal stem cells; and a medium, vessel or sheet for use in culturing mesenchymal stem cells are also provided.

13 Claims, 9 Drawing Sheets
(2 of 9 Drawing Sheet(s) Filed in Color)

Arrows indicate cleavage sites.

5A、Laminin-5A ; 5B、Laminin-5B ;
-ME、Under non-reducing conditions ; +ME、Under reducing conditions

SEQUENCE LISTING

```
<160> NUMBER OF SEQ ID NOS: 12

<210> SEQ ID NO 1
<211> LENGTH: 10002
<212> TYPE: DNA
<213> ORGANISM: Homo sapiens

<400> SEQUENCE: 1

atggcggcgg ccgcgcggcc tcggggtcgg gcactggggc cagtactgcc gccgacgccg      60

ctgctcctgc tggtactgcg ggtgctgcca gcctgcgggg cgaccgctcg ggatcccggg     120

gccgcggccg ggctcagcct tcacccgact tacttcaacc tggccgaggc ggcgaggatt     180

tgggccaccg ccacctgcgg ggagagggga cccggcgagg ggaggcccca gcccgagctc     240

tactgcaagt tggtcggggg ccccaccgcc ccaggcagcg gccacaccat ccagggccag     300

ttctgtgact attgcaattc tgaagacccc aggaaagcac atcctgtcac caatgccatc     360

gatggatctg aacgttggtg gcaaagccct cccctgtcct caggcacaca gtacaacaga     420

gtcaacctca ccttggatct ggggcagctc ttccatgtgg cctatatttt aatcaaattt     480

gcaaattctc ctcgccctga tctttgggtc ttggaaagat ctgtagactt tggaagcacc     540

tactcaccat ggcaatattt tgctcattct aaagtagact gtttaaaaga atttgggcgg     600

gaggcaaata tggctgtcac ccgggatgat gatgtacttt gtgttactga atattcccgt     660
```

-continued

```
attgtacctt tggaaaatgg tgaggttgtg gtgtccttga taaacggtcg tccaggtgca    720
aaaaatttta ctttctctca caccctgagg gagtttacca aggcaacaaa catccgcttg    780
cgttttctta gaaccaatac gcttcttgga cacctcatct ccaaagccca gcgagatcca    840
actgtcactc ggcggtatta ttacagcata aaggacatca gcattggtgg gcagtgtgtt    900
tgcaatggcc atgctgaagt gtgcaatata aacaatcctg aaaaactgtt tcggtgtgaa    960
tgccagcacc acacctgtgg ggagacgtgt gatcgctgct gcacagggta caatcagagg   1020
cgctggcggc ccgccgcttg ggagcagagc cacgagtgtg aagcatgcaa ctgccacggc   1080
catgccagca actgttacta tgatccagat gttgagcggc agcaggcaag cttgaatacc   1140
cagggcatct atgctggtgg aggggtctgc attaactgtc agcacaacac agctggagta   1200
aactgtgaac agtgtgctaa gggctattac cgcccttatg ggttccagt ggatgcccct   1260
gatggctgca tcccctgcag ctgtgaccct gagcatgcgg atggctgtga acagggttca   1320
ggccgctgtc actgcaagcc aaatttccac ggagacaact gtgagaagtg tgcaattgga   1380
tactacaatt tcccattttg cttgagaatt cccatttttc ctgtttctac accaagttca   1440
gaagatccag tagctggaga tataaaaggg tgtgactgta atctggaagg tgttctccct   1500
gaaatatgtg atgcccacgg acggtgcctg tgccgccctg ggttgaggg ccctcgatgt   1560
gatacctgcc gctctggttt ctactcattc cctatttgcc aagcctgctg gtgttcagcc   1620
cttggatcct accagatgcc ctgcagctca gtgactggac agtgtgaatg tcggccagga   1680
gttacaggac agcggtgtga caggtgtctc tcaggagctt atgatttccc ccactgccaa   1740
ggttccagca gtgcttgtga cccagctggt accatcaact ccaatttggg gtattgccaa   1800
tgcaagcttc atgttgaagg tcctacttgt agccgctgca aactgttata ttggaatctg   1860
gacaaagaaa accccagtgg atgttcagaa tgcaagtgcc ataaggcggg aacagtgagt   1920
ggaactggag agtgtaggca gggagatggt gactgtcact gcaagtccca tgtgggtggc   1980
gattcctgcg acacctgtga agatggatat tttgctttgg aaaagagcaa ttactttggg   2040
tgtcaagggt gtcagtgtga cattggtggg gcattgtcct ccatgtgcag tgggccctcg   2100
ggagtgtgcc agtgccgaga gcatgtcgtg ggaaaggtgt gccagcggcc tgaaaacaac   2160
tactatttcc cagatttgca tcatatgaag tatgagattg aagacggcag cacacctaat   2220
gggagagacc ttcgatttgg atttgatccg ctggcatttc ctgagtttag ctggagagga   2280
tatgcccaaa tgacctcagt acagaatgat gtaagaataa cattgaatgt agggaagtca   2340
agtggctcct tgtttcgtgt tattctgaga tacgttaacc ctggaactga agcagtatct   2400
ggccatataa ctatttatcc atcctggggt gctgctcaaa gcaaagagat catcttcctg   2460
ccgagtaagg agccagcctt tgtcactgtc cctggaaatg gttttgcaga cccattttca   2520
atcacaccag gaatatgggt tgcttgtatt aaggcagaag gagtccttct ggattacctg   2580
gtgctgctcc ccagggacta ctatgaagcc tctgtactgc agctgccagt cacagaacca   2640
tgtgcctacg caggacctcc ccaagaaaat tgcttactct accagcattt gccagtgacc   2700
agattcccct gtaccctggc ttgtgaggcc agacacttcc tgcttgatgg ggagccaaga   2760
cccgtggcag tgaggcagcc cacacctgca caccctgtca tggtggacct cagcgggaga   2820
gaggtggaat tgcatctgcg gctgcgcatc ccacaggttg gccactacgt ggttgtggtc   2880
gagtattcca cggaggcagc tcagctgttt gtggttgatg tgaatgtgaa gagctccggg   2940
tctgttctgg caggccaggt gaacatttac agctgcaact acagtgttct ctgccggagt   3000
gctgtgattg atcacatgag ccgcatcgcc atgtatgagc tattggcaga tgcagacatt   3060
```

-continued

```
cagctcaagg gacacatggc ccgattcctt ctgcatcaag tttgtatcat acctattgaa   3120
gaattctcag ctgagtatgt gagaccacaa gtccactgca ttgccagtta tgggcgattt   3180
gtcaatcaaa gtgccacctg tgtctccttg gcccatgaaa ctcctccaac agcattaatt   3240
ttggatgttc taagtggcag gcctttccct cacctgcccc agcagtcgtc accttctgtt   3300
gatgttcttc ctggggtcac cttgaaggca ccgcagaatc aagtgaccct gagaggacgt   3360
gtaccacacc tgggccgata cgtctttgtc atccattttt accaagcagc gcacccgacg   3420
tttcccgcgc aggtgtcggt ggatggcggg tggccacggg caggctcctt ccatgcctct   3480
ttttgccccc atgtgcttgg ctgccgggat caagtgattg ccgaaggcca gattgagttt   3540
gacatctcag agcctgaagt ggccgcaact gtgaaggttc cagaaggaaa gtccttggtt   3600
ttggtccgtg ttctagtggt gcctgcagaa aactatgact accaaatact tcacaaaaaa   3660
tccatggaca agtcactcga gtttatcacc aattgtggaa aaaacagctt ttaccttgac   3720
ccccagacag cctccagatt ctgtaagaat tccgccaggt ccctggtggc cttttaccac   3780
aagggcgccc tgccttgtga gtgccacccc actggggcca ccggccctca ctgcagccct   3840
gagggtgggc agtgcccatg ccagcccaac gtcatcgggc ggcagtgcac ccgctgtgca   3900
acaggccact acggattccc acgctgcaag ccgtgcagct gtggtcggcg cctttgtgaa   3960
gagatgacgg ggcagtgccg ctgccctccc cgcacggtca ggccccagtg tgaggtgtgt   4020
gagacacact cattcagctt ccaccccatg gccggctgcg aaggctgcaa ctgttccagg   4080
aggggcacca tcgaggctgc catgccggag tgtgaccggg acagcgggca gtgcagatgc   4140
aagcccagaa tcacagggcg gcagtgtgac cgatgtgctt ccgggtttta ccgctttcct   4200
gagtgtgttc cctgcaattg caacagagat gggactgagc caggagtgtg tgacccaggg   4260
accggggctt gcctctgcaa ggaaaatgta gaaggcacag agtgtaatgt gtgtcgagaa   4320
ggctcattcc atttggaccc agccaatctc aagggttgta ccagctgttt ctgttttgga   4380
gtaaataatc aatgtcacag ctcacataag cgaaggacta agtttgtgga tatgctgggc   4440
tggcacctgg agacagcaga cagagtggac atccctgtct ctttcaaccc aggcagcaac   4500
agtatggtgg cggatctcca ggagctgccc gcaaccatcc acagcgcgtc ctgggtcgca   4560
cccacctcct acctggggga caaggtttct tcatatggtg gttacctcac ttaccaagcc   4620
aagtcctttg gcttgcctgg cgacatggtt cttctggaaa agaagccgga tgtacagctc   4680
actggtcagc acatgtccat catctatgag gagacaaaca ccccacggcc agaccggctg   4740
catcatggac gagtgcacgt ggtcgaggga aacttcagac atgccagcag ccgtgcccca   4800
gtgtctaggg aggagctgat gacagtgctg tctagactgg cagatgtgcg catccaaggc   4860
ctctacttca cagagactca aaggctcacc ctgagcgagg tggggctaga ggaagcctct   4920
gacacaggaa gtgggcgcat agcacttgct gtggaaatct gtgcctgccc ccctgcctac   4980
gctggtgact cttgtcaggg ttgtagccct ggatactatc gggatcataa aggcttgtat   5040
accggacggt gtgttccctg caattgcaac ggacattcaa atcaatgcca ggatggctca   5100
ggcatatgtg ttaactgtca gcacaacacc gcgggagagc actgtgaacg ctgccaggag   5160
ggctactatg gcaacgccgt ccacggatcc tgcagggcct gcccatgtcc tcacactaac   5220
agctttgcca ctggctgtgt ggtgaatggg ggagacgtgc ggtgctcctg caaagctggg   5280
tacacaggaa cacagtgtga aaggtgtgca ccgggatatt tcgggaatcc ccagaaattc   5340
ggaggtagct gccaaccatg cagttgtaac agcaatggcc agctgggcag ctgtcatccc   5400
ctgactggag actgcataaa ccaagaaccc aaagatagca gccctgcaga agaatgtgat   5460
```

-continued

```
gattgcgaca gctgtgtgat gaccctcctg aacgacctgg ccaccatggg cgagcagctc   5520
cgcctggtca agtctcagct gcagggcctg agtgccagcg cagggcttct ggagcagatg   5580
aggcacatgg agacccaggc caaggacctg aggaatcagt tgctcaacta ccgttctgcc   5640
atttcaaatc atggatcaaa aatagaaggc ctggaaagag aactgactga tttgaatcaa   5700
gaatttgaga ctttgcaaga aaaggctcaa gtaaattcca gaaaagcaca aacattaaac   5760
aacaatgtta atcgggcaac acaaagcgca aaagaactgg atgtgaagat taaaaatgtc   5820
atccggaatg tgcacattct tttaaagcag atctctggga cagatggaga gggaaacaac   5880
gtgccttcag gtgacttttc cagagagtgg gctgaagccc agcgcatgat gagggaactg   5940
cggaacagga actttggaaa gcacctcaga gaagcagaag ctgataaaag ggagtcgcag   6000
ctcttgctga accggataag gacctggcag aaaacccacc agggggagaa caatgggctt   6060
gctaacagta tccgggattc tttaaatgaa tacgaagcca aactcagtga ccttcgtgct   6120
cggctgcagg aggcagctgc ccaagccaag caggcaaatg gcttgaacca agaaaacgag   6180
agagctttgg gagccattca gagacaagtg aaagaaataa attccctgca gagtgatttc   6240
accaagtatc taaccactgc agactcatct ttgttgcaaa ccaacattgc gctgcagctg   6300
atggagaaaa gccagaagga atatgaaaaa ttagctgcca gtttaaatga agcaagacaa   6360
gaactaagtg acaaagtaag agaactttcc agatctgctg gcaaaacatc ccttgtggag   6420
gaggcagaaa agcacgcgcg gtccttacaa gagctggcaa agcagctgga agagatcaag   6480
agaaacgcca gcggggatga gctggtgcgc tgtgctgtgg atgccgccac cgcctacgag   6540
aacatcctca atgccatcaa agcggccgag gacgcagcca acagggctgc cagtgcatct   6600
gaatctgccc tccagacagt gataaaggaa gatctgccaa gaaaagctaa aaccctgagt   6660
tccaacagtg ataaactgtt aaatgaagcc aagatgacac aaaagaagct aaagcaagaa   6720
gtcagtccag ctctcaacaa cctacagcaa accctgaata ttgtgacagt tcagaaagaa   6780
gtgatagaca ccaatctcac aactctccga gatggtcttc atgggataca gagaggtgat   6840
attgatgcta tgatcagtag tgcaaagagc atggtcagaa aggccaacga catcacagat   6900
gaggttctgg atgggctcaa ccccatccag acagatgtgg aaagaattaa ggacacctat   6960
gggaggacac agaacgaaga cttcaaaaag gctctgactg atgcagataa ctcggtgaat   7020
aagttaacca acaaactacc tgatctttgg cgcaagattg aaagtatcaa ccaacagctg   7080
ttgcccttgg gaaacatctc tgacaacatg gacagaatac gagaactaat tcagcaggcc   7140
agagatgctg ccagtaaggt tgctgtcccc atgaggttca atggtaaatc tggagtcgaa   7200
gtccgactgc caaatgacct ggaagatttg aaaggatata catctctgtc cttgtttctc   7260
caaaggccca actcaagaga aaatgggggt actgagaata tgtttgtgat gtaccttgga   7320
aataaagatg cctcccggga ctacatcggc atggcagttg tggatggcca gctcacctgt   7380
gtctacaacc tgggggaccg tgaggctgaa ctccaagtgg accagatctt gaccaagagt   7440
gagactaagg aggcagttat ggatcgggtg aaatttcaga gaatttatca gtttgcaagg   7500
cttaattaca ccaaaggagc cacatccagt aaaccagaaa cacccggagt ctatgacatg   7560
gatggtagaa atagcaatac actccttaat ttggatcctg aaaatgttgt attttatgtt   7620
ggaggttacc cacctgattt taaacttccc agtcgactaa gtttccctcc atacaaaggt   7680
tgtattgaat tagatgacct caatgaaaat gttctgagct tgtacaactt caaaaaaaca   7740
ttcaatctca acacaactga agtggagcct tgtagaagga ggaaggaaga gtcagacaaa   7800
aattattttg aaggtacggg ctatgctcga gttccaactc aaccacatgc tcccatccca   7860
```

-continued

```
acctttggac agacaattca gaccaccgtg gatagaggct tgctgttctt tgcagaaaac   7920
ggggatcgct tcatatctct aaatatagaa gatggcaagc tcatggtgag atacaaactg   7980
aattcagagc taccaaaaga gagaggagtt ggagacgcca taaacaacgg cagagaccat   8040
tcgattcaga tcaaaattgg aaaactccaa aagcgtatgt ggataaatgt ggacgttcaa   8100
aacactataa ttgatggtga agtatttgat ttcagcacat attatctggg aggaattcca   8160
attgcaatca gggaaagatt taacatttct acgcctgctt tccgaggctg catgaaaaat   8220
ttgaagaaaa ccagtggtgt cgttagattg aatgatactg tgggagtaac caaaaagtgc   8280
tcggaagact ggaagcttgt gcgatctgcc tcattctcca gaggaggaca attgagtttc   8340
actgatttgg gcttaccacc tactgaccac ctccaggcct catttggatt tcagaccttt   8400
caacccagtg gcatattatt agatcatcag acatggacaa ggaacctgca ggtcactctg   8460
gaagatggtt acattgaatt gagcaccagc gatagcggcg gcccaatttt taaatctcca   8520
cagacgtata tggatggttt actgcattat gtatctgtaa taagcgacaa ctctggacta   8580
cggcttctca tcgatgacca gcttctgaga aatagcaaaa ggctaaaaca catttcaagt   8640
tcccggcagt ctctgcgtct gggcgggagc aattttgagg gttgtattag caatgttttt   8700
gtccagaggt tatcactgag tcctgaagtc ctagatttga ccagtaactc tctcaagaga   8760
gatgtgtccc tgggaggctg cagtttaaac aaaccacctt ttctaatgtt gcttaaaggt   8820
tctaccaggt ttaacaagac caagactttt cgtatcaacc agctgttgca ggacacacca   8880
gtggcctccc caaggagcgt gaaggtgtgg caagatgctt gctcaccact tcccaagacc   8940
caggccaatc atggagccct ccagtttggg gacattccca ccagccactt gctattcaag   9000
cttcctcagg agctgctgaa acccaggtca cagtttgctg tggacatgca gacaacatcc   9060
tccagaggac tggtgtttca cacgggcact aagaactcct ttatggctct ttatctttca   9120
aaaggacgtc tggtctttgc actggggaca gatgggaaaa aattgaggat caaaagcaag   9180
gagaaatgca atgatgggaa atggcacacg gtggtgtttg gccatgatgg ggaaaagggg   9240
cgcttggttg tggatggact gagggcccgg gagggaagtt tgcctggaaa ctccaccatc   9300
agcatcagag cgccagttta cctgggatca cctccatcag ggaaaccaaa gagcctcccc   9360
acaaacagct ttgtgggatg cctgaagaac tttcagctgg attcaaaacc cttgtatacc   9420
ccttcttcaa gcttcggggt gtcttcctgc ttgggtggtc ctttggagaa aggcatttat   9480
ttctctgaag aaggaggtca tgtcgtcttg gctcactctg tattgttggg gccagaattt   9540
aagcttgttt tcagcatccg cccaagaagt ctcactggga tcctaataca catcggaagt   9600
cagcccggga agcacttatg tgtttacctg gaggcaggaa aggtcacggc ctctatggac   9660
agtggggcag gtgggacctc aacgtcggtc acaccaaagc agtctctgtg tgatggacag   9720
tggcactcgg tggcagtcac cataaaacaa cacatcctgc acctggaact ggacacagac   9780
agtagctaca cagctggaca gatccccttc ccacctgcca gcactcaaga gccactacac   9840
cttggaggtg ctccagccaa tttgacgaca ctgaggatcc ctgtgtggaa atcattcttt   9900
ggctgtctga ggaatattca tgtcaatcac atccctgtcc ctgtcactga agccttggaa   9960
gtccaggggc ctgtcagtct gaatggttgt cctgaccagt aa                      10002
```

<210> SEQ ID NO 2
<211> LENGTH: 3333
<212> TYPE: PRT
<213> ORGANISM: Homo sapiens

<400> SEQUENCE: 2

-continued

```
Met Ala Ala Ala Ala Arg Pro Arg Gly Arg Ala Leu Gly Pro Val Leu
  1               5                  10                  15

Pro Pro Thr Pro Leu Leu Leu Leu Val Leu Arg Val Leu Pro Ala Cys
             20                  25                  30

Gly Ala Thr Ala Arg Asp Pro Gly Ala Ala Ala Gly Leu Ser Leu His
         35                  40                  45

Pro Thr Tyr Phe Asn Leu Ala Glu Ala Ala Arg Ile Trp Ala Thr Ala
     50                  55                  60

Thr Cys Gly Glu Arg Gly Pro Gly Glu Gly Arg Pro Gln Pro Glu Leu
 65                  70                  75                  80

Tyr Cys Lys Leu Val Gly Gly Pro Thr Ala Pro Gly Ser Gly His Thr
                 85                  90                  95

Ile Gln Gly Gln Phe Cys Asp Tyr Cys Asn Ser Glu Asp Pro Arg Lys
            100                 105                 110

Ala His Pro Val Thr Asn Ala Ile Asp Gly Ser Glu Arg Trp Trp Gln
        115                 120                 125

Ser Pro Pro Leu Ser Ser Gly Thr Gln Tyr Asn Arg Val Asn Leu Thr
    130                 135                 140

Leu Asp Leu Gly Gln Leu Phe His Val Ala Tyr Ile Leu Ile Lys Phe
145                 150                 155                 160

Ala Asn Ser Pro Arg Pro Asp Leu Trp Val Leu Glu Arg Ser Val Asp
                165                 170                 175

Phe Gly Ser Thr Tyr Ser Pro Trp Gln Tyr Phe Ala His Ser Lys Val
            180                 185                 190

Asp Cys Leu Lys Glu Phe Gly Arg Glu Ala Asn Met Ala Val Thr Arg
        195                 200                 205

Asp Asp Asp Val Leu Cys Val Thr Glu Tyr Ser Arg Ile Val Pro Leu
    210                 215                 220

Glu Asn Gly Glu Val Val Val Ser Leu Ile Asn Gly Arg Pro Gly Ala
225                 230                 235                 240

Lys Asn Phe Thr Phe Ser His Thr Leu Arg Glu Phe Thr Lys Ala Thr
                245                 250                 255

Asn Ile Arg Leu Arg Phe Leu Arg Thr Asn Thr Leu Leu Gly His Leu
            260                 265                 270

Ile Ser Lys Ala Gln Arg Asp Pro Thr Val Thr Arg Arg Tyr Tyr Tyr
        275                 280                 285

Ser Ile Lys Asp Ile Ser Ile Gly Gly Gln Cys Val Cys Asn Gly His
    290                 295                 300

Ala Glu Val Cys Asn Ile Asn Asn Pro Glu Lys Leu Phe Arg Cys Glu
305                 310                 315                 320

Cys Gln His His Thr Cys Gly Glu Thr Cys Asp Arg Cys Cys Thr Gly
                325                 330                 335

Tyr Asn Gln Arg Arg Trp Arg Pro Ala Ala Trp Glu Gln Ser His Glu
            340                 345                 350

Cys Glu Ala Cys Asn Cys His Gly His Ala Ser Asn Cys Tyr Tyr Asp
        355                 360                 365

Pro Asp Val Glu Arg Gln Gln Ala Ser Leu Asn Thr Gln Gly Ile Tyr
    370                 375                 380

Ala Gly Gly Gly Val Cys Ile Asn Cys Gln His Asn Thr Ala Gly Val
385                 390                 395                 400

Asn Cys Glu Gln Cys Ala Lys Gly Tyr Tyr Arg Pro Tyr Gly Val Pro
                405                 410                 415

Val Asp Ala Pro Asp Gly Cys Ile Pro Cys Ser Cys Asp Pro Glu His
            420                 425                 430
```

-continued

```
Ala Asp Gly Cys Glu Gln Gly Ser Gly Arg Cys His Cys Lys Pro Asn
        435                 440                 445

Phe His Gly Asp Asn Cys Glu Lys Cys Ala Ile Gly Tyr Tyr Asn Phe
    450                 455                 460

Pro Phe Cys Leu Arg Ile Pro Ile Phe Pro Val Ser Thr Pro Ser Ser
465                 470                 475                 480

Glu Asp Pro Val Ala Gly Asp Ile Lys Gly Cys Asp Cys Asn Leu Glu
                485                 490                 495

Gly Val Leu Pro Glu Ile Cys Asp Ala His Gly Arg Cys Leu Cys Arg
            500                 505                 510

Pro Gly Val Glu Gly Pro Arg Cys Asp Thr Cys Arg Ser Gly Phe Tyr
        515                 520                 525

Ser Phe Pro Ile Cys Gln Ala Cys Trp Cys Ser Ala Leu Gly Ser Tyr
    530                 535                 540

Gln Met Pro Cys Ser Ser Val Thr Gly Gln Cys Glu Cys Arg Pro Gly
545                 550                 555                 560

Val Thr Gly Gln Arg Cys Asp Arg Cys Leu Ser Gly Ala Tyr Asp Phe
                565                 570                 575

Pro His Cys Gln Gly Ser Ser Ser Ala Cys Asp Pro Ala Gly Thr Ile
            580                 585                 590

Asn Ser Asn Leu Gly Tyr Cys Gln Cys Lys Leu His Val Glu Gly Pro
        595                 600                 605

Thr Cys Ser Arg Cys Lys Leu Leu Tyr Trp Asn Leu Asp Lys Glu Asn
    610                 615                 620

Pro Ser Gly Cys Ser Glu Cys Lys Cys His Lys Ala Gly Thr Val Ser
625                 630                 635                 640

Gly Thr Gly Glu Cys Arg Gln Gly Asp Gly Asp Cys His Cys Lys Ser
                645                 650                 655

His Val Gly Gly Asp Ser Cys Asp Thr Cys Glu Asp Gly Tyr Phe Ala
            660                 665                 670

Leu Glu Lys Ser Asn Tyr Phe Gly Cys Gln Gly Cys Gln Cys Asp Ile
        675                 680                 685

Gly Gly Ala Leu Ser Ser Met Cys Ser Gly Pro Ser Gly Val Cys Gln
    690                 695                 700

Cys Arg Glu His Val Val Gly Lys Val Cys Gln Arg Pro Glu Asn Asn
705                 710                 715                 720

Tyr Tyr Phe Pro Asp Leu His His Met Lys Tyr Glu Ile Glu Asp Gly
                725                 730                 735

Ser Thr Pro Asn Gly Arg Asp Leu Arg Phe Gly Phe Asp Pro Leu Ala
            740                 745                 750

Phe Pro Glu Phe Ser Trp Arg Gly Tyr Ala Gln Met Thr Ser Val Gln
        755                 760                 765

Asn Asp Val Arg Ile Thr Leu Asn Val Gly Lys Ser Ser Gly Ser Leu
    770                 775                 780

Phe Arg Val Ile Leu Arg Tyr Val Asn Pro Gly Thr Glu Ala Val Ser
785                 790                 795                 800

Gly His Ile Thr Ile Tyr Pro Ser Trp Gly Ala Ala Gln Ser Lys Glu
                805                 810                 815

Ile Ile Phe Leu Pro Ser Lys Glu Pro Ala Phe Val Thr Val Pro Gly
            820                 825                 830

Asn Gly Phe Ala Asp Pro Phe Ser Ile Thr Pro Gly Ile Trp Val Ala
        835                 840                 845

Cys Ile Lys Ala Glu Gly Val Leu Leu Asp Tyr Leu Val Leu Leu Pro
```

-continued

```
    850                 855                 860

Arg Asp Tyr Tyr Glu Ala Ser Val Leu Gln Leu Pro Val Thr Glu Pro
865                 870                 875                 880

Cys Ala Tyr Ala Gly Pro Pro Gln Glu Asn Cys Leu Leu Tyr Gln His
                885                 890                 895

Leu Pro Val Thr Arg Phe Pro Cys Thr Leu Ala Cys Glu Ala Arg His
            900                 905                 910

Phe Leu Leu Asp Gly Glu Pro Arg Pro Val Ala Val Arg Gln Pro Thr
        915                 920                 925

Pro Ala His Pro Val Met Val Asp Leu Ser Gly Arg Glu Val Glu Leu
    930                 935                 940

His Leu Arg Leu Arg Ile Pro Gln Val Gly His Tyr Val Val Val Val
945                 950                 955                 960

Glu Tyr Ser Thr Glu Ala Ala Gln Leu Phe Val Val Asp Val Asn Val
                965                 970                 975

Lys Ser Ser Gly Ser Val Leu Ala Gly Gln Val Asn Ile Tyr Ser Cys
            980                 985                 990

Asn Tyr Ser Val Leu Cys Arg Ser Ala Val Ile Asp His Met Ser Arg
        995                 1000                1005

Ile Ala Met Tyr Glu Leu Leu Ala Asp Ala Asp Ile Gln Leu Lys Gly
   1010                 1015                1020

His Met Ala Arg Phe Leu Leu His Gln Val Cys Ile Ile Pro Ile Glu
1025                1030                1035                1040

Glu Phe Ser Ala Glu Tyr Val Arg Pro Gln Val His Cys Ile Ala Ser
               1045                1050                1055

Tyr Gly Arg Phe Val Asn Gln Ser Ala Thr Cys Val Ser Leu Ala His
           1060                1065                1070

Glu Thr Pro Pro Thr Ala Leu Ile Leu Asp Val Leu Ser Gly Arg Pro
       1075                1080                1085

Phe Pro His Leu Pro Gln Gln Ser Ser Pro Ser Val Asp Val Leu Pro
   1090                1095                1100

Gly Val Thr Leu Lys Ala Pro Gln Asn Gln Val Thr Leu Arg Gly Arg
1105                1110                1115                1120

Val Pro His Leu Gly Arg Tyr Val Phe Val Ile His Phe Tyr Gln Ala
               1125                1130                1135

Ala His Pro Thr Phe Pro Ala Gln Val Ser Val Asp Gly Gly Trp Pro
           1140                1145                1150

Arg Ala Gly Ser Phe His Ala Ser Phe Cys Pro His Val Leu Gly Cys
       1155                1160                1165

Arg Asp Gln Val Ile Ala Glu Gly Gln Ile Glu Phe Asp Ile Ser Glu
   1170                1175                1180

Pro Glu Val Ala Ala Thr Val Lys Val Pro Glu Gly Lys Ser Leu Val
1185                1190                1195                1200

Leu Val Arg Val Leu Val Val Pro Ala Glu Asn Tyr Asp Tyr Gln Ile
               1205                1210                1215

Leu His Lys Lys Ser Met Asp Lys Ser Leu Glu Phe Ile Thr Asn Cys
           1220                1225                1230

Gly Lys Asn Ser Phe Tyr Leu Asp Pro Gln Thr Ala Ser Arg Phe Cys
       1235                1240                1245

Lys Asn Ser Ala Arg Ser Leu Val Ala Phe Tyr His Lys Gly Ala Leu
   1250                1255                1260

Pro Cys Glu Cys His Pro Thr Gly Ala Thr Gly Pro His Cys Ser Pro
1265                1270                1275                1280
```

```
Glu Gly Gly Gln Cys Pro Cys Gln Pro Asn Val Ile Gly Arg Gln Cys
            1285                1290                1295

Thr Arg Cys Ala Thr Gly His Tyr Gly Phe Pro Arg Cys Lys Pro Cys
        1300                1305                1310

Ser Cys Gly Arg Arg Leu Cys Glu Glu Met Thr Gly Gln Cys Arg Cys
    1315                1320                1325

Pro Pro Arg Thr Val Arg Pro Gln Cys Glu Val Cys Glu Thr His Ser
  1330                1335                1340

Phe Ser Phe His Pro Met Ala Gly Cys Glu Gly Cys Asn Cys Ser Arg
1345                1350                1355                1360

Arg Gly Thr Ile Glu Ala Ala Met Pro Glu Cys Asp Arg Asp Ser Gly
            1365                1370                1375

Gln Cys Arg Cys Lys Pro Arg Ile Thr Gly Arg Gln Cys Asp Arg Cys
        1380                1385                1390

Ala Ser Gly Phe Tyr Arg Phe Pro Glu Cys Val Pro Cys Asn Cys Asn
    1395                1400                1405

Arg Asp Gly Thr Glu Pro Gly Val Cys Asp Pro Gly Thr Gly Ala Cys
  1410                1415                1420

Leu Cys Lys Glu Asn Val Glu Gly Thr Glu Cys Asn Val Cys Arg Glu
1425                1430                1435                1440

Gly Ser Phe His Leu Asp Pro Ala Asn Leu Lys Gly Cys Thr Ser Cys
            1445                1450                1455

Phe Cys Phe Gly Val Asn Asn Gln Cys His Ser Ser His Lys Arg Arg
        1460                1465                1470

Thr Lys Phe Val Asp Met Leu Gly Trp His Leu Glu Thr Ala Asp Arg
    1475                1480                1485

Val Asp Ile Pro Val Ser Phe Asn Pro Gly Ser Asn Ser Met Val Ala
  1490                1495                1500

Asp Leu Gln Glu Leu Pro Ala Thr Ile His Ser Ala Ser Trp Val Ala
1505                1510                1515                1520

Pro Thr Ser Tyr Leu Gly Asp Lys Val Ser Ser Tyr Gly Gly Tyr Leu
            1525                1530                1535

Thr Tyr Gln Ala Lys Ser Phe Gly Leu Pro Gly Asp Met Val Leu Leu
        1540                1545                1550

Glu Lys Lys Pro Asp Val Gln Leu Thr Gly Gln His Met Ser Ile Ile
    1555                1560                1565

Tyr Glu Glu Thr Asn Thr Pro Arg Pro Asp Arg Leu His His Gly Arg
  1570                1575                1580

Val His Val Val Glu Gly Asn Phe Arg His Ala Ser Ser Arg Ala Pro
1585                1590                1595                1600

Val Ser Arg Glu Glu Leu Met Thr Val Leu Ser Arg Leu Ala Asp Val
            1605                1610                1615

Arg Ile Gln Gly Leu Tyr Phe Thr Glu Thr Gln Arg Leu Thr Leu Ser
        1620                1625                1630

Glu Val Gly Leu Glu Glu Ala Ser Asp Thr Gly Ser Gly Arg Ile Ala
    1635                1640                1645

Leu Ala Val Glu Ile Cys Ala Cys Pro Pro Ala Tyr Ala Gly Asp Ser
  1650                1655                1660

Cys Gln Gly Cys Ser Pro Gly Tyr Tyr Arg Asp His Lys Gly Leu Tyr
1665                1670                1675                1680

Thr Gly Arg Cys Val Pro Cys Asn Cys Asn Gly His Ser Asn Gln Cys
            1685                1690                1695

Gln Asp Gly Ser Gly Ile Cys Val Asn Cys Gln His Asn Thr Ala Gly
        1700                1705                1710
```

```
Glu His Cys Glu Arg Cys Gln Glu Gly Tyr Tyr Gly Asn Ala Val His
       1715                1720                1725

Gly Ser Cys Arg Ala Cys Pro Cys Pro His Thr Asn Ser Phe Ala Thr
   1730                1735                1740

Gly Cys Val Val Asn Gly Gly Asp Val Arg Cys Ser Cys Lys Ala Gly
1745                1750                1755                1760

Tyr Thr Gly Thr Gln Cys Glu Arg Cys Ala Pro Gly Tyr Phe Gly Asn
               1765                1770                1775

Pro Gln Lys Phe Gly Gly Ser Cys Gln Pro Cys Ser Cys Asn Ser Asn
           1780                1785                1790

Gly Gln Leu Gly Ser Cys His Pro Leu Thr Gly Asp Cys Ile Asn Gln
       1795                1800                1805

Glu Pro Lys Asp Ser Ser Pro Ala Glu Glu Cys Asp Asp Cys Asp Ser
   1810                1815                1820

Cys Val Met Thr Leu Leu Asn Asp Leu Ala Thr Met Gly Glu Gln Leu
1825                1830                1835                1840

Arg Leu Val Lys Ser Gln Leu Gln Gly Leu Ser Ala Ser Ala Gly Leu
               1845                1850                1855

Leu Glu Gln Met Arg His Met Glu Thr Gln Ala Lys Asp Leu Arg Asn
           1860                1865                1870

Gln Leu Leu Asn Tyr Arg Ser Ala Ile Ser Asn His Gly Ser Lys Ile
       1875                1880                1885

Glu Gly Leu Glu Arg Glu Leu Thr Asp Leu Asn Gln Glu Phe Glu Thr
   1890                1895                1900

Leu Gln Glu Lys Ala Gln Val Asn Ser Arg Lys Ala Gln Thr Leu Asn
1905                1910                1915                1920

Asn Asn Val Asn Arg Ala Thr Gln Ser Ala Lys Glu Leu Asp Val Lys
               1925                1930                1935

Ile Lys Asn Val Ile Arg Asn Val His Ile Leu Leu Lys Gln Ile Ser
           1940                1945                1950

Gly Thr Asp Gly Glu Gly Asn Asn Val Pro Ser Gly Asp Phe Ser Arg
       1955                1960                1965

Glu Trp Ala Glu Ala Gln Arg Met Met Arg Glu Leu Arg Asn Arg Asn
   1970                1975                1980

Phe Gly Lys His Leu Arg Glu Ala Glu Ala Asp Lys Arg Glu Ser Gln
1985                1990                1995                2000

Leu Leu Leu Asn Arg Ile Arg Thr Trp Gln Lys Thr His Gln Gly Glu
               2005                2010                2015

Asn Asn Gly Leu Ala Asn Ser Ile Arg Asp Ser Leu Asn Glu Tyr Glu
           2020                2025                2030

Ala Lys Leu Ser Asp Leu Arg Ala Arg Leu Gln Glu Ala Ala Ala Gln
       2035                2040                2045

Ala Lys Gln Ala Asn Gly Leu Asn Gln Glu Asn Glu Arg Ala Leu Gly
   2050                2055                2060

Ala Ile Gln Arg Gln Val Lys Glu Ile Asn Ser Leu Gln Ser Asp Phe
2065                2070                2075                2080

Thr Lys Tyr Leu Thr Thr Ala Asp Ser Ser Leu Leu Gln Thr Asn Ile
               2085                2090                2095

Ala Leu Gln Leu Met Glu Lys Ser Gln Lys Glu Tyr Glu Lys Leu Ala
           2100                2105                2110

Ala Ser Leu Asn Glu Ala Arg Gln Glu Leu Ser Asp Lys Val Arg Glu
       2115                2120                2125

Leu Ser Arg Ser Ala Gly Lys Thr Ser Leu Val Glu Glu Ala Glu Lys
```

-continued

```
   2130                2135                2140

His Ala Arg Ser Leu Gln Glu Leu Ala Lys Gln Leu Glu Glu Ile Lys
2145                2150                2155                2160

Arg Asn Ala Ser Gly Asp Glu Leu Val Arg Cys Ala Val Asp Ala Ala
                2165                2170                2175

Thr Ala Tyr Glu Asn Ile Leu Asn Ala Ile Lys Ala Ala Glu Asp Ala
            2180                2185                2190

Ala Asn Arg Ala Ala Ser Ala Ser Glu Ser Ala Leu Gln Thr Val Ile
        2195                2200                2205

Lys Glu Asp Leu Pro Arg Lys Ala Lys Thr Leu Ser Ser Asn Ser Asp
   2210                2215                2220

Lys Leu Leu Asn Glu Ala Lys Met Thr Gln Lys Lys Leu Lys Gln Glu
2225                2230                2235                2240

Val Ser Pro Ala Leu Asn Asn Leu Gln Gln Thr Leu Asn Ile Val Thr
                2245                2250                2255

Val Gln Lys Glu Val Ile Asp Thr Asn Leu Thr Thr Leu Arg Asp Gly
            2260                2265                2270

Leu His Gly Ile Gln Arg Gly Asp Ile Asp Ala Met Ile Ser Ser Ala
        2275                2280                2285

Lys Ser Met Val Arg Lys Ala Asn Asp Ile Thr Asp Glu Val Leu Asp
   2290                2295                2300

Gly Leu Asn Pro Ile Gln Thr Asp Val Glu Arg Ile Lys Asp Thr Tyr
2305                2310                2315                2320

Gly Arg Thr Gln Asn Glu Asp Phe Lys Lys Ala Leu Thr Asp Ala Asp
                2325                2330                2335

Asn Ser Val Asn Lys Leu Thr Asn Lys Leu Pro Asp Leu Trp Arg Lys
            2340                2345                2350

Ile Glu Ser Ile Asn Gln Gln Leu Leu Pro Leu Gly Asn Ile Ser Asp
        2355                2360                2365

Asn Met Asp Arg Ile Arg Glu Leu Ile Gln Gln Ala Arg Asp Ala Ala
   2370                2375                2380

Ser Lys Val Ala Val Pro Met Arg Phe Asn Gly Lys Ser Gly Val Glu
2385                2390                2395                2400

Val Arg Leu Pro Asn Asp Leu Glu Asp Leu Lys Gly Tyr Thr Ser Leu
                2405                2410                2415

Ser Leu Phe Leu Gln Arg Pro Asn Ser Arg Glu Asn Gly Gly Thr Glu
            2420                2425                2430

Asn Met Phe Val Met Tyr Leu Gly Asn Lys Asp Ala Ser Arg Asp Tyr
        2435                2440                2445

Ile Gly Met Ala Val Val Asp Gly Gln Leu Thr Cys Val Tyr Asn Leu
   2450                2455                2460

Gly Asp Arg Glu Ala Glu Leu Gln Val Asp Gln Ile Leu Thr Lys Ser
2465                2470                2475                2480

Glu Thr Lys Glu Ala Val Met Asp Arg Val Lys Phe Gln Arg Ile Tyr
                2485                2490                2495

Gln Phe Ala Arg Leu Asn Tyr Thr Lys Gly Ala Thr Ser Ser Lys Pro
            2500                2505                2510

Glu Thr Pro Gly Val Tyr Asp Met Asp Gly Arg Asn Ser Asn Thr Leu
        2515                2520                2525

Leu Asn Leu Asp Pro Glu Asn Val Val Phe Tyr Val Gly Gly Tyr Pro
   2530                2535                2540

Pro Asp Phe Lys Leu Pro Ser Arg Leu Ser Phe Pro Pro Tyr Lys Gly
2545                2550                2555                2560
```

-continued

```
Cys Ile Glu Leu Asp Asp Leu Asn Glu Asn Val Leu Ser Leu Tyr Asn
                2565                2570                2575

Phe Lys Lys Thr Phe Asn Leu Asn Thr Thr Glu Val Glu Pro Cys Arg
            2580                2585                2590

Arg Arg Lys Glu Glu Ser Asp Lys Asn Tyr Phe Glu Gly Thr Gly Tyr
        2595                2600                2605

Ala Arg Val Pro Thr Gln Pro His Ala Pro Ile Pro Thr Phe Gly Gln
    2610                2615                2620

Thr Ile Gln Thr Thr Val Asp Arg Gly Leu Leu Phe Phe Ala Glu Asn
2625                2630                2635                2640

Gly Asp Arg Phe Ile Ser Leu Asn Ile Glu Asp Gly Lys Leu Met Val
                2645                2650                2655

Arg Tyr Lys Leu Asn Ser Glu Leu Pro Lys Glu Arg Gly Val Gly Asp
            2660                2665                2670

Ala Ile Asn Asn Gly Arg Asp His Ser Ile Gln Ile Lys Ile Gly Lys
        2675                2680                2685

Leu Gln Lys Arg Met Trp Ile Asn Val Asp Val Gln Asn Thr Ile Ile
    2690                2695                2700

Asp Gly Glu Val Phe Asp Phe Ser Thr Tyr Tyr Leu Gly Gly Ile Pro
2705                2710                2715                2720

Ile Ala Ile Arg Glu Arg Phe Asn Ile Ser Thr Pro Ala Phe Arg Gly
                2725                2730                2735

Cys Met Lys Asn Leu Lys Lys Thr Ser Gly Val Val Arg Leu Asn Asp
            2740                2745                2750

Thr Val Gly Val Thr Lys Lys Cys Ser Glu Asp Trp Lys Leu Val Arg
        2755                2760                2765

Ser Ala Ser Phe Ser Arg Gly Gly Gln Leu Ser Phe Thr Asp Leu Gly
    2770                2775                2780

Leu Pro Pro Thr Asp His Leu Gln Ala Ser Phe Gly Phe Gln Thr Phe
2785                2790                2795                2800

Gln Pro Ser Gly Ile Leu Leu Asp His Gln Thr Trp Thr Arg Asn Leu
                2805                2810                2815

Gln Val Thr Leu Glu Asp Gly Tyr Ile Glu Leu Ser Thr Ser Asp Ser
            2820                2825                2830

Gly Gly Pro Ile Phe Lys Ser Pro Gln Thr Tyr Met Asp Gly Leu Leu
        2835                2840                2845

His Tyr Val Ser Val Ile Ser Asp Asn Ser Gly Leu Arg Leu Leu Ile
    2850                2855                2860

Asp Asp Gln Leu Leu Arg Asn Ser Lys Arg Leu Lys His Ile Ser Ser
2865                2870                2875                2880

Ser Arg Gln Ser Leu Arg Leu Gly Gly Ser Asn Phe Glu Gly Cys Ile
                2885                2890                2895

Ser Asn Val Phe Val Gln Arg Leu Ser Leu Ser Pro Glu Val Leu Asp
            2900                2905                2910

Leu Thr Ser Asn Ser Leu Lys Arg Asp Val Ser Leu Gly Gly Cys Ser
        2915                2920                2925

Leu Asn Lys Pro Pro Phe Leu Met Leu Leu Lys Gly Ser Thr Arg Phe
    2930                2935                2940

Asn Lys Thr Lys Thr Phe Arg Ile Asn Gln Leu Leu Gln Asp Thr Pro
2945                2950                2955                2960

Val Ala Ser Pro Arg Ser Val Lys Val Trp Gln Asp Ala Cys Ser Pro
                2965                2970                2975

Leu Pro Lys Thr Gln Ala Asn His Gly Ala Leu Gln Phe Gly Asp Ile
            2980                2985                2990
```

Pro Thr Ser His Leu Leu Phe Lys Leu Pro Gln Glu Leu Leu Lys Pro
2995 3000 3005

Arg Ser Gln Phe Ala Val Asp Met Gln Thr Thr Ser Ser Arg Gly Leu
3010 3015 3020

Val Phe His Thr Gly Thr Lys Asn Ser Phe Met Ala Leu Tyr Leu Ser
3025 3030 3035 3040

Lys Gly Arg Leu Val Phe Ala Leu Gly Thr Asp Gly Lys Lys Leu Arg
3045 3050 3055

Ile Lys Ser Lys Glu Lys Cys Asn Asp Gly Lys Trp His Thr Val Val
3060 3065 3070

Phe Gly His Asp Gly Glu Lys Gly Arg Leu Val Val Asp Gly Leu Arg
3075 3080 3085

Ala Arg Glu Gly Ser Leu Pro Gly Asn Ser Thr Ile Ser Ile Arg Ala
3090 3095 3100

Pro Val Tyr Leu Gly Ser Pro Pro Ser Gly Lys Pro Lys Ser Leu Pro
3105 3110 3115 3120

Thr Asn Ser Phe Val Gly Cys Leu Lys Asn Phe Gln Leu Asp Ser Lys
3125 3130 3135

Pro Leu Tyr Thr Pro Ser Ser Ser Phe Gly Val Ser Ser Cys Leu Gly
3140 3145 3150

Gly Pro Leu Glu Lys Gly Ile Tyr Phe Ser Glu Glu Gly Gly His Val
3155 3160 3165

Val Leu Ala His Ser Val Leu Leu Gly Pro Glu Phe Lys Leu Val Phe
3170 3175 3180

Ser Ile Arg Pro Arg Ser Leu Thr Gly Ile Leu Ile His Ile Gly Ser
3185 3190 3195 3200

Gln Pro Gly Lys His Leu Cys Val Tyr Leu Glu Ala Gly Lys Val Thr
3205 3210 3215

Ala Ser Met Asp Ser Gly Ala Gly Gly Thr Ser Thr Ser Val Thr Pro
3220 3225 3230

Lys Gln Ser Leu Cys Asp Gly Gln Trp His Ser Val Ala Val Thr Ile
3235 3240 3245

Lys Gln His Ile Leu His Leu Glu Leu Asp Thr Asp Ser Ser Tyr Thr
3250 3255 3260

Ala Gly Gln Ile Pro Phe Pro Pro Ala Ser Thr Gln Glu Pro Leu His
3265 3270 3275 3280

Leu Gly Gly Ala Pro Ala Asn Leu Thr Thr Leu Arg Ile Pro Val Trp
3285 3290 3295

Lys Ser Phe Phe Gly Cys Leu Arg Asn Ile His Val Asn His Ile Pro
3300 3305 3310

Val Pro Val Thr Glu Ala Leu Glu Val Gln Gly Pro Val Ser Leu Asn
3315 3320 3325

Gly Cys Pro Asp Gln
3330

<210> SEQ ID NO 3
<211> LENGTH: 3519
<212> TYPE: DNA
<213> ORGANISM: Homo sapiens

<400> SEQUENCE: 3
atgagaccat tcttcctctt gtgttttgcc ctgcctggcc tcctgcatgc ccaacaagcc 60
tgctcccgtg gggcctgcta tccacctgtt ggggacctgc ttgttgggag gacccggttt 120
ctccgagctt catctacctg tggactgacc aagcctgaga cctactgcac ccagtatggc 180

-continued

```
gagtggcaga tgaaatgctg caagtgtgac tccaggcagc ctcacaacta ctacagtcac    240
cgagtagaga atgtggcttc atcctccggc cccatgcgct ggtggcagtc ccagaatgat    300
gtgaaccctg tctctctgca gctggacctg gacaggagat tccagcttca agaagtcatg    360
atggagttcc aggggcccat gcccgccggc atgctgattg agcgctcctc agacttcggt    420
aagacctggc gagtgtacca gtacctggct gccgactgca cctccacctt ccctcgggtc    480
cgccagggtc ggcctcagag ctggcaggat gttcggtgcc agtccctgcc tcagaggcct    540
aatgcacgcc taaatggggg gaaggtccaa cttaacctta tggatttagt gtctgggatt    600
ccagcaactc aaagtcaaaa aattcaagag gtgggggaga tcacaaactt gagagtcaat    660
ttcaccaggc tggcccctgt gccccaaagg ggctaccacc ctcccagcgc ctactatgct    720
gtgtcccagc tccgtctgca ggggagctgc ttctgtcacg gccatgctga tcgctgcgca    780
cccaagcctg gggcctctgc aggcccctcc accgctgtgc aggtccacga tgtctgtgtc    840
tgccagcaca acactgccgg cccaaattgt gagcgctgtg caccccttcta caacaaccgg    900
ccctggagac cggcggaggg ccaggacgcc catgaatgcc aaaggtgcga ctgcaatggg    960
cactcagaga catgtcactt tgaccccgct gtgtttgccg ccagccaggg ggcatatgga   1020
ggtgtgtgtg acaattgccg ggaccacacc gaaggcaaga actgtgagcg gtgtcagctg   1080
cactatttcc ggaaccggcg cccgggagct tccattcagg agacctgcat ctcctgcgag   1140
tgtgatccag atggggcagt gccaggggct ccctgtgacc cagtgaccgg gcagtgtgtg   1200
tgcaaggagc atgtgcaggg agagcgctgt gacctatgca agccgggctt cactggactc   1260
acctacgcca acccgcaggg ctgccaccgc tgtgactgca acatcctggg gtcccggagg   1320
gacatgccgt gtgacgagga gagtgggcgc tgcctttgtc tgcccaacgt ggtgggtccc   1380
aaatgtgacc agtgtgctcc ctaccactgg aagctggcca gtggccaggg ctgtgaaccg   1440
tgtgcctgcg acccgcacaa ctccctcagc ccacagtgca accagttcac agggcagtgc   1500
ccctgtcggg aaggctttgg tggcctgatg tgcagcgctg cagccatccg ccagtgtcca   1560
gaccggacct atggagacat ggccacagga tgccgagcct gtgactgtga tttccgggga   1620
acagagggcc cgggctgcga caaggcatca ggccgctgcc tctgccgccc tggcttgacc   1680
gggccccgct gtgaccagtg ccagcgaggc tactgcaatc gctacccggt gtgcgtggcc   1740
tgccaccctt gcttccagac ctatgatgca gacctccggg agcaggccct gcgctttggt   1800
agactccgca atgccaccgc cagcctgtgg tcagggcctg ggctggagga ccgtggcctg   1860
gcctcccgga tcctagatgc aaagagtaag attgagcaga tccgagcagt tctcagcagc   1920
cccgcagtca cagagcagga ggtggctcag gtggccagtg ccatcctctc cctcaggcga   1980
actctccagg gcctgcagct ggatctgccc ctggaggagg agacgttgtc ccttccgaga   2040
gacctggaga gtcttgacag aagcttcaat ggtctcctta ctatgtatca gaggaagagg   2100
gagcagtttg aaaaaataag cagtgctgat ccttcaggag ccttccggat gctgagcaca   2160
gcctacgagc agtcagccca ggctgctcag caggtctccg acagctcgcg cctttttggac   2220
cagctcaggg acagccggag agaggcagag aggctggtgc ggcaggcggg aggaggagga   2280
ggcaccggca gccccaagct tgtggccctg aggctggaga tgtcttcgtt gcctgacctg   2340
acacccacct tcaacaagct ctgtggcaac tccaggcaga tggcttgcac cccaatatca   2400
tgccctggtg agctatgtcc ccaagacaat ggcacagcct gtggctcccg ctgcaggggt   2460
gtccttccca gggccggtgg ggccttcttg atggcggggc aggtggctga gcagctgcgg   2520
ggcttcaatg cccagctcca gcggaccagg cagatgatta gggcagccga ggaatctgcc   2580
```

```
tcacagattc aatccagtgc ccagcgcttg gagacccagg tgagcgccag ccgctcccag   2640

atggaggaag atgtcagacg cacacggctc ctaatccagc aggtccggga cttcctaaca   2700

gaccccgaca ctgatgcagc cactatccag gaggtcagcg aggccgtgct ggccctgtgg   2760

ctgcccacag actcagctac tgttctgcag aagatgaatg agatccaggc cattgcagcc   2820

aggctcccca acgtggactt ggtgctgtcc cagaccaagc aggacattgc gcgtgcccgc   2880

cggttgcagg ctgaggctga ggaagccagg agccgagccc atgcagtgga gggccaggtg   2940

gaagatgtgg ttgggaacct gcggcagggg acagtggcac tgcaggaagc tcaggacacc   3000

atgcaaggca ccagccgctc ccttcggctt atccaggaca gggttgctga ggttcagcag   3060

gtactgcggc cagcagaaaa gctggtgaca agcatgacca agcagctggg tgacttctgg   3120

acacggatgg aggagctccg ccaccaagcc cggcagcagg gggcagaggc agtccaggcc   3180

cagcagcttg cggaaggtgc cagcgagcag gcattgagtg cccaagaggg atttgagaga   3240

ataaaacaaa agtatgctga gttgaaggac cggttgggtc agagttccat gctgggtgag   3300

cagggtgccc ggatccagag tgtgaagaca gaggcagagg agctgtttgg ggagaccatg   3360

gagatgatgg acaggatgaa agacatggag ttggagctgc tgcggggcag ccaggccatc   3420

atgctgcgct cagcggacct gacaggactg gagaagcgtg tggagcagat ccgtgaccac   3480

atcaatgggc gcgtgctcta ctatgccacc tgcaagtga                          3519


<210> SEQ ID NO 4
<211> LENGTH: 1172
<212> TYPE: PRT
<213> ORGANISM: Homo sapiens

<400> SEQUENCE: 4

Met Arg Pro Phe Phe Leu Leu Cys Phe Ala Leu Pro Gly Leu Leu His
1               5                   10                  15

Ala Gln Gln Ala Cys Ser Arg Gly Ala Cys Tyr Pro Pro Val Gly Asp
            20                  25                  30

Leu Leu Val Gly Arg Thr Arg Phe Leu Arg Ala Ser Ser Thr Cys Gly
        35                  40                  45

Leu Thr Lys Pro Glu Thr Tyr Cys Thr Gln Tyr Gly Glu Trp Gln Met
    50                  55                  60

Lys Cys Cys Lys Cys Asp Ser Arg Gln Pro His Asn Tyr Tyr Ser His
65                  70                  75                  80

Arg Val Glu Asn Val Ala Ser Ser Ser Gly Pro Met Arg Trp Trp Gln
                85                  90                  95

Ser Gln Asn Asp Val Asn Pro Val Ser Leu Gln Leu Asp Leu Asp Arg
            100                 105                 110

Arg Phe Gln Leu Gln Glu Val Met Met Glu Phe Gln Gly Pro Met Pro
        115                 120                 125

Ala Gly Met Leu Ile Glu Arg Ser Ser Asp Phe Gly Lys Thr Trp Arg
    130                 135                 140

Val Tyr Gln Tyr Leu Ala Ala Asp Cys Thr Ser Thr Phe Pro Arg Val
145                 150                 155                 160

Arg Gln Gly Arg Pro Gln Ser Trp Gln Asp Val Arg Cys Gln Ser Leu
                165                 170                 175

Pro Gln Arg Pro Asn Ala Arg Leu Asn Gly Gly Lys Val Gln Leu Asn
            180                 185                 190

Leu Met Asp Leu Val Ser Gly Ile Pro Ala Thr Gln Ser Gln Lys Ile
        195                 200                 205
```

-continued

```
Gln Glu Val Gly Glu Ile Thr Asn Leu Arg Val Asn Phe Thr Arg Leu
    210                 215                 220

Ala Pro Val Pro Gln Arg Gly Tyr His Pro Pro Ser Ala Tyr Tyr Ala
225                 230                 235                 240

Val Ser Gln Leu Arg Leu Gln Gly Ser Cys Phe Cys His Gly His Ala
                245                 250                 255

Asp Arg Cys Ala Pro Lys Pro Gly Ala Ser Ala Gly Pro Ser Thr Ala
            260                 265                 270

Val Gln Val His Asp Val Cys Val Cys Gln His Asn Thr Ala Gly Pro
        275                 280                 285

Asn Cys Glu Arg Cys Ala Pro Phe Tyr Asn Asn Arg Pro Trp Arg Pro
    290                 295                 300

Ala Glu Gly Gln Asp Ala His Glu Cys Gln Arg Cys Asp Cys Asn Gly
305                 310                 315                 320

His Ser Glu Thr Cys His Phe Asp Pro Ala Val Phe Ala Ala Ser Gln
                325                 330                 335

Gly Ala Tyr Gly Gly Val Cys Asp Asn Cys Arg Asp His Thr Glu Gly
            340                 345                 350

Lys Asn Cys Glu Arg Cys Gln Leu His Tyr Phe Arg Asn Arg Arg Pro
        355                 360                 365

Gly Ala Ser Ile Gln Glu Thr Cys Ile Ser Cys Glu Cys Asp Pro Asp
    370                 375                 380

Gly Ala Val Pro Gly Ala Pro Cys Asp Pro Val Thr Gly Gln Cys Val
385                 390                 395                 400

Cys Lys Glu His Val Gln Gly Glu Arg Cys Asp Leu Cys Lys Pro Gly
                405                 410                 415

Phe Thr Gly Leu Thr Tyr Ala Asn Pro Gln Gly Cys His Arg Cys Asp
            420                 425                 430

Cys Asn Ile Leu Gly Ser Arg Arg Asp Met Pro Cys Asp Glu Glu Ser
        435                 440                 445

Gly Arg Cys Leu Cys Leu Pro Asn Val Val Gly Pro Lys Cys Asp Gln
    450                 455                 460

Cys Ala Pro Tyr His Trp Lys Leu Ala Ser Gly Gln Gly Cys Glu Pro
465                 470                 475                 480

Cys Ala Cys Asp Pro His Asn Ser Leu Ser Pro Gln Cys Asn Gln Phe
                485                 490                 495

Thr Gly Gln Cys Pro Cys Arg Glu Gly Phe Gly Gly Leu Met Cys Ser
            500                 505                 510

Ala Ala Ala Ile Arg Gln Cys Pro Asp Arg Thr Tyr Gly Asp Met Ala
        515                 520                 525

Thr Gly Cys Arg Ala Cys Asp Cys Asp Phe Arg Gly Thr Glu Gly Pro
    530                 535                 540

Gly Cys Asp Lys Ala Ser Gly Arg Cys Leu Cys Arg Pro Gly Leu Thr
545                 550                 555                 560

Gly Pro Arg Cys Asp Gln Cys Gln Arg Gly Tyr Cys Asn Arg Tyr Pro
                565                 570                 575

Val Cys Val Ala Cys His Pro Cys Phe Gln Thr Tyr Asp Ala Asp Leu
            580                 585                 590

Arg Glu Gln Ala Leu Arg Phe Gly Arg Leu Arg Asn Ala Thr Ala Ser
        595                 600                 605

Leu Trp Ser Gly Pro Gly Leu Glu Asp Arg Gly Leu Ala Ser Arg Ile
    610                 615                 620

Leu Asp Ala Lys Ser Lys Ile Glu Gln Ile Arg Ala Val Leu Ser Ser
625                 630                 635                 640
```

-continued

```
Pro Ala Val Thr Glu Gln Glu Val Ala Gln Val Ala Ser Ala Ile Leu
                645                 650                 655

Ser Leu Arg Arg Thr Leu Gln Gly Leu Gln Leu Asp Leu Pro Leu Glu
            660                 665                 670

Glu Glu Thr Leu Ser Leu Pro Arg Asp Leu Glu Ser Leu Asp Arg Ser
        675                 680                 685

Phe Asn Gly Leu Leu Thr Met Tyr Gln Arg Lys Arg Glu Gln Phe Glu
    690                 695                 700

Lys Ile Ser Ser Ala Asp Pro Ser Gly Ala Phe Arg Met Leu Ser Thr
705                 710                 715                 720

Ala Tyr Glu Gln Ser Ala Gln Ala Ala Gln Gln Val Ser Asp Ser Ser
                725                 730                 735

Arg Leu Leu Asp Gln Leu Arg Asp Ser Arg Arg Glu Ala Glu Arg Leu
            740                 745                 750

Val Arg Gln Ala Gly Gly Gly Gly Gly Thr Gly Ser Pro Lys Leu Val
        755                 760                 765

Ala Leu Arg Leu Glu Met Ser Ser Leu Pro Asp Leu Thr Pro Thr Phe
    770                 775                 780

Asn Lys Leu Cys Gly Asn Ser Arg Gln Met Ala Cys Thr Pro Ile Ser
785                 790                 795                 800

Cys Pro Gly Glu Leu Cys Pro Gln Asp Asn Gly Thr Ala Cys Gly Ser
                805                 810                 815

Arg Cys Arg Gly Val Leu Pro Arg Ala Gly Gly Ala Phe Leu Met Ala
            820                 825                 830

Gly Gln Val Ala Glu Gln Leu Arg Gly Phe Asn Ala Gln Leu Gln Arg
        835                 840                 845

Thr Arg Gln Met Ile Arg Ala Ala Glu Glu Ser Ala Ser Gln Ile Gln
    850                 855                 860

Ser Ser Ala Gln Arg Leu Glu Thr Gln Val Ser Ala Ser Arg Ser Gln
865                 870                 875                 880

Met Glu Glu Asp Val Arg Arg Thr Arg Leu Leu Ile Gln Gln Val Arg
                885                 890                 895

Asp Phe Leu Thr Asp Pro Asp Thr Asp Ala Ala Thr Ile Gln Glu Val
            900                 905                 910

Ser Glu Ala Val Leu Ala Leu Trp Leu Pro Thr Asp Ser Ala Thr Val
        915                 920                 925

Leu Gln Lys Met Asn Glu Ile Gln Ala Ile Ala Ala Arg Leu Pro Asn
    930                 935                 940

Val Asp Leu Val Leu Ser Gln Thr Lys Gln Asp Ile Ala Arg Ala Arg
945                 950                 955                 960

Arg Leu Gln Ala Glu Ala Glu Glu Ala Arg Ser Arg Ala His Ala Val
                965                 970                 975

Glu Gly Gln Val Glu Asp Val Val Gly Asn Leu Arg Gln Gly Thr Val
            980                 985                 990

Ala Leu Gln Glu Ala Gln Asp Thr Met Gln Gly Thr Ser Arg Ser Leu
        995                 1000                1005

Arg Leu Ile Gln Asp Arg Val Ala Glu Val Gln Gln Val Leu Arg Pro
    1010                1015                1020

Ala Glu Lys Leu Val Thr Ser Met Thr Lys Gln Leu Gly Asp Phe Trp
1025                1030                1035                1040

Thr Arg Met Glu Glu Leu Arg His Gln Ala Arg Gln Gln Gly Ala Glu
                1045                1050                1055

Ala Val Gln Ala Gln Gln Leu Ala Glu Gly Ala Ser Glu Gln Ala Leu
```

-continued

```
        1060                1065                1070

Ser Ala Gln Glu Gly Phe Glu Arg Ile Lys Gln Lys Tyr Ala Glu Leu
    1075                1080                1085

Lys Asp Arg Leu Gly Gln Ser Ser Met Leu Gly Glu Gln Gly Ala Arg
  1090                1095                1100

Ile Gln Ser Val Lys Thr Glu Ala Glu Glu Leu Phe Gly Glu Thr Met
1105                1110                1115                1120

Glu Met Met Asp Arg Met Lys Asp Met Glu Leu Glu Leu Leu Arg Gly
            1125                1130                1135

Ser Gln Ala Ile Met Leu Arg Ser Ala Asp Leu Thr Gly Leu Glu Lys
        1140                1145                1150

Arg Val Glu Gln Ile Arg Asp His Ile Asn Gly Arg Val Leu Tyr Tyr
    1155                1160                1165

Ala Thr Cys Lys
  1170


<210> SEQ ID NO 5
<211> LENGTH: 3582
<212> TYPE: DNA
<213> ORGANISM: Homo sapiens

<400> SEQUENCE: 5

atgcctgcgc tctggctggg ctgctgcctc tgcttctcgc tcctcctgcc cgcagcccgg      60

gccacctcca ggagggaagt ctgtgattgc aatgggaagt ccaggcagtg tatctttgat     120

cgggaacttc acagacaaac tggtaatgga ttccgctgcc tcaactgcaa tgacaacact     180

gatggcattc actgcgagaa gtgcaagaat ggcttttacc ggcacagaga aagggaccgc     240

tgtttgccct gcaattgtaa ctccaaaggg tctcttagtg ctcgatgtga caactccgga     300

cggtgcagct gtaaaccagg tgtgacagga gccagatgcg accgatgtct gccaggcttc     360

cacatgctca cggatgcggg gtgcacccaa gaccagagac tgctagactc caagtgtgac     420

tgtgacccag ctggcatcgc agggccctgt gacgcgggcc gctgtgtctg caagccagcc     480

gtcactggag aacgctgtga taggtgtcga tcaggttact ataatctgga tgggggggaac     540

cctgagggct gtacccagtg tttctgctat gggcattcag ccagctgccg cagctctgca     600

gaatacagtg tccataagat cacctctacc tttcatcaag atgttgatgg ctggaaggct     660

gtccaacgaa atgggtctcc tgcaaagctc caatggtcac agcgccatca agatgtgttt     720

agctcagccc aacgactaga ccctgtctat tttgtggctc ctgccaaatt tcttgggaat     780

caacaggtga gctatggtca aagcctgtcc tttgactacc gtgtggacag aggaggcaga     840

cacccatctg cccatgatgt gattctggaa ggtgctggtc tacggatcac agctcccttg     900

atgccacttg gcaagacact gccttgtggg ctcaccaara cttacacatt caggttaaat     960

gagcatccaa gcaataattg gagcccccag ctgagttact ttgagtatcg aaggttactg    1020

cggaatctca cagccctccg catccgagct acatatggag aatacagtac tgggtacatt    1080

gacaatgtga ccctgatttc agcccgccct gtctctggag ccccagcacc ctgggttgaa    1140

cagtgtatat gtcctgttgg gtacaagggg caattctgcc aggattgtgc ttctggctac    1200

aagagagatt cagcgagact ggggcctttt ggcacctgta ttccttgtaa ctgtcaaggg    1260

ggagggggcct gtgatccaga cacaggagat tgttattcag gggatgagaa tcctgacatt    1320

gagtgtgctg actgcccaat tggtttctac aacgatccgc acgacccccg cagctgcaag    1380

ccatgtccct gtcataacgg gttcagctgc tcagtgatgc cggagacgga ggaggtggtg    1440

tgcaataact gccctcccgg ggtcaccggt gcccgctgtg agctctgtgc tgatggctac    1500
```

tttggggacc cctttggtga acatggccca gtgaggcctt gtcagccctg tcaatgcaac 1560
aacaatgtgg accccagtgc ctctgggaat tgtgaccggc tgacaggcag gtgtttgaag 1620
tgtatccaca acacagccgg catctactgc gaccagtgca aagcaggcta cttcggggac 1680
ccattggctc ccaacccagc agacaagtgt cgagcttgca actgtaaccc catgggctca 1740
gagcctgtag gatgtcgaag tgatggcacc tgtgtttgca agccaggatt tggtggcccc 1800
aactgtgagc atggagcatt cagctgtcca gcttgctata atcaagtgaa gattcagatg 1860
gatcagttta tgcagcagct tcagagaatg gaggccctga tttcaaaggc tcagggtggt 1920
gatggagtag tacctgatac agagctggaa ggcaggatgc agcaggctga gcaggccctt 1980
caggacattc tgagagatgc ccagatttca gaaggtgcta gcagatccct tggtctccag 2040
ttggccaagg tgaggagcca agagaacagc taccagagcc gcctggatga cctcaagatg 2100
actgtggaaa gagttcgggc tctgggaagt cagtaccaga accgagttcg ggatactcac 2160
aggctcatca ctcagatgca gctgagcctg gcagaaagtg aagcttcctt gggaaacact 2220
aacattcctg cctcagacca ctacgtgggg ccaaatggct ttaaaagtct ggctcaggag 2280
gccacaagat tagcagaaag ccacgttgag tcagccagta acatggagca actgacaagg 2340
gaaactgagg actattccaa acaagccctc tcactggtgc gcaaggccct gcatgaagga 2400
gtcggaagcg gaagcggtag cccggacggt gctgtggtgc aagggcttgt ggaaaaattg 2460
gagaaaacca agtccctggc ccagcagttg acaagggagg ccactcaagc ggaaattgaa 2520
gcagataggt cttatcagca cagtctccgc ctcctggatt cagtgtctcg gcttcaggga 2580
gtcagtgatc agtcctttca ggtggaagaa gcaaagaggh tcaaacaaaa agcggattca 2640
ctctcaagcc tggtaaccag gcatatggat gagttcaagc gtacacagaa gaatctggga 2700
aactggaaag aagaagcaca gcagctctta cagaatggaa aaagtgggag agagaaatca 2760
gatcagctgc tttcccgtgc caatcttgct aaaagcagag cacaagaagc actgagtatg 2820
ggcaatgcca ctttttatga agttgagagc atccttaaaa acctcagaga gtttgacctg 2880
caggtggaca acagaaaagc agaagctgaa gaagccatga agagactctc ctacatcagc 2940
cagaaggttt cagatgccag tgacaagacc cagcaagcag aaagagccct ggggagcgct 3000
gctgctgatg cacagagggc aaagaatggg gccggggagg ccctggaaat ctccagtgag 3060
attgaacagg agattgggag tctgaacttg gaagccaatg tgacagcaga tggagccttg 3120
gccatggaaa agggactggc ctctctgaag agtgagatga gggaagtgga aggagagctg 3180
gaaaggaagg agctggagtt tgacacgaat atggatgcag tacagatggt gattacagaa 3240
gcccagaagg ttgataccag agccaagaac gctggggtta caatccaaga cacactcaac 3300
acattagacg gcctcctgca tctgatggac cagcctctca gtgtagatga agaggggctg 3360
gtcttactgg agcagaagct ttcccgagcc aagacccaga tcaacagcca actgcggccc 3420
atgatgtcag agctggaaga gagggcacgt cagcagaggg gccacctcca tttgctggag 3480
acaagcatag atgggattct ggctgatgtg aagaacttgg agaacattag ggacaacctg 3540
cccccaggct gctacaatac ccaggctctg gagcaacagt ga 3582

<210> SEQ ID NO 6
<211> LENGTH: 1193
<212> TYPE: PRT
<213> ORGANISM: Homo sapiens
<220> FEATURE:
<221> NAME/KEY: Xaa
<222> LOCATION: 874
<223> OTHER INFORMATION: Any amino acid

<400> SEQUENCE: 6

```
Met Pro Ala Leu Trp Leu Gly Cys Cys Leu Cys Phe Ser Leu Leu Leu
1               5                   10                  15

Pro Ala Ala Arg Ala Thr Ser Arg Arg Glu Val Cys Asp Cys Asn Gly
            20                  25                  30

Lys Ser Arg Gln Cys Ile Phe Asp Arg Glu Leu His Arg Gln Thr Gly
        35                  40                  45

Asn Gly Phe Arg Cys Leu Asn Cys Asn Asp Asn Thr Asp Gly Ile His
    50                  55                  60

Cys Glu Lys Cys Lys Asn Gly Phe Tyr Arg His Arg Glu Arg Asp Arg
65                  70                  75                  80

Cys Leu Pro Cys Asn Cys Asn Ser Lys Gly Ser Leu Ser Ala Arg Cys
                85                  90                  95

Asp Asn Ser Gly Arg Cys Ser Cys Lys Pro Gly Val Thr Gly Ala Arg
            100                 105                 110

Cys Asp Arg Cys Leu Pro Gly Phe His Met Leu Thr Asp Ala Gly Cys
        115                 120                 125

Thr Gln Asp Gln Arg Leu Leu Asp Ser Lys Cys Asp Cys Asp Pro Ala
    130                 135                 140

Gly Ile Ala Gly Pro Cys Asp Ala Gly Arg Cys Val Cys Lys Pro Ala
145                 150                 155                 160

Val Thr Gly Glu Arg Cys Asp Arg Cys Arg Ser Gly Tyr Tyr Asn Leu
                165                 170                 175

Asp Gly Gly Asn Pro Glu Gly Cys Thr Gln Cys Phe Cys Tyr Gly His
            180                 185                 190

Ser Ala Ser Cys Arg Ser Ser Ala Glu Tyr Ser Val His Lys Ile Thr
        195                 200                 205

Ser Thr Phe His Gln Asp Val Asp Gly Trp Lys Ala Val Gln Arg Asn
    210                 215                 220

Gly Ser Pro Ala Lys Leu Gln Trp Ser Gln Arg His Gln Asp Val Phe
225                 230                 235                 240

Ser Ser Ala Gln Arg Leu Asp Pro Val Tyr Phe Val Ala Pro Ala Lys
                245                 250                 255

Phe Leu Gly Asn Gln Gln Val Ser Tyr Gly Gln Ser Leu Ser Phe Asp
            260                 265                 270

Tyr Arg Val Asp Arg Gly Gly Arg His Pro Ser Ala His Asp Val Ile
        275                 280                 285

Leu Glu Gly Ala Gly Leu Arg Ile Thr Ala Pro Leu Met Pro Leu Gly
    290                 295                 300

Lys Thr Leu Pro Cys Gly Leu Thr Lys Thr Tyr Thr Phe Arg Leu Asn
305                 310                 315                 320

Glu His Pro Ser Asn Asn Trp Ser Pro Gln Leu Ser Tyr Phe Glu Tyr
                325                 330                 335

Arg Arg Leu Leu Arg Asn Leu Thr Ala Leu Arg Ile Arg Ala Thr Tyr
            340                 345                 350

Gly Glu Tyr Ser Thr Gly Tyr Ile Asp Asn Val Thr Leu Ile Ser Ala
        355                 360                 365

Arg Pro Val Ser Gly Ala Pro Ala Pro Trp Val Glu Gln Cys Ile Cys
    370                 375                 380

Pro Val Gly Tyr Lys Gly Gln Phe Cys Gln Asp Cys Ala Ser Gly Tyr
385                 390                 395                 400

Lys Arg Asp Ser Ala Arg Leu Gly Pro Phe Gly Thr Cys Ile Pro Cys
                405                 410                 415
```

-continued

```
Asn Cys Gln Gly Gly Gly Ala Cys Asp Pro Asp Thr Gly Asp Cys Tyr
            420                 425                 430

Ser Gly Asp Glu Asn Pro Asp Ile Glu Cys Ala Asp Cys Pro Ile Gly
        435                 440                 445

Phe Tyr Asn Asp Pro His Asp Pro Arg Ser Cys Lys Pro Cys Pro Cys
    450                 455                 460

His Asn Gly Phe Ser Cys Ser Val Met Pro Glu Thr Glu Glu Val Val
465                 470                 475                 480

Cys Asn Asn Cys Pro Pro Gly Val Thr Gly Ala Arg Cys Glu Leu Cys
                485                 490                 495

Ala Asp Gly Tyr Phe Gly Asp Pro Phe Gly Glu His Gly Pro Val Arg
            500                 505                 510

Pro Cys Gln Pro Cys Gln Cys Asn Asn Asn Val Asp Pro Ser Ala Ser
        515                 520                 525

Gly Asn Cys Asp Arg Leu Thr Gly Arg Cys Leu Lys Cys Ile His Asn
    530                 535                 540

Thr Ala Gly Ile Tyr Cys Asp Gln Cys Lys Ala Gly Tyr Phe Gly Asp
545                 550                 555                 560

Pro Leu Ala Pro Asn Pro Ala Asp Lys Cys Arg Ala Cys Asn Cys Asn
                565                 570                 575

Pro Met Gly Ser Glu Pro Val Gly Cys Arg Ser Asp Gly Thr Cys Val
            580                 585                 590

Cys Lys Pro Gly Phe Gly Gly Pro Asn Cys Glu His Gly Ala Phe Ser
        595                 600                 605

Cys Pro Ala Cys Tyr Asn Gln Val Lys Ile Gln Met Asp Gln Phe Met
    610                 615                 620

Gln Gln Leu Gln Arg Met Glu Ala Leu Ile Ser Lys Ala Gln Gly Gly
625                 630                 635                 640

Asp Gly Val Val Pro Asp Thr Glu Leu Glu Gly Arg Met Gln Gln Ala
                645                 650                 655

Glu Gln Ala Leu Gln Asp Ile Leu Arg Asp Ala Gln Ile Ser Glu Gly
            660                 665                 670

Ala Ser Arg Ser Leu Gly Leu Gln Leu Ala Lys Val Arg Ser Gln Glu
        675                 680                 685

Asn Ser Tyr Gln Ser Arg Leu Asp Asp Leu Lys Met Thr Val Glu Arg
    690                 695                 700

Val Arg Ala Leu Gly Ser Gln Tyr Gln Asn Arg Val Arg Asp Thr His
705                 710                 715                 720

Arg Leu Ile Thr Gln Met Gln Leu Ser Leu Ala Glu Ser Glu Ala Ser
                725                 730                 735

Leu Gly Asn Thr Asn Ile Pro Ala Ser Asp His Tyr Val Gly Pro Asn
            740                 745                 750

Gly Phe Lys Ser Leu Ala Gln Glu Ala Thr Arg Leu Ala Glu Ser His
        755                 760                 765

Val Glu Ser Ala Ser Asn Met Glu Gln Leu Thr Arg Glu Thr Glu Asp
    770                 775                 780

Tyr Ser Lys Gln Ala Leu Ser Leu Val Arg Lys Ala Leu His Glu Gly
785                 790                 795                 800

Val Gly Ser Gly Ser Gly Ser Pro Asp Gly Ala Val Val Gln Gly Leu
                805                 810                 815

Val Glu Lys Leu Glu Lys Thr Lys Ser Leu Ala Gln Gln Leu Thr Arg
            820                 825                 830

Glu Ala Thr Gln Ala Glu Ile Glu Ala Asp Arg Ser Tyr Gln His Ser
```

-continued

```
        835                 840                 845

Leu Arg Leu Leu Asp Ser Val Ser Arg Leu Gln Gly Val Ser Asp Gln
    850                 855                 860

Ser Phe Gln Val Glu Glu Ala Lys Arg Xaa Lys Gln Lys Ala Asp Ser
865                 870                 875                 880

Leu Ser Ser Leu Val Thr Arg His Met Asp Glu Phe Lys Arg Thr Gln
                885                 890                 895

Lys Asn Leu Gly Asn Trp Lys Glu Glu Ala Gln Gln Leu Leu Gln Asn
            900                 905                 910

Gly Lys Ser Gly Arg Glu Lys Ser Asp Gln Leu Leu Ser Arg Ala Asn
        915                 920                 925

Leu Ala Lys Ser Arg Ala Gln Glu Ala Leu Ser Met Gly Asn Ala Thr
    930                 935                 940

Phe Tyr Glu Val Glu Ser Ile Leu Lys Asn Leu Arg Glu Phe Asp Leu
945                 950                 955                 960

Gln Val Asp Asn Arg Lys Ala Glu Ala Glu Glu Ala Met Lys Arg Leu
                965                 970                 975

Ser Tyr Ile Ser Gln Lys Val Ser Asp Ala Ser Asp Lys Thr Gln Gln
            980                 985                 990

Ala Glu Arg Ala Leu Gly Ser Ala Ala Ala Asp Ala Gln Arg Ala Lys
        995                 1000                1005

Asn Gly Ala Gly Glu Ala Leu Glu Ile Ser Ser Glu Ile Glu Gln Glu
   1010                 1015                1020

Ile Gly Ser Leu Asn Leu Glu Ala Asn Val Thr Ala Asp Gly Ala Leu
1025                1030                1035                1040

Ala Met Glu Lys Gly Leu Ala Ser Leu Lys Ser Glu Met Arg Glu Val
               1045                1050                1055

Glu Gly Glu Leu Glu Arg Lys Glu Leu Glu Phe Asp Thr Asn Met Asp
           1060                1065                1070

Ala Val Gln Met Val Ile Thr Glu Ala Gln Lys Val Asp Thr Arg Ala
       1075                1080                1085

Lys Asn Ala Gly Val Thr Ile Gln Asp Thr Leu Asn Thr Leu Asp Gly
   1090                1095                1100

Leu Leu His Leu Met Asp Gln Pro Leu Ser Val Asp Glu Glu Gly Leu
1105                1110                1115                1120

Val Leu Leu Glu Gln Lys Leu Ser Arg Ala Lys Thr Gln Ile Asn Ser
               1125                1130                1135

Gln Leu Arg Pro Met Met Ser Glu Leu Glu Glu Arg Ala Arg Gln Gln
           1140                1145                1150

Arg Gly His Leu His Leu Leu Glu Thr Ser Ile Asp Gly Ile Leu Ala
       1155                1160                1165

Asp Val Lys Asn Leu Glu Asn Ile Arg Asp Asn Leu Pro Pro Gly Cys
   1170                1175                1180

Tyr Asn Thr Gln Ala Leu Glu Gln Gln
1185                1190
```

<210> SEQ ID NO 7
<211> LENGTH: 8832
<212> TYPE: DNA
<213> ORGANISM: Homo sapiens

<400> SEQUENCE: 7

```
atggcggcgg ccgcgcggcc tcggggtcgg gcactggggc cagtactgcc gccgacgccg      60

ctgctcctgc tggtactgcg ggtgctgcca gcctgcgggg cgaccgctcg ggatcccggg     120
```

-continued

```
gccgcggccg ggctcagcct tcacccgact tacttcaacc tggccgaggc ggcgaggatt    180
tgggccaccg ccacctgcgg ggagagggga cccggcgagg ggaggcccca gcccgagctc    240
tactgcaagt tggtcggggg ccccaccgcc ccaggcagcg gccacaccat ccagggccag    300
ttctgtgact attgcaattc tgaagacccc aggaaagcac atcctgtcac caatgccatc    360
gatggatctg aacgttggtg gcaaagccct cccctgtcct caggcacaca gtacaacaga    420
gtcaacctca ccttggatct ggggcagctc ttccatgtgg cctatatttt aatcaaattt    480
gcaaattctc ctcgccctga tctttgggtc ttggaaagat ctgtagactt tggaagcacc    540
tactcaccat ggcaatattt tgctcattct aaagtagact gtttaaaaga atttgggcgg    600
gaggcaaata tggctgtcac ccgggatgat gatgtacttt gtgttactga atattcccgt    660
attgtacctt tggaaaatgg tgaggttgtg gtgtccttga taaacggtcg tccaggtgca    720
aaaaatttta ctttctctca caccctgagg gagtttacca aggcaacaaa catccgcttg    780
cgttttctta gaaccaatac gcttcttgga cacctcatct ccaaagccca gcgagatcca    840
actgtcactc ggcggtatta ttacagcata aaggacatca gcattggtgg gcagtgtgtt    900
tgcaatggcc atgctgaagt gtgcaatata aacaatcctg aaaaactgtt tcggtgtgaa    960
tgccagcacc acacctgtgg ggagacgtgt gatcgctgct gcacagggta caatcagagg   1020
cgctggcggc ccgccgcttg ggagcagagc cacgagtgtg aagcatgcaa ctgccacggc   1080
catgccagca actgttacta tgatccagat gttgagcggc agcaggcaag cttgaatacc   1140
cagggcatct atgctggtgg aggggtctgc attaactgtc agcacaacac agctggagta   1200
aactgtgaac agtgtgctaa gggctattac cgcccttatg ggttccagt ggatgcccct   1260
gatggctgca tcccctgcag ctgtgaccct gagcatgcgg atggctgtga acagggttca   1320
ggccgctgtc actgcaagcc aaatttccac ggagacaact gtgagaagtg tgcaattgga   1380
tactacaatt tcccattttg cttgagaatt cccatttttc ctgtttctac accaagttca   1440
gaagatccag tagctggaga tataaaaggg tgtgactgta atctggaagg tgttctccct   1500
gaaatatgtg atgcccacgg acggtgcctg tgccgccctg ggttgaggg ccctcgatgt   1560
gatacctgcc gctctggttt ctactcattc cctatttgcc aagcctgctg gtgttcagcc   1620
cttggatcct accagatgcc ctgcagctca gtgactggac agtgtgaatg tcggccagga   1680
gttacaggac agcggtgtga caggtgtctc tcaggagctt atgatttccc ccactgccaa   1740
ggttccagca gtgcttgtga cccagctggt accatcaact ccaatttggg gtattgccaa   1800
tgcaagcttc atgttgaagg tcctacttgt agccgctgca aactgttata ttggaatctg   1860
gacaaagaaa accccagtgg atgttcagaa tgcaagtgcc ataaggcggg aacagtgagt   1920
ggaactggag agtgtaggca gggagatggt gactgtcact gcaagtccca tgtgggtggc   1980
gattcctgcg acacctgtga agatggatat tttgctttgg aaaagagcaa ttactttggg   2040
tgtcaagggt gtcagtgtga cattggtggg gcattgtcct ccatgtgcag tgggccctcg   2100
ggagtgtgcc agtgccgaga gcatgtcgtg ggaaaggtgt gccagcggcc tgaaaacaac   2160
tactatttcc cagatttgca tcatatgaag tatgagattg aagacggcag cacacctaat   2220
gggagagacc ttcgatttgg atttgatccg ctggcatttc ctgagtttag ctggagagga   2280
tatgcccaaa tgacctcagt acagaatgat gtaagaataa cattgaatgt agggaagtca   2340
agtggctcct tgtttcgtgt tattctgaga tacgttaacc ctggaactga agcagtatct   2400
ggccatataa ctatttatcc atcctggggt gctgctcaaa gcaaagagat catcttcctg   2460
ccgagtaagg agccagcctt tgtcactgtc cctggaaatg gttttgcaga cccattttca   2520
```

-continued

```
atcacaccag gaatatgggt tgcttgtatt aaggcagaag gagtccttct ggattacctg   2580
gtgctgctcc ccagggacta ctatgaagcc tctgtactgc agctgccagt cacagaacca   2640
tgtgcctacg caggacctcc ccaagaaaat tgcttactct accagcattt gccagtgacc   2700
agattcccct gtaccctggc ttgtgaggcc agacacttcc tgcttgatgg ggagccaaga   2760
cccgtggcag tgaggcagcc cacacctgca caccctgtca tggtggacct cagcgggaga   2820
gaggtggaat tgcatctgcg gctgcgcatc ccacaggttg gccactacgt ggttgtggtc   2880
gagtattcca cggaggcagc tcagctgttt gtggttgatg tgaatgtgaa gagctccggg   2940
tctgttctgg caggccaggt gaacatttac agctgcaact acagtgttct ctgccggagt   3000
gctgtgattg atcacatgag ccgcatcgcc atgtatgagc tattggcaga tgcagacatt   3060
cagctcaagg gacacatggc ccgattcctt ctgcatcaag tttgtatcat acctattgaa   3120
gaattctcag ctgagtatgt gagaccacaa gtccactgca ttgccagtta tgggcgattt   3180
gtcaatcaaa gtgccacctg tgtctccttg gcccatgaaa ctcctccaac agcattaatt   3240
ttggatgttc taagtggcag gcctttccct cacctgcccc agcagtcgtc accttctgtt   3300
gatgttcttc ctggggtcac cttgaaggca ccgcagaatc aagtgaccct gagaggacgt   3360
gtaccacacc tgggccgata cgtctttgtc atccattttt accaagcagc gcacccgacg   3420
tttcccgcgc aggtgtcggt ggatggcggg tggccacggg caggctcctt ccatgcctct   3480
ttttgccccc atgtgcttgg ctgccgggat caagtgattg ccgaaggcca gattgagttt   3540
gacatctcag agcctgaagt ggccgcaact gtgaaggttc cagaaggaaa gtccttggtt   3600
ttggtccgtg ttctagtggt gcctgcagaa aactatgact accaaatact tcacaaaaaa   3660
tccatggaca agtcactcga gtttatcacc aattgtggaa aaaacagctt ttaccttgac   3720
ccccagacag cctccagatt ctgtaagaat tccgccaggt ccctggtggc cttttaccac   3780
aagggcgccc tgccttgtga gtgccacccc actggggcca ccggccctca ctgcagccct   3840
gagggtgggc agtgcccatg ccagcccaac gtcatcgggc ggcagtgcac ccgctgtgca   3900
acaggccact acggattccc acgctgcaag ccgtgcagct gtggtcggcg cctttgtgaa   3960
gagatgacgg ggcagtgccg ctgccctccc cgcacggtca ggccccagtg tgaggtgtgt   4020
gagacacact cattcagctt ccaccccatg gccggctgcg aaggctgcaa ctgttccagg   4080
aggggcacca tcgaggctgc catgccggag tgtgaccggg acagcgggca gtgcagatgc   4140
aagcccagaa tcacagggcg gcagtgtgac cgatgtgctt ccgggtttta ccgctttcct   4200
gagtgtgttc cctgcaattg caacagagat gggactgagc caggagtgtg tgacccaggg   4260
accggggctt gcctctgcaa ggaaaatgta gaaggcacag agtgtaatgt gtgtcgagaa   4320
ggctcattcc atttggaccc agccaatctc aagggttgta ccagctgttt ctgttttgga   4380
gtaaataatc aatgtcacag ctcacataag cgaaggacta agtttgtgga tatgctgggc   4440
tggcacctgg agacagcaga cagagtggac atccctgtct ctttcaaccc aggcagcaac   4500
agtatggtgg cggatctcca ggagctgccc gcaaccatcc acagcgcgtc ctgggtcgca   4560
cccacctcct acctggggga caaggtttct tcatatggtg gttacctcac ttaccaagcc   4620
aagtcctttg gcttgcctgg cgacatggtt cttctggaaa agaagccgga tgtacagctc   4680
actggtcagc acatgtccat catctatgag gagacaaaca ccccacggcc agaccggctg   4740
catcatggac gagtgcacgt ggtcgaggga aacttcagac atgccagcag ccgtgcccca   4800
gtgtctaggg aggagctgat gacagtgctg tctagactgg cagatgtgcg catccaaggc   4860
ctctacttca cagagactca aaggctcacc ctgagcgagg tggggctaga ggaagcctct   4920
```

-continued

```
gacacaggaa gtgggcgcat agcacttgct gtggaaatct gtgcctgccc ccctgcctac   4980
gctggtgact cttgtcaggg ttgtagccct ggatactatc gggatcataa aggcttgtat   5040
accggacggt gtgttccctg caattgcaac ggacattcaa atcaatgcca ggatggctca   5100
ggcatatgtg ttaactgtca gcacaacacc gcgggagagc actgtgaacg ctgccaggag   5160
ggctactatg gcaacgccgt ccacggatcc tgcagggcct gcccatgtcc tcacactaac   5220
agctttgcca ctggctgtgt ggtgaatggg ggagacgtgc ggtgctcctg caaagctggg   5280
tacacaggaa cacagtgtga aaggtgtgca ccgggatatt tcgggaatcc ccagaaattc   5340
ggaggtagct gccaaccatg cagttgtaac agcaatggcc agctgggcag ctgtcatccc   5400
ctgactggag actgcataaa ccaagaaccc aaagatagca gccctgcaga agaatgtgat   5460
gattgcgaca gctgtgtgat gaccctcctg aacgacctgg ccaccatggg cgagcagctc   5520
cgcctggtca agtctcagct gcagggcctg agtgccagcg cagggcttct ggagcagatg   5580
aggcacatgg agacccaggc caaggacctg aggaatcagt tgctcaacta ccgttctgcc   5640
atttcaaatc atggatcaaa aatagaaggc ctggaaagag aactgactga tttgaatcaa   5700
gaatttgaga ctttgcaaga aaaggctcaa gtaaattcca gaaaagcaca aacattaaac   5760
aacaatgtta atcgggcaac acaaagcgca aaagaactgg atgtgaagat taaaaatgtc   5820
atccggaatg tgcacattct tttaaagcag atctctggga cagatggaga gggaaacaac   5880
gtgccttcag gtgacttttc cagagagtgg gctgaagccc agcgcatgat gagggaactg   5940
cggaacagga actttggaaa gcacctcaga gaagcagaag ctgataaaag ggagtcgcag   6000
ctcttgctga accggataag gacctggcag aaaacccacc aggggggagaa caatgggctt   6060
gctaacagta tccgggattc tttaaatgaa tacgaagcca aactcagtga ccttcgtgct   6120
cggctgcagg aggcagctgc ccaagccaag caggcaaatg gcttgaacca agaaaacgag   6180
agagctttgg gagccattca gagacaagtg aaagaaataa attccctgca gagtgatttc   6240
accaagtatc taaccactgc agactcatct ttgttgcaaa ccaacattgc gctgcagctg   6300
atggagaaaa gccagaagga atatgaaaaa ttagctgcca gtttaaatga agcaagacaa   6360
gaactaagtg acaaagtaag agaactttcc agatctgctg gcaaaacatc ccttgtggag   6420
gaggcagaaa agcacgcgcg gtccttacaa gagctggcaa agcagctgga agagatcaag   6480
agaaacgcca gcggggatga gctggtgcgc tgtgctgtgg atgccgccac cgcctacgag   6540
aacatcctca atgccatcaa agcggccgag gacgcagcca acagggctgc cagtgcatct   6600
gaatctgccc tccagacagt gataaaggaa gatctgccaa gaaaagctaa aaccctgagt   6660
tccaacagtg ataaactgtt aaatgaagcc aagatgacac aaaagaagct aaagcaagaa   6720
gtcagtccag ctctcaacaa cctacagcaa accctgaata ttgtgacagt tcagaaagaa   6780
gtgatagaca ccaatctcac aactctccga gatggtcttc atgggataca gagaggtgat   6840
attgatgcta tgatcagtag tgcaaagagc atggtcagaa aggccaacga catcacagat   6900
gaggttctgg atgggctcaa ccccatccag acagatgtgg aaagaattaa ggacacctat   6960
gggaggacac agaacgaaga cttcaaaaag gctctgactg atgcagataa ctcggtgaat   7020
aagttaacca acaaactacc tgatctttgg cgcaagattg aaagtatcaa ccaacagctg   7080
ttgcccttgg gaaacatctc tgacaacatg gacagaatac gagaactaat tcagcaggcc   7140
agagatgctg ccagtaaggt tgctgtcccc atgaggttca atggtaaatc tggagtcgaa   7200
gtccgactgc caaatgacct ggaagatttg aaaggatata catctctgtc cttgtttctc   7260
caaaggccca actcaagaga aaatgggggt actgagaata tgtttgtgat gtaccttgga   7320
```

-continued

```
aataaagatg cctcccggga ctacatcggc atggcagttg tggatggcca gctcacctgt   7380

gtctacaacc tgggggaccg tgaggctgaa ctccaagtgg accagatctt gaccaagagt   7440

gagactaagg aggcagttat ggatcgggtg aaatttcaga gaatttatca gtttgcaagg   7500

cttaattaca ccaaaggagc cacatccagt aaaccagaaa cacccggagt ctatgacatg   7560

gatggtagaa atagcaatac actccttaat ttggatcctg aaaatgttgt attttatgtt   7620

ggaggttacc cacctgattt taaacttccc agtcgactaa gtttccctcc atacaaaggt   7680

tgtattgaat tagatgacct caatgaaaat gttctgagct tgtacaactt caaaaaaaca   7740

ttcaatctca acacaactga agtggagcct tgtagaagga ggaaggaaga gtcagacaaa   7800

aattattttg aaggtacggg ctatgctcga gttccaactc aaccacatgc tcccatccca   7860

acctttggac agacaattca gaccaccgtg gatagaggct tgctgttctt tgcagaaaac   7920

ggggatcgct tcatatctct aaatatagaa gatggcaagc tcatggtgag atacaaactg   7980

aattcagagc taccaaaaga gagaggagtt ggagacgcca taaacaacgg cagagaccat   8040

tcgattcaga tcaaaattgg aaaactccaa aagcgtatgt ggataaatgt ggacgttcaa   8100

aacactataa ttgatggtga agtatttgat ttcagcacat attatctggg aggaattcca   8160

attgcaatca gggaaagatt taacatttct acgcctgctt tccgaggctg catgaaaaat   8220

ttgaagaaaa ccagtggtgt cgttagattg aatgatactg tgggagtaac caaaaagtgc   8280

tcggaagact ggaagcttgt gcgatctgcc tcattctcca gaggaggaca attgagtttc   8340

actgatttgg gcttaccacc tactgaccac ctccaggcct catttggatt tcagaccttt   8400

caacccagtg gcatattatt agatcatcag acatggacaa ggaacctgca ggtcactctg   8460

gaagatggtt acattgaatt gagcaccagc gatagcggcg gcccaatttt taaatctcca   8520

cagacgtata tggatggttt actgcattat gtatctgtaa taagcgacaa ctctggacta   8580

cggcttctca tcgatgacca gcttctgaga aatagcaaaa ggctaaaaca catttcaagt   8640

tcccggcagt ctctgcgtct gggcgggagc aattttgagg gttgtattag caatgttttt   8700

gtccagaggt tatcactgag tcctgaagtc ctagatttga ccagtaactc tctcaagaga   8760

gatgtgtccc tgggaggctg cagtttaaac aaaccacctt ttctaatgtt gcttaaaggt   8820

tctaccaggt tt                                                       8832
```

<210> SEQ ID NO 8
<211> LENGTH: 2944
<212> TYPE: PRT
<213> ORGANISM: Homo sapiens

<400> SEQUENCE: 8

```
Met Ala Ala Ala Ala Arg Pro Arg Gly Arg Ala Leu Gly Pro Val Leu
1               5                   10                  15

Pro Pro Thr Pro Leu Leu Leu Leu Val Leu Arg Val Leu Pro Ala Cys
            20                  25                  30

Gly Ala Thr Ala Arg Asp Pro Gly Ala Ala Ala Gly Leu Ser Leu His
        35                  40                  45

Pro Thr Tyr Phe Asn Leu Ala Glu Ala Ala Arg Ile Trp Ala Thr Ala
    50                  55                  60

Thr Cys Gly Glu Arg Gly Pro Gly Glu Gly Arg Pro Gln Pro Glu Leu
65                  70                  75                  80

Tyr Cys Lys Leu Val Gly Gly Pro Thr Ala Pro Gly Ser Gly His Thr
                85                  90                  95

Ile Gln Gly Gln Phe Cys Asp Tyr Cys Asn Ser Glu Asp Pro Arg Lys
            100                 105                 110
```

```
Ala His Pro Val Thr Asn Ala Ile Asp Gly Ser Glu Arg Trp Trp Gln
        115                 120                 125

Ser Pro Pro Leu Ser Ser Gly Thr Gln Tyr Asn Arg Val Asn Leu Thr
    130                 135                 140

Leu Asp Leu Gly Gln Leu Phe His Val Ala Tyr Ile Leu Ile Lys Phe
145                 150                 155                 160

Ala Asn Ser Pro Arg Pro Asp Leu Trp Val Leu Glu Arg Ser Val Asp
                165                 170                 175

Phe Gly Ser Thr Tyr Ser Pro Trp Gln Tyr Phe Ala His Ser Lys Val
            180                 185                 190

Asp Cys Leu Lys Glu Phe Gly Arg Glu Ala Asn Met Ala Val Thr Arg
        195                 200                 205

Asp Asp Asp Val Leu Cys Val Thr Glu Tyr Ser Arg Ile Val Pro Leu
    210                 215                 220

Glu Asn Gly Glu Val Val Val Ser Leu Ile Asn Gly Arg Pro Gly Ala
225                 230                 235                 240

Lys Asn Phe Thr Phe Ser His Thr Leu Arg Glu Phe Thr Lys Ala Thr
                245                 250                 255

Asn Ile Arg Leu Arg Phe Leu Arg Thr Asn Thr Leu Leu Gly His Leu
            260                 265                 270

Ile Ser Lys Ala Gln Arg Asp Pro Thr Val Thr Arg Arg Tyr Tyr Tyr
        275                 280                 285

Ser Ile Lys Asp Ile Ser Ile Gly Gly Gln Cys Val Cys Asn Gly His
    290                 295                 300

Ala Glu Val Cys Asn Ile Asn Asn Pro Glu Lys Leu Phe Arg Cys Glu
305                 310                 315                 320

Cys Gln His His Thr Cys Gly Glu Thr Cys Asp Arg Cys Cys Thr Gly
                325                 330                 335

Tyr Asn Gln Arg Arg Trp Arg Pro Ala Ala Trp Glu Gln Ser His Glu
            340                 345                 350

Cys Glu Ala Cys Asn Cys His Gly His Ala Ser Asn Cys Tyr Tyr Asp
        355                 360                 365

Pro Asp Val Glu Arg Gln Gln Ala Ser Leu Asn Thr Gln Gly Ile Tyr
    370                 375                 380

Ala Gly Gly Gly Val Cys Ile Asn Cys Gln His Asn Thr Ala Gly Val
385                 390                 395                 400

Asn Cys Glu Gln Cys Ala Lys Gly Tyr Tyr Arg Pro Tyr Gly Val Pro
                405                 410                 415

Val Asp Ala Pro Asp Gly Cys Ile Pro Cys Ser Cys Asp Pro Glu His
            420                 425                 430

Ala Asp Gly Cys Glu Gln Gly Ser Gly Arg Cys His Cys Lys Pro Asn
        435                 440                 445

Phe His Gly Asp Asn Cys Glu Lys Cys Ala Ile Gly Tyr Tyr Asn Phe
    450                 455                 460

Pro Phe Cys Leu Arg Ile Pro Ile Phe Pro Val Ser Thr Pro Ser Ser
465                 470                 475                 480

Glu Asp Pro Val Ala Gly Asp Ile Lys Gly Cys Asp Cys Asn Leu Glu
                485                 490                 495

Gly Val Leu Pro Glu Ile Cys Asp Ala His Gly Arg Cys Leu Cys Arg
            500                 505                 510

Pro Gly Val Glu Gly Pro Arg Cys Asp Thr Cys Arg Ser Gly Phe Tyr
        515                 520                 525

Ser Phe Pro Ile Cys Gln Ala Cys Trp Cys Ser Ala Leu Gly Ser Tyr
```

-continued

```
    530                 535                 540

Gln Met Pro Cys Ser Ser Val Thr Gly Gln Cys Glu Cys Arg Pro Gly
545                 550                 555                 560

Val Thr Gly Gln Arg Cys Asp Arg Cys Leu Ser Gly Ala Tyr Asp Phe
                565                 570                 575

Pro His Cys Gln Gly Ser Ser Ser Ala Cys Asp Pro Ala Gly Thr Ile
            580                 585                 590

Asn Ser Asn Leu Gly Tyr Cys Gln Cys Lys Leu His Val Glu Gly Pro
        595                 600                 605

Thr Cys Ser Arg Cys Lys Leu Leu Tyr Trp Asn Leu Asp Lys Glu Asn
    610                 615                 620

Pro Ser Gly Cys Ser Glu Cys Lys Cys His Lys Ala Gly Thr Val Ser
625                 630                 635                 640

Gly Thr Gly Glu Cys Arg Gln Gly Asp Gly Asp Cys His Cys Lys Ser
                645                 650                 655

His Val Gly Gly Asp Ser Cys Asp Thr Cys Glu Asp Gly Tyr Phe Ala
            660                 665                 670

Leu Glu Lys Ser Asn Tyr Phe Gly Cys Gln Gly Cys Gln Cys Asp Ile
        675                 680                 685

Gly Gly Ala Leu Ser Ser Met Cys Ser Gly Pro Ser Gly Val Cys Gln
    690                 695                 700

Cys Arg Glu His Val Val Gly Lys Val Cys Gln Arg Pro Glu Asn Asn
705                 710                 715                 720

Tyr Tyr Phe Pro Asp Leu His His Met Lys Tyr Glu Ile Glu Asp Gly
                725                 730                 735

Ser Thr Pro Asn Gly Arg Asp Leu Arg Phe Gly Phe Asp Pro Leu Ala
            740                 745                 750

Phe Pro Glu Phe Ser Trp Arg Gly Tyr Ala Gln Met Thr Ser Val Gln
        755                 760                 765

Asn Asp Val Arg Ile Thr Leu Asn Val Gly Lys Ser Ser Gly Ser Leu
    770                 775                 780

Phe Arg Val Ile Leu Arg Tyr Val Asn Pro Gly Thr Glu Ala Val Ser
785                 790                 795                 800

Gly His Ile Thr Ile Tyr Pro Ser Trp Gly Ala Ala Gln Ser Lys Glu
                805                 810                 815

Ile Ile Phe Leu Pro Ser Lys Glu Pro Ala Phe Val Thr Val Pro Gly
            820                 825                 830

Asn Gly Phe Ala Asp Pro Phe Ser Ile Thr Pro Gly Ile Trp Val Ala
        835                 840                 845

Cys Ile Lys Ala Glu Gly Val Leu Leu Asp Tyr Leu Val Leu Leu Pro
    850                 855                 860

Arg Asp Tyr Tyr Glu Ala Ser Val Leu Gln Leu Pro Val Thr Glu Pro
865                 870                 875                 880

Cys Ala Tyr Ala Gly Pro Pro Gln Glu Asn Cys Leu Leu Tyr Gln His
                885                 890                 895

Leu Pro Val Thr Arg Phe Pro Cys Thr Leu Ala Cys Glu Ala Arg His
            900                 905                 910

Phe Leu Leu Asp Gly Glu Pro Arg Pro Val Ala Val Arg Gln Pro Thr
        915                 920                 925

Pro Ala His Pro Val Met Val Asp Leu Ser Gly Arg Glu Val Glu Leu
    930                 935                 940

His Leu Arg Leu Arg Ile Pro Gln Val Gly His Tyr Val Val Val Val
945                 950                 955                 960
```

-continued

```
Glu Tyr Ser Thr Glu Ala Ala Gln Leu Phe Val Val Asp Val Asn Val
                965                 970                 975

Lys Ser Ser Gly Ser Val Leu Ala Gly Gln Val Asn Ile Tyr Ser Cys
            980                 985                 990

Asn Tyr Ser Val Leu Cys Arg Ser Ala Val Ile Asp His Met Ser Arg
        995                 1000                1005

Ile Ala Met Tyr Glu Leu Leu Ala Asp Ala Asp Ile Gln Leu Lys Gly
   1010                1015                1020

His Met Ala Arg Phe Leu Leu His Gln Val Cys Ile Ile Pro Ile Glu
1025                1030                1035                1040

Glu Phe Ser Ala Glu Tyr Val Arg Pro Gln Val His Cys Ile Ala Ser
               1045                1050                1055

Tyr Gly Arg Phe Val Asn Gln Ser Ala Thr Cys Val Ser Leu Ala His
           1060                1065                1070

Glu Thr Pro Pro Thr Ala Leu Ile Leu Asp Val Leu Ser Gly Arg Pro
       1075                1080                1085

Phe Pro His Leu Pro Gln Gln Ser Ser Pro Ser Val Asp Val Leu Pro
   1090                1095                1100

Gly Val Thr Leu Lys Ala Pro Gln Asn Gln Val Thr Leu Arg Gly Arg
1105                1110                1115                1120

Val Pro His Leu Gly Arg Tyr Val Phe Val Ile His Phe Tyr Gln Ala
               1125                1130                1135

Ala His Pro Thr Phe Pro Ala Gln Val Ser Val Asp Gly Gly Trp Pro
           1140                1145                1150

Arg Ala Gly Ser Phe His Ala Ser Phe Cys Pro His Val Leu Gly Cys
       1155                1160                1165

Arg Asp Gln Val Ile Ala Glu Gly Gln Ile Glu Phe Asp Ile Ser Glu
   1170                1175                1180

Pro Glu Val Ala Ala Thr Val Lys Val Pro Glu Gly Lys Ser Leu Val
1185                1190                1195                1200

Leu Val Arg Val Leu Val Val Pro Ala Glu Asn Tyr Asp Tyr Gln Ile
               1205                1210                1215

Leu His Lys Lys Ser Met Asp Lys Ser Leu Glu Phe Ile Thr Asn Cys
           1220                1225                1230

Gly Lys Asn Ser Phe Tyr Leu Asp Pro Gln Thr Ala Ser Arg Phe Cys
       1235                1240                1245

Lys Asn Ser Ala Arg Ser Leu Val Ala Phe Tyr His Lys Gly Ala Leu
   1250                1255                1260

Pro Cys Glu Cys His Pro Thr Gly Ala Thr Gly Pro His Cys Ser Pro
1265                1270                1275                1280

Glu Gly Gly Gln Cys Pro Cys Gln Pro Asn Val Ile Gly Arg Gln Cys
               1285                1290                1295

Thr Arg Cys Ala Thr Gly His Tyr Gly Phe Pro Arg Cys Lys Pro Cys
           1300                1305                1310

Ser Cys Gly Arg Arg Leu Cys Glu Glu Met Thr Gly Gln Cys Arg Cys
       1315                1320                1325

Pro Pro Arg Thr Val Arg Pro Gln Cys Glu Val Cys Glu Thr His Ser
   1330                1335                1340

Phe Ser Phe His Pro Met Ala Gly Cys Glu Gly Cys Asn Cys Ser Arg
1345                1350                1355                1360

Arg Gly Thr Ile Glu Ala Ala Met Pro Glu Cys Asp Arg Asp Ser Gly
               1365                1370                1375

Gln Cys Arg Cys Lys Pro Arg Ile Thr Gly Arg Gln Cys Asp Arg Cys
           1380                1385                1390
```

-continued

Ala Ser Gly Phe Tyr Arg Phe Pro Glu Cys Val Pro Cys Asn Cys Asn
1395 1400 1405

Arg Asp Gly Thr Glu Pro Gly Val Cys Asp Pro Gly Thr Gly Ala Cys
1410 1415 1420

Leu Cys Lys Glu Asn Val Glu Gly Thr Glu Cys Asn Val Cys Arg Glu
1425 1430 1435 1440

Gly Ser Phe His Leu Asp Pro Ala Asn Leu Lys Gly Cys Thr Ser Cys
1445 1450 1455

Phe Cys Phe Gly Val Asn Asn Gln Cys His Ser Ser His Lys Arg Arg
1460 1465 1470

Thr Lys Phe Val Asp Met Leu Gly Trp His Leu Glu Thr Ala Asp Arg
1475 1480 1485

Val Asp Ile Pro Val Ser Phe Asn Pro Gly Ser Asn Ser Met Val Ala
1490 1495 1500

Asp Leu Gln Glu Leu Pro Ala Thr Ile His Ser Ala Ser Trp Val Ala
1505 1510 1515 1520

Pro Thr Ser Tyr Leu Gly Asp Lys Val Ser Ser Tyr Gly Gly Tyr Leu
1525 1530 1535

Thr Tyr Gln Ala Lys Ser Phe Gly Leu Pro Gly Asp Met Val Leu Leu
1540 1545 1550

Glu Lys Lys Pro Asp Val Gln Leu Thr Gly Gln His Met Ser Ile Ile
1555 1560 1565

Tyr Glu Glu Thr Asn Thr Pro Arg Pro Asp Arg Leu His His Gly Arg
1570 1575 1580

Val His Val Val Glu Gly Asn Phe Arg His Ala Ser Ser Arg Ala Pro
1585 1590 1595 1600

Val Ser Arg Glu Glu Leu Met Thr Val Leu Ser Arg Leu Ala Asp Val
1605 1610 1615

Arg Ile Gln Gly Leu Tyr Phe Thr Glu Thr Gln Arg Leu Thr Leu Ser
1620 1625 1630

Glu Val Gly Leu Glu Glu Ala Ser Asp Thr Gly Ser Gly Arg Ile Ala
1635 1640 1645

Leu Ala Val Glu Ile Cys Ala Cys Pro Pro Ala Tyr Ala Gly Asp Ser
1650 1655 1660

Cys Gln Gly Cys Ser Pro Gly Tyr Tyr Arg Asp His Lys Gly Leu Tyr
1665 1670 1675 1680

Thr Gly Arg Cys Val Pro Cys Asn Cys Asn Gly His Ser Asn Gln Cys
1685 1690 1695

Gln Asp Gly Ser Gly Ile Cys Val Asn Cys Gln His Asn Thr Ala Gly
1700 1705 1710

Glu His Cys Glu Arg Cys Gln Glu Gly Tyr Tyr Gly Asn Ala Val His
1715 1720 1725

Gly Ser Cys Arg Ala Cys Pro Cys Pro His Thr Asn Ser Phe Ala Thr
1730 1735 1740

Gly Cys Val Val Asn Gly Gly Asp Val Arg Cys Ser Cys Lys Ala Gly
1745 1750 1755 1760

Tyr Thr Gly Thr Gln Cys Glu Arg Cys Ala Pro Gly Tyr Phe Gly Asn
1765 1770 1775

Pro Gln Lys Phe Gly Gly Ser Cys Gln Pro Cys Ser Cys Asn Ser Asn
1780 1785 1790

Gly Gln Leu Gly Ser Cys His Pro Leu Thr Gly Asp Cys Ile Asn Gln
1795 1800 1805

Glu Pro Lys Asp Ser Ser Pro Ala Glu Glu Cys Asp Asp Cys Asp Ser

-continued

```
    1810                1815                1820

Cys Val Met Thr Leu Leu Asn Asp Leu Ala Thr Met Gly Glu Gln Leu
1825                1830                1835                1840

Arg Leu Val Lys Ser Gln Leu Gln Gly Leu Ser Ala Ser Ala Gly Leu
                1845                1850                1855

Leu Glu Gln Met Arg His Met Glu Thr Gln Ala Lys Asp Leu Arg Asn
            1860                1865                1870

Gln Leu Leu Asn Tyr Arg Ser Ala Ile Ser Asn His Gly Ser Lys Ile
        1875                1880                1885

Glu Gly Leu Glu Arg Glu Leu Thr Asp Leu Asn Gln Glu Phe Glu Thr
    1890                1895                1900

Leu Gln Glu Lys Ala Gln Val Asn Ser Arg Lys Ala Gln Thr Leu Asn
1905                1910                1915                1920

Asn Asn Val Asn Arg Ala Thr Gln Ser Ala Lys Glu Leu Asp Val Lys
                1925                1930                1935

Ile Lys Asn Val Ile Arg Asn Val His Ile Leu Leu Lys Gln Ile Ser
            1940                1945                1950

Gly Thr Asp Gly Glu Gly Asn Asn Val Pro Ser Gly Asp Phe Ser Arg
        1955                1960                1965

Glu Trp Ala Glu Ala Gln Arg Met Met Arg Glu Leu Arg Asn Arg Asn
    1970                1975                1980

Phe Gly Lys His Leu Arg Glu Ala Glu Ala Asp Lys Arg Glu Ser Gln
1985                1990                1995                2000

Leu Leu Leu Asn Arg Ile Arg Thr Trp Gln Lys Thr His Gln Gly Glu
                2005                2010                2015

Asn Asn Gly Leu Ala Asn Ser Ile Arg Asp Ser Leu Asn Glu Tyr Glu
            2020                2025                2030

Ala Lys Leu Ser Asp Leu Arg Ala Arg Leu Gln Glu Ala Ala Ala Gln
        2035                2040                2045

Ala Lys Gln Ala Asn Gly Leu Asn Gln Glu Asn Glu Arg Ala Leu Gly
    2050                2055                2060

Ala Ile Gln Arg Gln Val Lys Glu Ile Asn Ser Leu Gln Ser Asp Phe
2065                2070                2075                2080

Thr Lys Tyr Leu Thr Thr Ala Asp Ser Ser Leu Leu Gln Thr Asn Ile
                2085                2090                2095

Ala Leu Gln Leu Met Glu Lys Ser Gln Lys Glu Tyr Glu Lys Leu Ala
            2100                2105                2110

Ala Ser Leu Asn Glu Ala Arg Gln Glu Leu Ser Asp Lys Val Arg Glu
        2115                2120                2125

Leu Ser Arg Ser Ala Gly Lys Thr Ser Leu Val Glu Glu Ala Glu Lys
    2130                2135                2140

His Ala Arg Ser Leu Gln Glu Leu Ala Lys Gln Leu Glu Glu Ile Lys
2145                2150                2155                2160

Arg Asn Ala Ser Gly Asp Glu Leu Val Arg Cys Ala Val Asp Ala Ala
                2165                2170                2175

Thr Ala Tyr Glu Asn Ile Leu Asn Ala Ile Lys Ala Ala Glu Asp Ala
            2180                2185                2190

Ala Asn Arg Ala Ala Ser Ala Ser Glu Ser Ala Leu Gln Thr Val Ile
        2195                2200                2205

Lys Glu Asp Leu Pro Arg Lys Ala Lys Thr Leu Ser Ser Asn Ser Asp
    2210                2215                2220

Lys Leu Leu Asn Glu Ala Lys Met Thr Gln Lys Lys Leu Lys Gln Glu
2225                2230                2235                2240
```

```
Val Ser Pro Ala Leu Asn Asn Leu Gln Gln Thr Leu Asn Ile Val Thr
                2245                2250                2255

Val Gln Lys Glu Val Ile Asp Thr Asn Leu Thr Thr Leu Arg Asp Gly
            2260                2265                2270

Leu His Gly Ile Gln Arg Gly Asp Ile Asp Ala Met Ile Ser Ser Ala
        2275                2280                2285

Lys Ser Met Val Arg Lys Ala Asn Asp Ile Thr Asp Glu Val Leu Asp
    2290                2295                2300

Gly Leu Asn Pro Ile Gln Thr Asp Val Glu Arg Ile Lys Asp Thr Tyr
2305                2310                2315                2320

Gly Arg Thr Gln Asn Glu Asp Phe Lys Lys Ala Leu Thr Asp Ala Asp
                2325                2330                2335

Asn Ser Val Asn Lys Leu Thr Asn Lys Leu Pro Asp Leu Trp Arg Lys
            2340                2345                2350

Ile Glu Ser Ile Asn Gln Gln Leu Leu Pro Leu Gly Asn Ile Ser Asp
        2355                2360                2365

Asn Met Asp Arg Ile Arg Glu Leu Ile Gln Gln Ala Arg Asp Ala Ala
    2370                2375                2380

Ser Lys Val Ala Val Pro Met Arg Phe Asn Gly Lys Ser Gly Val Glu
2385                2390                2395                2400

Val Arg Leu Pro Asn Asp Leu Glu Asp Leu Lys Gly Tyr Thr Ser Leu
                2405                2410                2415

Ser Leu Phe Leu Gln Arg Pro Asn Ser Arg Glu Asn Gly Gly Thr Glu
            2420                2425                2430

Asn Met Phe Val Met Tyr Leu Gly Asn Lys Asp Ala Ser Arg Asp Tyr
        2435                2440                2445

Ile Gly Met Ala Val Val Asp Gly Gln Leu Thr Cys Val Tyr Asn Leu
    2450                2455                2460

Gly Asp Arg Glu Ala Glu Leu Gln Val Asp Gln Ile Leu Thr Lys Ser
2465                2470                2475                2480

Glu Thr Lys Glu Ala Val Met Asp Arg Val Lys Phe Gln Arg Ile Tyr
                2485                2490                2495

Gln Phe Ala Arg Leu Asn Tyr Thr Lys Gly Ala Thr Ser Ser Lys Pro
            2500                2505                2510

Glu Thr Pro Gly Val Tyr Asp Met Asp Gly Arg Asn Ser Asn Thr Leu
        2515                2520                2525

Leu Asn Leu Asp Pro Glu Asn Val Val Phe Tyr Val Gly Gly Tyr Pro
    2530                2535                2540

Pro Asp Phe Lys Leu Pro Ser Arg Leu Ser Phe Pro Pro Tyr Lys Gly
2545                2550                2555                2560

Cys Ile Glu Leu Asp Asp Leu Asn Glu Asn Val Leu Ser Leu Tyr Asn
                2565                2570                2575

Phe Lys Lys Thr Phe Asn Leu Asn Thr Thr Glu Val Glu Pro Cys Arg
            2580                2585                2590

Arg Arg Lys Glu Glu Ser Asp Lys Asn Tyr Phe Glu Gly Thr Gly Tyr
        2595                2600                2605

Ala Arg Val Pro Thr Gln Pro His Ala Pro Ile Pro Thr Phe Gly Gln
    2610                2615                2620

Thr Ile Gln Thr Thr Val Asp Arg Gly Leu Leu Phe Phe Ala Glu Asn
2625                2630                2635                2640

Gly Asp Arg Phe Ile Ser Leu Asn Ile Glu Asp Gly Lys Leu Met Val
                2645                2650                2655

Arg Tyr Lys Leu Asn Ser Glu Leu Pro Lys Glu Arg Gly Val Gly Asp
            2660                2665                2670
```

-continued

```
Ala Ile Asn Asn Gly Arg Asp His Ser Ile Gln Ile Lys Ile Gly Lys
       2675                2680                2685

Leu Gln Lys Arg Met Trp Ile Asn Val Asp Val Gln Asn Thr Ile Ile
   2690                2695                2700

Asp Gly Glu Val Phe Asp Phe Ser Thr Tyr Tyr Leu Gly Gly Ile Pro
2705               2710                2715                2720

Ile Ala Ile Arg Glu Arg Phe Asn Ile Ser Thr Pro Ala Phe Arg Gly
               2725                2730                2735

Cys Met Lys Asn Leu Lys Lys Thr Ser Gly Val Val Arg Leu Asn Asp
           2740                2745                2750

Thr Val Gly Val Thr Lys Lys Cys Ser Glu Asp Trp Lys Leu Val Arg
       2755                2760                2765

Ser Ala Ser Phe Ser Arg Gly Gly Gln Leu Ser Phe Thr Asp Leu Gly
   2770                2775                2780

Leu Pro Pro Thr Asp His Leu Gln Ala Ser Phe Gly Phe Gln Thr Phe
2785               2790                2795                2800

Gln Pro Ser Gly Ile Leu Leu Asp His Gln Thr Trp Thr Arg Asn Leu
               2805                2810                2815

Gln Val Thr Leu Glu Asp Gly Tyr Ile Glu Leu Ser Thr Ser Asp Ser
           2820                2825                2830

Gly Gly Pro Ile Phe Lys Ser Pro Gln Thr Tyr Met Asp Gly Leu Leu
       2835                2840                2845

His Tyr Val Ser Val Ile Ser Asp Asn Ser Gly Leu Arg Leu Leu Ile
   2850                2855                2860

Asp Asp Gln Leu Leu Arg Asn Ser Lys Arg Leu Lys His Ile Ser Ser
2865               2870                2875                2880

Ser Arg Gln Ser Leu Arg Leu Gly Gly Ser Asn Phe Glu Gly Cys Ile
               2885                2890                2895

Ser Asn Val Phe Val Gln Arg Leu Ser Leu Ser Pro Glu Val Leu Asp
           2900                2905                2910

Leu Thr Ser Asn Ser Leu Lys Arg Asp Val Ser Leu Gly Gly Cys Ser
       2915                2920                2925

Leu Asn Lys Pro Pro Phe Leu Met Leu Leu Lys Gly Ser Thr Arg Phe
   2930                2935                2940


<210> SEQ ID NO 9
<211> LENGTH: 5139
<212> TYPE: DNA
<213> ORGANISM: Homo sapiens

<400> SEQUENCE: 9

atgggatggc tgtggatctt tggggcagcc ctggggcagt gtctgggcta cagttcacag     60

cagcaaaggg tgccatttct tcagcctccc ggtcaaagtc aactgcaagc gagttatgtg    120

gagtttagac ccagccaggg ttgtagccct ggatactatc gggatcataa aggcttgtat    180

accggacggt gtgttccctg caattgcaac ggacattcaa atcaatgcca ggatggctca    240

ggcatatgtg ttaactgtca gcacaacacc gcgggagagc actgtgaacg ctgccaggag    300

ggctactatg gcaacgccgt ccacggatcc tgcagggcct gcccatgtcc tcacactaac    360

agctttgcca ctggctgtgt ggtgaatggg ggagacgtgc ggtgctcctg caaagctggg    420

tacacaggaa cacagtgtga aaggtgtgca ccgggatatt tcgggaatcc ccagaaattc    480

ggaggtagct gccaaccatg cagttgtaac agcaatggcc agctgggcag ctgtcatccc    540

ctgactggag actgcataaa ccaagaaccc aaagatagca gccctgcaga agaatgtgat    600
```

-continued

```
gattgcgaca gctgtgtgat gaccctcctg aacgacctgg ccaccatggg cgagcagctc    660
cgcctggtca agtctcagct gcagggcctg agtgccagcg cagggcttct ggagcagatg    720
aggcacatgg agacccaggc caaggacctg aggaatcagt tgctcaacta ccgttctgcc    780
atttcaaatc atggatcaaa aatagaaggc ctggaaagag aactgactga tttgaatcaa    840
gaatttgaga ctttgcaaga aaaggctcaa gtaaattcca gaaaagcaca aacattaaac    900
aacaatgtta atcgggcaac acaaagcgca aaagaactgg atgtgaagat taaaaatgtc    960
atccggaatg tgcacattct tttaaagcag atctctggga cagatggaga gggaaacaac   1020
gtgccttcag gtgacttttc cagagagtgg gctgaagccc agcgcatgat gagggaactg   1080
cggaacagga actttggaaa gcacctcaga gaagcagaag ctgataaaag ggagtcgcag   1140
ctcttgctga accggataag gacctggcag aaaacccacc agggggagaa caatgggctt   1200
gctaacagta tccgggattc tttaaatgaa tacgaagcca aactcagtga ccttcgtgct   1260
cggctgcagg aggcagctgc ccaagccaag caggcaaatg gcttgaacca agaaaacgag   1320
agagctttgg gagccattca gagacaagtg aaagaaataa attccctgca gagtgatttc   1380
accaagtatc taaccactgc agactcatct ttgttgcaaa ccaacattgc gctgcagctg   1440
atggagaaaa gccagaagga atatgaaaaa ttagctgcca gtttaaatga agcaagacaa   1500
gaactaagtg acaaagtaag agaactttcc agatctgctg gcaaaacatc ccttgtggag   1560
gaggcagaaa agcacgcgcg gtccttacaa gagctggcaa agcagctgga agagatcaag   1620
agaaacgcca gcggggatga gctggtgcgc tgtgctgtgg atgccgccac cgcctacgag   1680
aacatcctca atgccatcaa agcggccgag gacgcagcca acagggctgc cagtgcatct   1740
gaatctgccc tccagacagt gataaaggaa gatctgccaa gaaaagctaa aaccctgagt   1800
tccaacagtg ataaactgtt aaatgaagcc aagatgacac aaaagaagct aaagcaagaa   1860
gtcagtccag ctctcaacaa cctacagcaa accctgaata ttgtgacagt tcagaaagaa   1920
gtgatagaca ccaatctcac aactctccga gatggtcttc atgggataca gagaggtgat   1980
attgatgcta tgatcagtag tgcaaagagc atggtcagaa aggccaacga catcacagat   2040
gaggttctgg atgggctcaa ccccatccag acagatgtgg aaagaattaa ggacacctat   2100
gggaggacac agaacgaaga cttcaaaaag gctctgactg atgcagataa ctcggtgaat   2160
aagttaacca acaaactacc tgatctttgg cgcaagattg aaagtatcaa ccaacagctg   2220
ttgcccttgg gaaacatctc tgacaacatg gacagaatac gagaactaat tcagcaggcc   2280
agagatgctg ccagtaaggt tgctgtcccc atgaggttca atggtaaatc tggagtcgaa   2340
gtccgactgc caaatgacct ggaagatttg aaaggatata catctctgtc cttgtttctc   2400
caaaggccca actcaagaga aaatgggggt actgagaata tgtttgtgat gtaccttgga   2460
aataaagatg cctcccggga ctacatcggc atggcagttg tggatggcca gctcacctgt   2520
gtctacaacc tgggggaccg tgaggctgaa ctccaagtgg accagatctt gaccaagagt   2580
gagactaagg aggcagttat ggatcgggtg aaatttcaga gaatttatca gtttgcaagg   2640
cttaattaca ccaaaggagc cacatccagt aaaccagaaa cacccggagt ctatgacatg   2700
gatggtagaa atagcaatac actccttaat ttggatcctg aaaatgttgt attttatgtt   2760
ggaggttacc cacctgattt taaacttccc agtcgactaa gtttccctcc atacaaaggt   2820
tgtattgaat tagatgacct caatgaaaat gttctgagct tgtacaactt caaaaaaaca   2880
ttcaatctca acacaactga agtggagcct tgtagaagga ggaaggaaga gtcagacaaa   2940
aattattttg aaggtacggg ctatgctcga gttccaactc aaccacatgc tcccatccca   3000
```

-continued acctttggac agacaattca gaccaccgtg gatagaggct tgctgttctt tgcagaaaac 3060
ggggatcgct tcatatctct aaatatagaa gatggcaagc tcatggtgag atacaaactg 3120
aattcagagc taccaaaaga gagaggagtt ggagacgcca taaacaacgg cagagaccat 3180
tcgattcaga tcaaaattgg aaaactccaa aagcgtatgt ggataaatgt ggacgttcaa 3240
aacactataa ttgatggtga agtatttgat ttcagcacat attatctggg aggaattcca 3300
attgcaatca gggaaagatt taacatttct acgcctgctt tccgaggctg catgaaaaat 3360
ttgaagaaaa ccagtggtgt cgttagattg aatgatactg tgggagtaac caaaaagtgc 3420
tcggaagact ggaagcttgt gcgatctgcc tcattctcca gaggaggaca attgagtttc 3480
actgatttgg gcttaccacc tactgaccac ctccaggcct catttggatt tcagaccttt 3540
caacccagtg gcatattatt agatcatcag acatggacaa ggaacctgca ggtcactctg 3600
gaagatggtt acattgaatt gagcaccagc gatagcggcg gcccaatttt taaatctcca 3660
cagacgtata tggatggttt actgcattat gtatctgtaa taagcgacaa ctctggacta 3720
cggcttctca tcgatgacca gcttctgaga aatagcaaaa ggctaaaaca catttcaagt 3780
tcccggcagt ctctgcgtct gggcgggagc aattttgagg gttgtattag caatgttttt 3840
gtccagaggt tatcactgag tcctgaagtc ctagatttga ccagtaactc tctcaagaga 3900
gatgtgtccc tgggaggctg cagtttaaac aaaccacctt ttctaatgtt gcttaaaggt 3960
tctaccaggt ttaacaagac caagactttt cgtatcaacc agctgttgca ggacacacca 4020
gtggcctccc caaggagcgt gaaggtgtgg caagatgctt gctcaccact tcccaagacc 4080
caggccaatc atggagccct ccagtttggg gacattccca ccagccactt gctattcaag 4140
cttcctcagg agctgctgaa acccaggtca cagtttgctg tggacatgca gacaacatcc 4200
tccagaggac tggtgtttca cacgggcact aagaactcct ttatggctct ttatctttca 4260
aaaggacgtc tggtctttgc actggggaca gatgggaaaa aattgaggat caaaagcaag 4320
gagaaatgca atgatgggaa atggcacacg gtggtgtttg gccatgatgg ggaaaagggg 4380
cgcttggttg tggatggact gagggcccgg gagggaagtt tgcctggaaa ctccaccatc 4440
agcatcagag cgccagttta cctgggatca cctccatcag ggaaaccaaa gagcctcccc 4500
acaaacagct ttgtgggatg cctgaagaac tttcagctgg attcaaaacc cttgtatacc 4560
ccttcttcaa gcttcggggt gtcttcctgc ttgggtggtc ctttggagaa aggcatttat 4620
ttctctgaag aaggaggtca tgtcgtcttg gctcactctg tattgttggg gccagaattt 4680
aagcttgttt tcagcatccg cccaagaagt ctcactggga tcctaataca catcggaagt 4740
cagcccggga agcacttatg tgtttacctg gaggcaggaa aggtcacggc ctctatggac 4800
agtggggcag gtgggacctc aacgtcggtc acaccaaagc agtctctgtg tgatggacag 4860
tggcactcgg tggcagtcac cataaaacaa cacatcctgc acctggaact ggacacagac 4920
agtagctaca cagctggaca gatcccccttc ccacctgcca gcactcaaga gccactacac 4980
cttggaggtg ctccagccaa tttgacgaca ctgaggatcc ctgtgtggaa atcattcttt 5040
ggctgtctga ggaatattca tgtcaatcac atccctgtcc ctgtcactga agccttggaa 5100
gtccaggggc ctgtcagtct gaatggttgt cctgaccag 5139

<210> SEQ ID NO 10
<211> LENGTH: 1713
<212> TYPE: PRT
<213> ORGANISM: Homo sapiens

<400> SEQUENCE: 10

-continued

```
Met Gly Trp Leu Trp Ile Phe Gly Ala Ala Leu Gly Gln Cys Leu Gly
 1               5                  10                  15

Tyr Ser Ser Gln Gln Gln Arg Val Pro Phe Leu Gln Pro Pro Gly Gln
            20                  25                  30

Ser Gln Leu Gln Ala Ser Tyr Val Glu Phe Arg Pro Ser Gln Gly Cys
        35                  40                  45

Ser Pro Gly Tyr Tyr Arg Asp His Lys Gly Leu Tyr Thr Gly Arg Cys
    50                  55                  60

Val Pro Cys Asn Cys Asn Gly His Ser Asn Gln Cys Gln Asp Gly Ser
65                  70                  75                  80

Gly Ile Cys Val Asn Cys Gln His Asn Thr Ala Gly Glu His Cys Glu
                85                  90                  95

Arg Cys Gln Glu Gly Tyr Tyr Gly Asn Ala Val His Gly Ser Cys Arg
            100                 105                 110

Ala Cys Pro Cys Pro His Thr Asn Ser Phe Ala Thr Gly Cys Val Val
        115                 120                 125

Asn Gly Gly Asp Val Arg Cys Ser Cys Lys Ala Gly Tyr Thr Gly Thr
    130                 135                 140

Gln Cys Glu Arg Cys Ala Pro Gly Tyr Phe Gly Asn Pro Gln Lys Phe
145                 150                 155                 160

Gly Gly Ser Cys Gln Pro Cys Ser Cys Asn Ser Asn Gly Gln Leu Gly
                165                 170                 175

Ser Cys His Pro Leu Thr Gly Asp Cys Ile Asn Gln Glu Pro Lys Asp
            180                 185                 190

Ser Ser Pro Ala Glu Glu Cys Asp Asp Cys Asp Ser Cys Val Met Thr
        195                 200                 205

Leu Leu Asn Asp Leu Ala Thr Met Gly Glu Gln Leu Arg Leu Val Lys
    210                 215                 220

Ser Gln Leu Gln Gly Leu Ser Ala Ser Ala Gly Leu Leu Glu Gln Met
225                 230                 235                 240

Arg His Met Glu Thr Gln Ala Lys Asp Leu Arg Asn Gln Leu Leu Asn
                245                 250                 255

Tyr Arg Ser Ala Ile Ser Asn His Gly Ser Lys Ile Glu Gly Leu Glu
            260                 265                 270

Arg Glu Leu Thr Asp Leu Asn Gln Glu Phe Glu Thr Leu Gln Glu Lys
        275                 280                 285

Ala Gln Val Asn Ser Arg Lys Ala Gln Thr Leu Asn Asn Asn Val Asn
    290                 295                 300

Arg Ala Thr Gln Ser Ala Lys Glu Leu Asp Val Lys Ile Lys Asn Val
305                 310                 315                 320

Ile Arg Asn Val His Ile Leu Leu Lys Gln Ile Ser Gly Thr Asp Gly
                325                 330                 335

Glu Gly Asn Asn Val Pro Ser Gly Asp Phe Ser Arg Glu Trp Ala Glu
            340                 345                 350

Ala Gln Arg Met Met Arg Glu Leu Arg Asn Arg Asn Phe Gly Lys His
        355                 360                 365

Leu Arg Glu Ala Glu Ala Asp Lys Arg Glu Ser Gln Leu Leu Leu Asn
    370                 375                 380

Arg Ile Arg Thr Trp Gln Lys Thr His Gln Gly Glu Asn Asn Gly Leu
385                 390                 395                 400

Ala Asn Ser Ile Arg Asp Ser Leu Asn Glu Tyr Glu Ala Lys Leu Ser
                405                 410                 415

Asp Leu Arg Ala Arg Leu Gln Glu Ala Ala Ala Gln Ala Lys Gln Ala
            420                 425                 430
```

-continued

```
Asn Gly Leu Asn Gln Glu Asn Glu Arg Ala Leu Gly Ala Ile Gln Arg
        435                 440                 445

Gln Val Lys Glu Ile Asn Ser Leu Gln Ser Asp Phe Thr Lys Tyr Leu
    450                 455                 460

Thr Thr Ala Asp Ser Ser Leu Leu Gln Thr Asn Ile Ala Leu Gln Leu
465                 470                 475                 480

Met Glu Lys Ser Gln Lys Glu Tyr Glu Lys Leu Ala Ala Ser Leu Asn
                485                 490                 495

Glu Ala Arg Gln Glu Leu Ser Asp Lys Val Arg Glu Leu Ser Arg Ser
            500                 505                 510

Ala Gly Lys Thr Ser Leu Val Glu Glu Ala Glu Lys His Ala Arg Ser
        515                 520                 525

Leu Gln Glu Leu Ala Lys Gln Leu Glu Glu Ile Lys Arg Asn Ala Ser
    530                 535                 540

Gly Asp Glu Leu Val Arg Cys Ala Val Asp Ala Ala Thr Ala Tyr Glu
545                 550                 555                 560

Asn Ile Leu Asn Ala Ile Lys Ala Ala Glu Asp Ala Ala Asn Arg Ala
                565                 570                 575

Ala Ser Ala Ser Glu Ser Ala Leu Gln Thr Val Ile Lys Glu Asp Leu
            580                 585                 590

Pro Arg Lys Ala Lys Thr Leu Ser Ser Asn Ser Asp Lys Leu Leu Asn
        595                 600                 605

Glu Ala Lys Met Thr Gln Lys Lys Leu Lys Gln Glu Val Ser Pro Ala
    610                 615                 620

Leu Asn Asn Leu Gln Gln Thr Leu Asn Ile Val Thr Val Gln Lys Glu
625                 630                 635                 640

Val Ile Asp Thr Asn Leu Thr Thr Leu Arg Asp Gly Leu His Gly Ile
                645                 650                 655

Gln Arg Gly Asp Ile Asp Ala Met Ile Ser Ser Ala Lys Ser Met Val
            660                 665                 670

Arg Lys Ala Asn Asp Ile Thr Asp Glu Val Leu Asp Gly Leu Asn Pro
        675                 680                 685

Ile Gln Thr Asp Val Glu Arg Ile Lys Asp Thr Tyr Gly Arg Thr Gln
    690                 695                 700

Asn Glu Asp Phe Lys Lys Ala Leu Thr Asp Ala Asp Asn Ser Val Asn
705                 710                 715                 720

Lys Leu Thr Asn Lys Leu Pro Asp Leu Trp Arg Lys Ile Glu Ser Ile
                725                 730                 735

Asn Gln Gln Leu Leu Pro Leu Gly Asn Ile Ser Asp Asn Met Asp Arg
            740                 745                 750

Ile Arg Glu Leu Ile Gln Gln Ala Arg Asp Ala Ala Ser Lys Val Ala
        755                 760                 765

Val Pro Met Arg Phe Asn Gly Lys Ser Gly Val Glu Val Arg Leu Pro
    770                 775                 780

Asn Asp Leu Glu Asp Leu Lys Gly Tyr Thr Ser Leu Ser Leu Phe Leu
785                 790                 795                 800

Gln Arg Pro Asn Ser Arg Glu Asn Gly Gly Thr Glu Asn Met Phe Val
                805                 810                 815

Met Tyr Leu Gly Asn Lys Asp Ala Ser Arg Asp Tyr Ile Gly Met Ala
            820                 825                 830

Val Val Asp Gly Gln Leu Thr Cys Val Tyr Asn Leu Gly Asp Arg Glu
        835                 840                 845

Ala Glu Leu Gln Val Asp Gln Ile Leu Thr Lys Ser Glu Thr Lys Glu
```

-continued

```
    850                 855                 860

Ala Val Met Asp Arg Val Lys Phe Gln Arg Ile Tyr Gln Phe Ala Arg
865                 870                 875                 880

Leu Asn Tyr Thr Lys Gly Ala Thr Ser Ser Lys Pro Glu Thr Pro Gly
                885                 890                 895

Val Tyr Asp Met Asp Gly Arg Asn Ser Asn Thr Leu Leu Asn Leu Asp
            900                 905                 910

Pro Glu Asn Val Val Phe Tyr Val Gly Gly Tyr Pro Pro Asp Phe Lys
        915                 920                 925

Leu Pro Ser Arg Leu Ser Phe Pro Pro Tyr Lys Gly Cys Ile Glu Leu
    930                 935                 940

Asp Asp Leu Asn Glu Asn Val Leu Ser Leu Tyr Asn Phe Lys Lys Thr
945                 950                 955                 960

Phe Asn Leu Asn Thr Thr Glu Val Glu Pro Cys Arg Arg Arg Lys Glu
                965                 970                 975

Glu Ser Asp Lys Asn Tyr Phe Glu Gly Thr Gly Tyr Ala Arg Val Pro
            980                 985                 990

Thr Gln Pro His Ala Pro Ile Pro  Thr Phe Gly Gln Thr  Ile Gln Thr
        995                 1000                1005

Thr Val  Asp Arg Gly Leu Leu  Phe Phe Ala Glu Asn  Gly Asp Arg
    1010                1015                1020

Phe Ile  Ser Leu Asn Ile Glu  Asp Gly Lys Leu Met  Val Arg Tyr
    1025                1030                1035

Lys Leu  Asn Ser Glu Leu Pro  Lys Glu Arg Gly Val  Gly Asp Ala
    1040                1045                1050

Ile Asn  Asn Gly Arg Asp His  Ser Ile Gln Ile Lys  Ile Gly Lys
    1055                1060                1065

Leu Gln  Lys Arg Met Trp Ile  Asn Val Asp Val Gln  Asn Thr Ile
    1070                1075                1080

Ile Asp  Gly Glu Val Phe Asp  Phe Ser Thr Tyr Tyr  Leu Gly Gly
    1085                1090                1095

Ile Pro  Ile Ala Ile Arg Glu  Arg Phe Asn Ile Ser  Thr Pro Ala
    1100                1105                1110

Phe Arg  Gly Cys Met Lys Asn  Leu Lys Lys Thr Ser  Gly Val Val
    1115                1120                1125

Arg Leu  Asn Asp Thr Val Gly  Val Thr Lys Lys Cys  Ser Glu Asp
    1130                1135                1140

Trp Lys  Leu Val Arg Ser Ala  Ser Phe Ser Arg Gly  Gly Gln Leu
    1145                1150                1155

Ser Phe  Thr Asp Leu Gly Leu  Pro Pro Thr Asp His  Leu Gln Ala
    1160                1165                1170

Ser Phe  Gly Phe Gln Thr Phe  Gln Pro Ser Gly Ile  Leu Leu Asp
    1175                1180                1185

His Gln  Thr Trp Thr Arg Asn  Leu Gln Val Thr Leu  Glu Asp Gly
    1190                1195                1200

Tyr Ile  Glu Leu Ser Thr Ser  Asp Ser Gly Gly Pro  Ile Phe Lys
    1205                1210                1215

Ser Pro  Gln Thr Tyr Met Asp  Gly Leu Leu His Tyr  Val Ser Val
    1220                1225                1230

Ile Ser  Asp Asn Ser Gly Leu  Arg Leu Leu Ile Asp  Asp Gln Leu
    1235                1240                1245

Leu Arg  Asn Ser Lys Arg Leu  Lys His Ile Ser Ser  Phe Arg Gln
    1250                1255                1260
```

```
Ser Leu  Arg Leu Gly Gly Ser  Asn Phe Glu Gly Cys  Ile Ser Asn
    1265                 1270                 1275

Val Phe  Val Gln Arg Leu Ser  Leu Ser Pro Glu Val  Leu Asp Leu
    1280                 1285                 1290

Thr Ser  Asn Ser Leu Lys Arg  Asp Val Ser Leu Gly  Gly Cys Ser
    1295                 1300                 1305

Leu Asn  Lys Pro Pro Phe Leu  Met Leu Leu Lys Gly  Ser Thr Arg
    1310                 1315                 1320

Phe Asn  Lys Thr Lys Thr Phe  Arg Ile Asn Gln Leu  Leu Gln Asp
    1325                 1330                 1335

Thr Pro  Val Ala Ser Pro Arg  Ser Val Lys Val Trp  Gln Asp Ala
    1340                 1345                 1350

Cys Ser  Pro Leu Pro Lys Thr  Gln Ala Asn His Gly  Ala Leu Gln
    1355                 1360                 1365

Phe Gly  Asp Ile Pro Thr Ser  His Leu Leu Phe Lys  Leu Pro Gln
    1370                 1375                 1380

Glu Leu  Leu Lys Pro Arg Ser  Gln Phe Ala Val Asp  Met Gln Thr
    1385                 1390                 1395

Thr Ser  Ser Arg Gly Leu Val  Phe His Thr Gly Thr  Lys Asn Ser
    1400                 1405                 1410

Phe Met  Ala Leu Tyr Leu Ser  Lys Gly Arg Leu Val  Phe Ala Leu
    1415                 1420                 1425

Gly Thr  Asp Gly Lys Lys Leu  Arg Ile Lys Ser Lys  Glu Lys Cys
    1430                 1435                 1440

Asn Asp  Gly Lys Trp His Thr  Val Val Phe Gly His  Asp Gly Glu
    1445                 1450                 1455

Lys Gly  Arg Leu Val Val Asp  Gly Leu Arg Ala Arg  Glu Gly Ser
    1460                 1465                 1470

Leu Pro  Gly Asn Ser Thr Ile  Ser Ile Arg Ala Pro  Val Tyr Leu
    1475                 1480                 1485

Gly Ser  Pro Pro Ser Gly Lys  Pro Lys Ser Leu Pro  Thr Asn Ser
    1490                 1495                 1500

Phe Val  Gly Cys Leu Lys Asn  Phe Gln Leu Asp Ser  Lys Pro Leu
    1505                 1510                 1515

Tyr Thr  Pro Ser Ser Ser Phe  Gly Val Ser Ser Cys  Leu Gly Gly
    1520                 1525                 1530

Pro Leu  Glu Lys Gly Ile Tyr  Phe Ser Glu Glu Gly  Gly His Val
    1535                 1540                 1545

Val Leu  Ala His Ser Val Leu  Leu Gly Pro Glu Phe  Lys Leu Val
    1550                 1555                 1560

Phe Ser  Ile Arg Pro Arg Ser  Leu Thr Gly Ile Leu  Ile His Ile
    1565                 1570                 1575

Gly Ser  Gln Pro Gly Lys His  Leu Cys Val Tyr Leu  Glu Ala Gly
    1580                 1585                 1590

Lys Val  Thr Ala Ser Met Asp  Ser Gly Ala Gly Gly  Thr Ser Thr
    1595                 1600                 1605

Ser Val  Thr Pro Lys Gln Ser  Leu Cys Asp Gly Gln  Trp His Ser
    1610                 1615                 1620

Val Ala  Val Thr Ile Lys Gln  His Ile Leu His Leu  Glu Leu Asp
    1625                 1630                 1635

Thr Asp  Ser Ser Tyr Thr Ala  Gly Gln Ile Pro Phe  Pro Pro Ala
    1640                 1645                 1650

Ser Thr  Gln Glu Pro Leu His  Leu Gly Gly Ala Pro  Ala Asn Leu
    1655                 1660                 1665
```

```
Thr Thr  Leu Arg Ile Pro Val  Trp Lys Ser Phe Phe  Gly Cys Leu
    1670                 1675                 1680

Arg Asn  Ile His Val Asn His  Ile Pro Val Pro Val  Thr Glu Ala
    1685                 1690                 1695

Leu Glu  Val Gln Gly Pro Val  Ser Leu Asn Gly Cys  Pro Asp Gln
    1700                 1705                 1710


<210> SEQ ID NO 11
<211> LENGTH: 4011
<212> TYPE: DNA
<213> ORGANISM: Homo sapiens

<400> SEQUENCE: 11

atgggatggc tgtggatctt tggggcagcc ctggggcagt gtctgggcta cagttcacag     60

cagcaaaggg tgccatttct tcagcctccc ggtcaaagtc aactgcaagc gagttatgtg    120

gagtttagac ccagccaggg ttgtagccct ggatactatc gggatcataa aggcttgtat    180

accggacggt gtgttccctg caattgcaac ggacattcaa atcaatgcca ggatggctca    240

ggcatatgtg ttaactgtca gcacaacacc gcgggagagc actgtgaacg ctgccaggag    300

ggctactatg gcaacgccgt ccacggatcc tgcagggcct gcccatgtcc tcacactaac    360

agctttgcca ctggctgtgt ggtgaatggg ggagacgtgc ggtgctcctg caaagctggg    420

tacacaggaa cacagtgtga aaggtgtgca ccgggatatt tcgggaatcc ccagaaattc    480

ggaggtagct gccaaccatg cagttgtaac agcaatggcc agctgggcag ctgtcatccc    540

ctgactggag actgcataaa ccaagaaccc aaagatagca gccctgcaga agaatgtgat    600

gattgcgaca gctgtgtgat gaccctcctg aacgacctgg ccaccatggg cgagcagctc    660

cgcctggtca agtctcagct gcagggcctg agtgccagcg cagggcttct ggagcagatg    720

aggcacatgg agacccaggc caaggacctg aggaatcagt tgctcaacta ccgttctgcc    780

atttcaaatc atggatcaaa aatagaaggc ctggaaagag aactgactga tttgaatcaa    840

gaatttgaga ctttgcaaga aaaggctcaa gtaaattcca gaaaagcaca aacattaaac    900

aacaatgtta atcgggcaac acaaagcgca aaagaactgg atgtgaagat taaaaatgtc    960

atccggaatg tgcacattct tttaaagcag atctctggga cagatggaga gggaaacaac   1020

gtgccttcag gtgacttttc cagagagtgg gctgaagccc agcgcatgat gagggaactg   1080

cggaacagga actttggaaa gcacctcaga gaagcagaag ctgataaaag ggagtcgcag   1140

ctcttgctga accggataag gacctggcag aaaacccacc aggggggagaa caatgggctt   1200

gctaacagta tccgggattc tttaaatgaa tacgaagcca aactcagtga ccttcgtgct   1260

cggctgcagg aggcagctgc ccaagccaag caggcaaatg gcttgaacca agaaaacgag   1320

agagctttgg gagccattca gagacaagtg aaagaaataa attccctgca gagtgatttc   1380

accaagtatc taaccactgc agactcatct ttgttgcaaa ccaacattgc gctgcagctg   1440

atggagaaaa gccagaagga atatgaaaaa ttagctgcca gtttaaatga agcaagacaa   1500

gaactaagtg acaaagtaag agaactttcc agatctgctg gcaaaacatc ccttgtggag   1560

gaggcagaaa agcacgcgcg gtccttacaa gagctggcaa agcagctgga agagatcaag   1620

agaaacgcca gcggggatga gctggtgcgc tgtgctgtgg atgccgccac cgcctacgag   1680

aacatcctca atgccatcaa agcggccgag gacgcagcca acagggctgc cagtgcatct   1740

gaatctgccc tccagacagt gataaaggaa gatctgccaa gaaaagctaa aaccctgagt   1800

tccaacagtg ataaactgtt aaatgaagcc aagatgacac aaaagaagct aaagcaagaa   1860
```

-continued

```
gtcagtccag ctctcaacaa cctacagcaa accctgaata ttgtgacagt tcagaaagaa   1920

gtgatagaca ccaatctcac aactctccga gatggtcttc atgggataca gagaggtgat   1980

attgatgcta tgatcagtag tgcaaagagc atggtcagaa aggccaacga catcacagat   2040

gaggttctgg atgggctcaa ccccatccag acagatgtgg aaagaattaa ggacacctat   2100

gggaggacac agaacgaaga cttcaaaaag gctctgactg atgcagataa ctcggtgaat   2160

aagttaacca acaaactacc tgatctttgg cgcaagattg aaagtatcaa ccaacagctg   2220

ttgcccttgg gaaacatctc tgacaacatg gacagaatac gagaactaat tcagcaggcc   2280

agagatgctg ccagtaaggt tgctgtcccc atgaggttca atggtaaatc tggagtcgaa   2340

gtccgactgc caaatgacct ggaagatttg aaaggatata catctctgtc cttgtttctc   2400

caaaggccca actcaagaga aaatgggggt actgagaata tgtttgtgat gtaccttgga   2460

aataaagatg cctcccggga ctacatcggc atggcagttg tggatggcca gctcacctgt   2520

gtctacaacc tgggggaccg tgaggctgaa ctccaagtgg accagatctt gaccaagagt   2580

gagactaagg aggcagttat ggatcgggtg aaatttcaga gaatttatca gtttgcaagg   2640

cttaattaca ccaaaggagc cacatccagt aaaccagaaa cacccggagt ctatgacatg   2700

gatggtagaa atagcaatac actccttaat ttggatcctg aaaatgttgt attttatgtt   2760

ggaggttacc cacctgattt taaacttccc agtcgactaa gtttccctcc atacaaaggt   2820

tgtattgaat tagatgacct caatgaaaat gttctgagct tgtacaactt caaaaaaaca   2880

ttcaatctca acacaactga agtggagcct tgtagaagga ggaaggaaga gtcagacaaa   2940

aattattttg aaggtacggg ctatgctcga gttccaactc aaccacatgc tcccatccca   3000

acctttggac agacaattca gaccaccgtg gatagaggct tgctgttctt tgcagaaaac   3060

ggggatcgct tcatatctct aaatatagaa gatggcaagc tcatggtgag atacaaactg   3120

aattcagagc taccaaaaga gagaggagtt ggagacgcca taaacaacgg cagagaccat   3180

tcgattcaga tcaaaattgg aaaactccaa aagcgtatgt ggataaatgt ggacgttcaa   3240

aacactataa ttgatggtga agtatttgat ttcagcacat attatctggg aggaattcca   3300

attgcaatca gggaaagatt taacatttct acgcctgctt tccgaggctg catgaaaaat   3360

ttgaagaaaa ccagtggtgt cgttagattg aatgatactg tgggagtaac caaaaagtgc   3420

tcggaagact ggaagcttgt gcgatctgcc tcattctcca gaggaggaca attgagtttc   3480

actgatttgg gcttaccacc tactgaccac ctccaggcct catttggatt tcagaccttt   3540

caacccagtg gcatattatt agatcatcag acatggacaa ggaacctgca ggtcactctg   3600

gaagatggtt acattgaatt gagcaccagc gatagcggcg gcccaatttt taaatctcca   3660

cagacgtata tggatggttt actgcattat gtatctgtaa taagcgacaa ctctggacta   3720

cggcttctca tcgatgacca gcttctgaga aatagcaaaa ggctaaaaca catttcaagt   3780

tcccggcagt ctctgcgtct gggcgggagc aattttgagg gttgtattag caatgttttt   3840

gtccagaggt tatcactgag tcctgaagtc ctagatttga ccagtaactc tctcaagaga   3900

gatgtgtccc tgggaggctg cagtttaaac aaaccacctt ttctaatgtt gcttaaaggt   3960

tctaccaggt ttaacaagac caagactttt cgtatcaacc agctgttgca g            4011
```

<210> SEQ ID NO 12
<211> LENGTH: 1337
<212> TYPE: PRT
<213> ORGANISM: Homo sapiens

<400> SEQUENCE: 12

-continued

```
Met Gly Trp Leu Trp Ile Phe Gly Ala Ala Leu Gly Gln Cys Leu Gly
  1               5                  10                  15

Tyr Ser Ser Gln Gln Gln Arg Val Pro Phe Leu Gln Pro Pro Gly Gln
             20                  25                  30

Ser Gln Leu Gln Ala Ser Tyr Val Glu Phe Arg Pro Ser Gln Gly Cys
         35                  40                  45

Ser Pro Gly Tyr Tyr Arg Asp His Lys Gly Leu Tyr Thr Gly Arg Cys
     50                  55                  60

Val Pro Cys Asn Cys Asn Gly His Ser Asn Gln Cys Gln Asp Gly Ser
 65                  70                  75                  80

Gly Ile Cys Val Asn Cys Gln His Asn Thr Ala Gly Glu His Cys Glu
                 85                  90                  95

Arg Cys Gln Glu Gly Tyr Tyr Gly Asn Ala Val His Gly Ser Cys Arg
            100                 105                 110

Ala Cys Pro Cys Pro His Thr Asn Ser Phe Ala Thr Gly Cys Val Val
        115                 120                 125

Asn Gly Gly Asp Val Arg Cys Ser Cys Lys Ala Gly Tyr Thr Gly Thr
    130                 135                 140

Gln Cys Glu Arg Cys Ala Pro Gly Tyr Phe Gly Asn Pro Gln Lys Phe
145                 150                 155                 160

Gly Gly Ser Cys Gln Pro Cys Ser Cys Asn Ser Asn Gly Gln Leu Gly
                165                 170                 175

Ser Cys His Pro Leu Thr Gly Asp Cys Ile Asn Gln Glu Pro Lys Asp
            180                 185                 190

Ser Ser Pro Ala Glu Glu Cys Asp Asp Cys Asp Ser Cys Val Met Thr
        195                 200                 205

Leu Leu Asn Asp Leu Ala Thr Met Gly Glu Gln Leu Arg Leu Val Lys
    210                 215                 220

Ser Gln Leu Gln Gly Leu Ser Ala Ser Ala Gly Leu Leu Glu Gln Met
225                 230                 235                 240

Arg His Met Glu Thr Gln Ala Lys Asp Leu Arg Asn Gln Leu Leu Asn
                245                 250                 255

Tyr Arg Ser Ala Ile Ser Asn His Gly Ser Lys Ile Glu Gly Leu Glu
            260                 265                 270

Arg Glu Leu Thr Asp Leu Asn Gln Glu Phe Glu Thr Leu Gln Glu Lys
        275                 280                 285

Ala Gln Val Asn Ser Arg Lys Ala Gln Thr Leu Asn Asn Asn Val Asn
    290                 295                 300

Arg Ala Thr Gln Ser Ala Lys Glu Leu Asp Val Lys Ile Lys Asn Val
305                 310                 315                 320

Ile Arg Asn Val His Ile Leu Leu Lys Gln Ile Ser Gly Thr Asp Gly
                325                 330                 335

Glu Gly Asn Asn Val Pro Ser Gly Asp Phe Ser Arg Glu Trp Ala Glu
            340                 345                 350

Ala Gln Arg Met Met Arg Glu Leu Arg Asn Arg Asn Phe Gly Lys His
        355                 360                 365

Leu Arg Glu Ala Glu Ala Asp Lys Arg Glu Ser Gln Leu Leu Leu Asn
    370                 375                 380

Arg Ile Arg Thr Trp Gln Lys Thr His Gln Gly Glu Asn Asn Gly Leu
385                 390                 395                 400

Ala Asn Ser Ile Arg Asp Ser Leu Asn Glu Tyr Glu Ala Lys Leu Ser
                405                 410                 415

Asp Leu Arg Ala Arg Leu Gln Glu Ala Ala Ala Gln Ala Lys Gln Ala
            420                 425                 430
```

-continued

Asn Gly Leu Asn Gln Glu Asn Glu Arg Ala Leu Gly Ala Ile Gln Arg
435 440 445

Gln Val Lys Glu Ile Asn Ser Leu Gln Ser Asp Phe Thr Lys Tyr Leu
450 455 460

Thr Thr Ala Asp Ser Ser Leu Leu Gln Thr Asn Ile Ala Leu Gln Leu
465 470 475 480

Met Glu Lys Ser Gln Lys Glu Tyr Glu Lys Leu Ala Ala Ser Leu Asn
485 490 495

Glu Ala Arg Gln Glu Leu Ser Asp Lys Val Arg Glu Leu Ser Arg Ser
500 505 510

Ala Gly Lys Thr Ser Leu Val Glu Glu Ala Glu Lys His Ala Arg Ser
515 520 525

Leu Gln Glu Leu Ala Lys Gln Leu Glu Glu Ile Lys Arg Asn Ala Ser
530 535 540

Gly Asp Glu Leu Val Arg Cys Ala Val Asp Ala Ala Thr Ala Tyr Glu
545 550 555 560

Asn Ile Leu Asn Ala Ile Lys Ala Ala Glu Asp Ala Ala Asn Arg Ala
565 570 575

Ala Ser Ala Ser Glu Ser Ala Leu Gln Thr Val Ile Lys Glu Asp Leu
580 585 590

Pro Arg Lys Ala Lys Thr Leu Ser Ser Asn Ser Asp Lys Leu Leu Asn
595 600 605

Glu Ala Lys Met Thr Gln Lys Lys Leu Lys Gln Glu Val Ser Pro Ala
610 615 620

Leu Asn Asn Leu Gln Gln Thr Leu Asn Ile Val Thr Val Gln Lys Glu
625 630 635 640

Val Ile Asp Thr Asn Leu Thr Thr Leu Arg Asp Gly Leu His Gly Ile
645 650 655

Gln Arg Gly Asp Ile Asp Ala Met Ile Ser Ser Ala Lys Ser Met Val
660 665 670

Arg Lys Ala Asn Asp Ile Thr Asp Glu Val Leu Asp Gly Leu Asn Pro
675 680 685

Ile Gln Thr Asp Val Glu Arg Ile Lys Asp Thr Tyr Gly Arg Thr Gln
690 695 700

Asn Glu Asp Phe Lys Lys Ala Leu Thr Asp Ala Asp Asn Ser Val Asn
705 710 715 720

Lys Leu Thr Asn Lys Leu Pro Asp Leu Trp Arg Lys Ile Glu Ser Ile
725 730 735

Asn Gln Gln Leu Leu Pro Leu Gly Asn Ile Ser Asp Asn Met Asp Arg
740 745 750

Ile Arg Glu Leu Ile Gln Gln Ala Arg Asp Ala Ala Ser Lys Val Ala
755 760 765

Val Pro Met Arg Phe Asn Gly Lys Ser Gly Val Glu Val Arg Leu Pro
770 775 780

Asn Asp Leu Glu Asp Leu Lys Gly Tyr Thr Ser Leu Ser Leu Phe Leu
785 790 795 800

Gln Arg Pro Asn Ser Arg Glu Asn Gly Gly Thr Glu Asn Met Phe Val
805 810 815

Met Tyr Leu Gly Asn Lys Asp Ala Ser Arg Asp Tyr Ile Gly Met Ala
820 825 830

Val Val Asp Gly Gln Leu Thr Cys Val Tyr Asn Leu Gly Asp Arg Glu
835 840 845

Ala Glu Leu Gln Val Asp Gln Ile Leu Thr Lys Ser Glu Thr Lys Glu

-continued

```
    850                 855                 860

Ala Val Met Asp Arg Val Lys Phe Gln Arg Ile Tyr Gln Phe Ala Arg
865                 870                 875                 880

Leu Asn Tyr Thr Lys Gly Ala Thr Ser Ser Lys Pro Glu Thr Pro Gly
                885                 890                 895

Val Tyr Asp Met Asp Gly Arg Asn Ser Asn Thr Leu Leu Asn Leu Asp
            900                 905                 910

Pro Glu Asn Val Val Phe Tyr Val Gly Gly Tyr Pro Pro Asp Phe Lys
        915                 920                 925

Leu Pro Ser Arg Leu Ser Phe Pro Pro Tyr Lys Gly Cys Ile Glu Leu
    930                 935                 940

Asp Asp Leu Asn Glu Asn Val Leu Ser Leu Tyr Asn Phe Lys Lys Thr
945                 950                 955                 960

Phe Asn Leu Asn Thr Thr Glu Val Glu Pro Cys Arg Arg Arg Lys Glu
                965                 970                 975

Glu Ser Asp Lys Asn Tyr Phe Glu Gly Thr Gly Tyr Ala Arg Val Pro
            980                 985                 990

Thr Gln Pro His Ala Pro Ile Pro  Thr Phe Gly Gln Thr  Ile Gln Thr
        995                 1000                1005

Thr Val  Asp Arg Gly Leu Leu  Phe Phe Ala Glu Asn  Gly Asp Arg
    1010                1015                1020

Phe Ile  Ser Leu Asn Ile Glu  Asp Gly Lys Leu Met  Val Arg Tyr
    1025                1030                1035

Lys Leu  Asn Ser Glu Leu Pro  Lys Glu Arg Gly Val  Gly Asp Ala
    1040                1045                1050

Ile Asn  Asn Gly Arg Asp His  Ser Ile Gln Ile Lys  Ile Gly Lys
    1055                1060                1065

Leu Gln  Lys Arg Met Trp Ile  Asn Val Asp Val Gln  Asn Thr Ile
    1070                1075                1080

Ile Asp  Gly Glu Val Phe Asp  Phe Ser Thr Tyr Tyr  Leu Gly Gly
    1085                1090                1095

Ile Pro  Ile Ala Ile Arg Glu  Arg Phe Asn Ile Ser  Thr Pro Ala
    1100                1105                1110

Phe Arg  Gly Cys Met Lys Asn  Leu Lys Lys Thr Ser  Gly Val Val
    1115                1120                1125

Arg Leu  Asn Asp Thr Val Gly  Val Thr Lys Lys Cys  Ser Glu Asp
    1130                1135                1140

Trp Lys  Leu Val Arg Ser Ala  Ser Phe Ser Arg Gly  Gly Gln Leu
    1145                1150                1155

Ser Phe  Thr Asp Leu Gly Leu  Pro Pro Thr Asp His  Leu Gln Ala
    1160                1165                1170

Ser Phe  Gly Phe Gln Thr Phe  Gln Pro Ser Gly Ile  Leu Leu Asp
    1175                1180                1185

His Gln  Thr Trp Thr Arg Asn  Leu Gln Val Thr Leu  Glu Asp Gly
    1190                1195                1200

Tyr Ile  Glu Leu Ser Thr Ser  Asp Ser Gly Gly Pro  Ile Phe Lys
    1205                1210                1215

Ser Pro  Gln Thr Tyr Met Asp  Gly Leu Leu His Tyr  Val Ser Val
    1220                1225                1230

Ile Ser  Asp Asn Ser Gly Leu  Arg Leu Leu Ile Asp  Asp Gln Leu
    1235                1240                1245

Leu Arg  Asn Ser Lys Arg Leu  Lys His Ile Ser Ser  Phe Arg Gln
    1250                1255                1260
```

-continued

```
Ser Leu  Arg Leu Gly Gly Ser  Asn Phe Glu Gly Cys  Ile Ser Asn
    1265                 1270                 1275

Val Phe  Val Gln Arg Leu Ser  Leu Ser Pro Glu Val  Leu Asp Leu
    1280                 1285                 1290

Thr Ser  Asn Ser Leu Lys Arg  Asp Val Ser Leu Gly  Gly Cys Ser
    1295                 1300                 1305

Leu Asn  Lys Pro Pro Phe Leu  Met Leu Leu Lys Gly  Ser Thr Arg
    1310                 1315                 1320

Phe Asn  Lys Thr Lys Thr Phe  Arg Ile Asn Gln Leu  Leu Gln
    1325                 1330                 1335
```

TECHNIQUE FOR CULTURE OF MESENCHYMAL STEM CELL UTILIZING LAMININ-5

This is a submission under 35 U.S.C. 371 of Application No. PCT/JP2006/316545, filed Aug. 17, 2006, which is incorporated herein by reference. The PCT application claims priority to a Japanese application, JP 2005-240814, filed on Aug. 23, 2005.

TECHNICAL FIELD

The present invention relates to a technique for growing mesenchymal stem cells using laminin-5.

BACKGROUND ART

Mesenchymal stem cells in the bone marrow have the ability to differentiate into various cells such as osteocytes, chondrocytes, adipocytes and myocytes, and their application to regenerative medicine for bone injury, osteoarthritis, osteoporosis, myopathy, etc. is expected. Further, it has been also revealed that mesenchymal stem cells are effective for preventing the adverse effect of bone marrow transplantation (graft-versus-host disease). Thus, like hematopoietic stem cells, mesenchymal stem cells are most close to application; a part of them has been already applied to clinical medicine (Non-Patent Document 1).

Under circumstances, development of techniques for preparing and growing mesenchymal stem cells has been attempted (Patent Documents 1 and 2)

To date, FGF-2 (Non-Patent Document 2), HB-EGF (Non-Patent Document 3) and CYR61/CCN1 (Non-Patent Document 4) have been found as growth factors for mesenchymal stem cells, but other effective factors have not been known.

[Patent Document 1] Japanese Unexamined Patent Publication No. 2004-089095

[Patent Document 2] Japanese Unexamined Patent Publication No. 2004-242619

[Non-Patent Document 1] Nikkei Biotechnology & Business, Nikkei Business Publications, Inc., July 2004 issue, pp. 16-17

[Non-Patent Document 2] Biochemical and Biophysical Research Communications 288, 413-419 (2001)

[Non-Patent Document 3] Blood 106, 59-66 (2005)

[Non-Patent Document 4] Protein Expression & Purification 42, 219-225 (2005)

DISCLOSURE OF THE INVENTION

Problem for Solution by the Invention

It is an object of the present invention to provide a technique for efficiently growing mesenchymal stem cells.

Means to Solve the Problem

The present inventors have found that it is possible to promote the growth of mesenchymal stem cells while retaining their differentiation ability, by using laminin-5 which is a basement membrane-type cell adhesion molecule. Thus, the present invention has been achieved.

The summary of the present invention is as follows.

(1) An agent for improving at least one activity selected from the group consisting of the growth activity, adhesion activity and extension activity of mesenchymal stem cells, the agent comprising laminin-5 as an active ingredient.

(2) A method of culturing mesenchymal stem cells in the presence of laminin-5.

(3) The method of (2) above, wherein the cells are cultured in a serum-free medium.

(4) The method of (3) above, wherein the medium contains a fibroblast growth factor.

(5) A method of isolating mesenchymal stem cells, comprising culturing the cells by the method of any one of (2) to (4) above.

(6) A medium for use in culturing mesenchymal stem cells, the medium containing laminin-5 at a concentration of 0.01 μg/ml or more.

(7) The medium of (6) above, which is a serum-free medium.

(8) The medium of (7) above, which further contains a fibroblast growth factor.

(9) A vessel or sheet for use in culturing mesenchymal stem cells, wherein laminin-5 has been coated or immobilized on the vessel or sheet at a concentration of 5 $ng/cm^2$ or more by treating the vessel or sheet with a laminin-5 solution of a concentration of 0.05 μg/ml or more or allowing laminin-5-producing cells to be deposited on the vessel or sheet.

Effect of the Invention

According to the present invention, it has become possible to grow mesenchymal stem cells efficiently.

The present specification encompasses the contents of the specification and/or the drawings of Japanese Patent Application No. 2005-240814 based on which the present patent application claims priority.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

BEST MODE FOR CARRYING OUT THE INVENTION

Hereinbelow, embodiments of the present invention will be described in detail.

The present invention provides an agent for improving at least one activity selected from the group consisting of the growth activity, adhesion activity and extension activity of mesenchymal stem cells, which comprises laminin-5 as an active ingredient.

Mesenchymal stem cells are present, for example, in the bone marrow of mammals and have the ability to differentiate various types of cells. It is known that mesenchymal stem cells differentiate not only to osteocytes, chondrocytes and adipocytes but also to cardiomyocytes and neuronal cells. The source of mesenchymal stem cells is not particularly limited. Mesenchymal stem cells derived from mammals (such as human, pig, monkey, chimpanzee, dog, cattle, rabbit, rat, mouse, etc.), birds or reptiles may be enumerated. For use in regenerative medicine, human-derived m esenchymal stem cells are preferred. Mesenchymal stem cells may be collected from the bone marrow or periosteum by known methods. Alternatively, mesenchymal stem cells may be collected from the thigh bone, neck bone or pelvis (ilium). Human mesenchymal stem cells are also commercially available (PT-2501; Cambrex).

Figure 1:
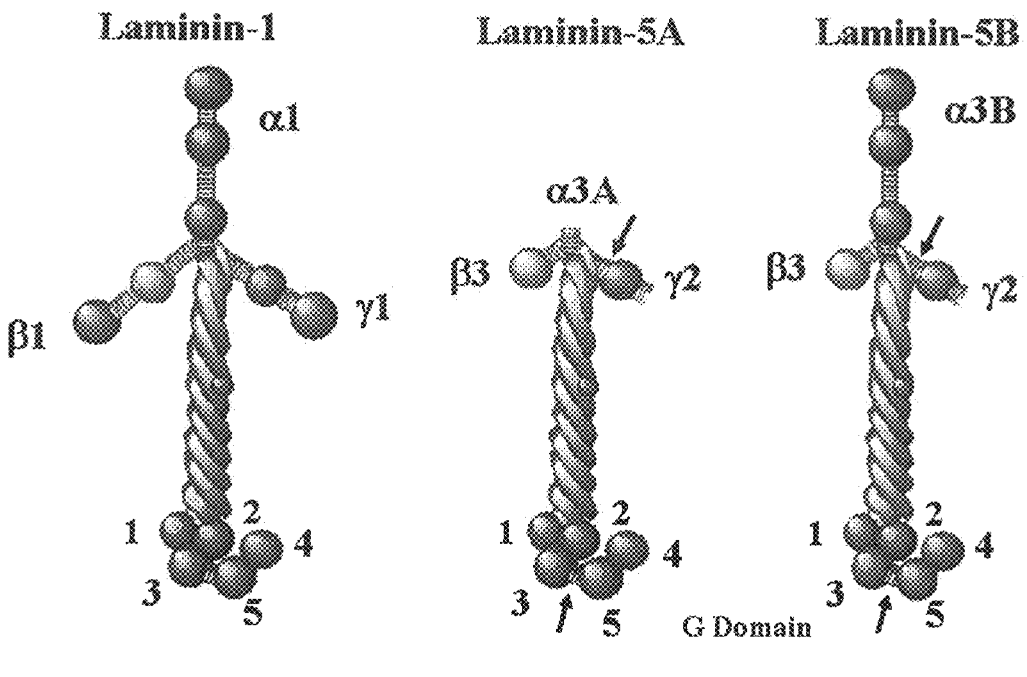
FIG. 1 shows the basic structures of laminin molecules.

Laminin are an important component of the basement membrane and are regulating cellular functions by interacting with cell surface receptors. Each laminin molecule is a heterotrimer protein assembled from α, β and γ chains associated by disulfide bonds, and has a characteristic cross structure. To date, 15 isoforms of laminin have been identified which are assembled from different combinations of 5 forms of α chain, 3 forms of β chain and 3 forms of γ chain (FIG. 1). Individual isoforms show different tissue distributions and are believed to play different roles. However, the details thereof are not elucidated yet.

Laminin molecules construct the basement membrane by associating with each other at the amino (N) terminal portion (short arm) of the triple strand or associating with other matrix molecules. On the other hand, 5 homologous globular domains (G1-G5 domains or LG1-LG5) are present at the carboxyl (C) terminal of α chain; laminin molecules bind to integrin and other receptors mainly at this site.

Figure 2:
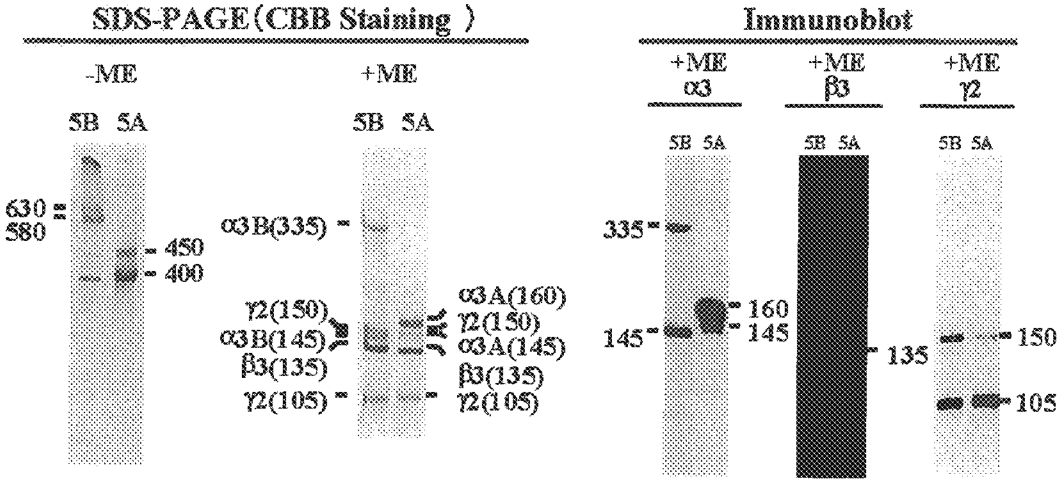
FIG. 2 shows the electrophoresis patterns of purified laminin-5A and laminin-5B. Left Panel: laminin-5A and laminin-5B purified from the culture supernatants of LN5A-HEK cells and LN5B-HEK cells, respectively, were separated by SDS-PAGE on 4.0-7.5% gradient gel under non-reducing conditions (−ME) or reducing conditions (+ME) and then stained with a dye (CBB). The two lanes on the left show the trimers of individual laminin-5 molecules and the molecular sizes thereof. The two lanes on the right show the individual subunits (chains) and the molecular sizes (kDa) thereof. Right Panel: the α3 chain, β3 chain and γ2 chain of purified laminin-5A and laminin-5B were analyzed by immunoblotting. The individual subunits and the molecular sizes thereof are indicated. α3A/3B chains of 145 kDa and γ2 chain of 105 kDa are chains generated by protease cleavage.

Laminin-5 is a laminin molecule composed of α3 chain, β3 chain and γ2 chain and was found as an extracellular matrix molecule expressed by epidermal cells and cancer cells (also called ladsin, kalinin, epiligrin or nicein). This molecule plays a central role in the binding of the epiderm to the derm, and binds preferentially to integrin α3β1 in most cells. However, depending on cells, this molecule also binds to integrin α6β1 or α6β4. It has been elucidated that the α3G2A sequence of α3 chain G2 domain (RERFNISTPAFRGCMKNLKKTS) and KRD sequence in the G3 domain in laminin-5 are major binding sites for integrin. It is also known that G4 and G5 domains located at the C-terminal of α3 chain are cleaved and removed by protease immediately after secretion of laminin-5 (FIG. 1). Laminin-5 isolated by conventional methods does not have G4 and G5 domains. It is known that such an α3 chain-truncated type laminin-5 has higher cell adhesion promotive activity, cell movement promotive activity and neurite extension promotive activity than non-truncated type laminin-5 (J. Biol. Chem., 280 (2005), 14370-14377). Further, γ2 chain (150 kDa) is cleaved at the short arm to yield a chain of 105 kDa (FIG. 1). The degree of cleavage varies depending on cell. In Examples described later, most of the γ2 chains used therein were truncated (FIG. 2). It is known that cleavage of γ2 chain decreases the cell adhesion promotive activity of laminin-5 and increases the movement promotive activity of laminin-5 (J. Cell. Biochem., 92 (2004), 701-704). Although β3 chain is difficult to be cleaved, it can be cleaved at the short arm in epidermal cells or the like (J. Biochem., 138 (2005), 539-552). The β3 chains used in Examples described later are not cleaved (FIG. 2, 135 kDa).

There are two types of α3 chain contained in laminin-5: short chain (α3A) and long chain (α3B). These two types have different expression patterns in various tissues (J. Biol. Chem., 270 (1995), 21820-21826). α3A chain has a structure in which the N-terminal portion of α3B chain is deleted (FIG. 1). Recently, the full-length cDNA of human α3B chain has been cloned, and the nature of a novel laminin-5 consisting of this α3B chain, β3 chain and γ2 chain has been elucidated (J. Biol. Chem., 279 (2004), 24774-24784). The laming-5 protein containing the short α3 chain (α3A) is called laminin-5 (or laminin-5A), and the laminin-5 protein containing the long α3 chain (α3B) is called laminin-5B (FIG. 1). α3A chain has the amino acid sequence as shown in SEQ ID NO: 10 which may have deletion, addition or substitution of one or more amino acid residues. α3B chain has the amino acid sequence as shown in SEQ ID NO: 2 which may have deletion, addition or substitution of one or more amino acid residues. β3 chain has the amino acid sequence as shown in SEQ ID NO: 4 which may have deletion, addition or substitution of one or more amino acid residues. γ2 chain has the amino acid sequence as shown in SEQ ID NO: 6 which may have deletion, addition or substitution of one or more amino acid residues.

The laminin-5 used in the present invention may be a laminin-5 protein whose G4 and G5 domains have been cleaved by protease immediately after secretion. In the present specification the α3A chain from which G4 and G5 domains have been cleaved is designated α3A#3 chain; and the α3B chain from which G4 and G5 domains have been cleaved is designated α3B#3 chain. The laminin-5 used in the present invention may be laminin-5A protein composed of three subunits of α3A#3 chain, β3 chain and γ2 chain; or laminin-5B protein composed of three subunits of α3B#3 chain, β3 chain and γ2 chain. α3A#3 chain has the amino acid sequence as shown in SEQ ID NO: 12 which may have deletion, addition or substitution of one or more amino acid residues. α3B#3 chain has the amino acid sequence as show in SEQ ID NO: 18 which may have deletion, addition or substitution of one or more amino acid residues. β3 chain has the amino acid sequence as shown in SEQ ID NO: 4 which may have deletion, addition or substitution of one or more amino acid residues. γ2 chain has the amino acid sequence as shown in SEQ ID NO: 6 which may have deletion, addition or substitution of one or more amino acid residues.

FIG. 1 shows the structures of laminin-5A (LN5A) protein and laminin-5B (LN5B) protein Laminin-5A is composed of α3A chain, β3 chain and γ2 chain; and laminin-5B is composed of α3B chain, β3 chain and γ2 chain. α3B chain is about two times as big as α3A chain in size; the structure of the one half of α3B chain on the C-terminal side is common with the structure of α3A chain. Both α3A chain and α3B chain have a globular (G) domain at their C-terminals. The G domain is divided into 5 sub-domains (or modules) (G1-G5). When laminin-5A or -5B is secreted from cells, most of the molecules are immediately cleaved between G3 and G4 by an endogenous protease. Therefore, G4 and G5-deleted laminin-5A or -5B is secreted into the culture medium. Further, partial cleavage also occurs at the N-terminals of α3B chain, α3A chain and γ2 chain.

The laminin-5 (including laminin-5A and laminin-5B) protein used in the present invention may be a culture supernatant of an animal or human cell secreting these laminin-5 proteins, or a natural type laminin-5 purified therefrom. However, these laminin-5 proteins may be produced as recombinant proteins efficiently and in large quantities by expressing individual subunits with recombinant DNA techniques known in the art.

The cDNAs encoding the individual subunits of laminin-5A may be prepared by designing primers based on the nucleotide sequences shown in SEQ ID NOS; 9, 3 and 5 and amplifying the sequences of interest by polymerase chain reaction PCR) using an appropriate cDNA library as a template. In the same manner, the cDNAs encoding the individual subunits of laminin-5B may be prepared by designing primers based on the nucleotide sequences shown in SEQ ID NOS: 1, 3 and 5 and amplifying the sequences of interest by polymerase chain reaction (PCR) using an appropriate cDNA library as a template. Such PCR technique is well-known in the art and described, for example, in "PCR Protocols, A Guide to Methods and Applications", Academic Press, Michael, et al., eds., 1990.

DNAs encoding the genes of individual chains of laminin-5A or -5B are incorporated into an appropriate vector(s). The resultant vector(s) is/are introduced into a eukaryotic or prokaryotic cell to thereby allow the expression of individual chains. Thus, a protein of interest may be obtained. Examples of host cells which may be used for expressing the protein of the present invention include, but are not limited to, prokaryotic host cells such as *Escherichia coli* and *Bacillus subtilis*, and eukaryotic host cells such as yeast, fungi, insect cells and mammal cells. Examples of mammal cells useful as hosts include HeLa cells, fibroblast-derived cells (e.g., VERO or CHO-K1), lymphocyte-derived cells, and derivatives thereof. Examples of preferable mammalian host cells include SP2/0 and J558L, as well as neuroblastoma cell strains such as 32. Further, plant cells and insect cells (such as *Drosophila* cells) may also be used as hosts.

The term "vector" refers to a single-stranded or double-stranded nucleic acid molecule which is capable of transfection into cells and capable of replicating in the cell genome or replicating independently. The expression vector comprises a promoter region which drives the expression of a DNA of interest, and may further comprise regulatory sequences for transcription and translation (e.g., TATA box, capping sequence, CAAT sequence, 3' non-coding region, enhancer, or the like). Examples of promoters include bla promoter, cat promoter and lacZ promoter when used in a prokaryotic host; the promoter of mouse metallothionein I gene sequence, herpes virus TK promoter, SV40 early promoter, yeast glycolytic enzyme gene sequence promoter or the like when used in a eukaryotic host. Examples of vectors include, but are not limited to, pBR322, pUC118, pUC119, λgt10, λgt11, pMAM-neo, pKRC, BPV, vaccinia, SV40 and 2-micron.

The expression vector preferably comprises one or more markers so that host cells containing the vector may be selected easily. As the marker, those which render nutrition to auxotrophic hosts, or which render resistance to antibiotics (e.g., ampicillin, tetracycline, neomycin, hygromycin, or the like) or resistance to heavy metals (e.g., copper) may be used.

Further, using signal sequences, the vector may be constructed so that the protein of the present invention is secretorily expressed or the protein of the present invention is expressed in the form of a fusion protein with other protein. By using a fusion protein, the stability of the protein of interest may be improved or the purification thereof may be facilitated. The construction of such expression vectors is well-known in the art.

DNAs encoding the individual chains of laminin-5A or -5B may be incorporated into one expression vector. Alternatively, the DNAs may be incorporated into separate expression vectors, which then may be infected into the same cell. Since each of the sub-units α3 chain, β3 chain and γ2 chain is a very large polypeptide, the latter method may be used preferably.

The vector constructed so that laminin-5A or -5B is expressed may be introduced into an appropriate host cell by methods such as transformation, transfection, conjugation, protoplast fusion, electroporation, the particle gun technique, calcium phosphate precipitation or direct microinjection. Cells containing the vector are grown in an appropriate medium to thereby allow production of the protein of the present invention. The recombinant protein of interest is recovered from the cells or the medium and purified to thereby obtain laminin-5A or -5B protein. Purification may be performed using such methods as size exclusion chromatography, HPLC, ion exchange chromatography and immunoaffinity chromatography.

The method of producing laminin-5A is described in J. Biochem. 132 (2002), 607-612.

The method of producing laminin-5B is described in WO 00/66731 and Kariya, Y. et al., J. Biol. Chem., 279 (2004) 24774-24784.

The individual chains of laminin-5A or -5B may have the amino acid sequence as shown in the corresponding SEQ ID NO indicated above which has deletion, addition or substitution of one or more amino acid residues. Such a protein homologous to the corresponding natural protein may also be used in the present invention.

It is well-known in the art that a protein or polypeptide retaining its initial function may be obtained through conservative substitution of amino acids. Such substitution includes replacement of an amino acid with a residue having a similar physicochemical property, e.g., replacement of an aliphatic residue (Ile, Val, Leu or Ala) with other aliphatic residue; or replacement between basic residues Lys and Arg, between acidic residues Glu and Asp, between amido residues Gln and Asn, between hydroxyl residues Ser and Tyr, or between aromatic residues Phe and Tyr.

The laminin-5 protein used in the present invention may be a protein which has an amino acid sequence having at least 50%, 60%, 75%, 80%, 85%, 90%, 95%, 98% or 99% identity with the amino acid sequence as shown in SEQ ID NO: 2, 4, 6 or 8, and is capable of promoting at least one activity selected from the group consisting of the growth activity, adhesion activity and extension activity of mesenchymal stem cells. Sequence identity is calculated by dividing the number of identical residues by the total number of residues in the known sequence or in a domain of the known sequence and multiplying by 100. Several computer programs for determining sequence identity using standard parameters are available, e.g., Gapped BLAST or PSI-BLAST (Altschul, et al. (1997) Nucleic Acids Res. 25:3389-3402), BLAST (Altschul, et al. (1990) J. Mol. Biol. 215:403-410) and Smith-Waterman (Smith, et al. (1981) J. Mol. Biol. 147:195-197). Preferably, the default settings of these programs are used. However, these settings may be altered, if desired.

Laminin-5A or -5B protein from which a part of the component chains has been deleted may also be used. For example, α3A chain of laminin-5A and α3B chain of laminin-5B are cleaved by protease and lose G4 and G5. However, as long as the resultant protein retains the activity as laminin-5A or -5B, the protein may be used in the present invention regardless of being truncated or not.

Further, a protein which is derived from an organism species other than human and has an activity similar to that of human laminin-5A or -5B may also be used. Genes encoding such a protein may be easily isolated by techniques such as hybridization or PCR, using a polynucleotide (or fragments thereof) having the sequence as shown in SEQ ID NO: 1 (in the case of a protein with an activity similar to that of laminin-5B) or SEQ ID NO: 9 (in the case of a protein with an activity similar to that of laminin-5A), SEQ ID NO: 3, SEQ ID NO: 5 or SEQ ID NO: 7 as a probe or primers. The thus obtained homologous gene has at least 50% or more, preferably 60% or more, more preferably 70% or more, still more preferably 80% or more, particularly preferably 90% or more, most preferably 95% or more homology to the nucleotide sequence as shown in SEQ ID NO: 1 or 9, or SEQ ID NO: 3, 5 or 7; or the homologous gene is capable of hybridizing under stringent hybridization conditions to a gene having the nucleotide sequence as shown in SEQ ID NO: 1 or 9, or SEQ ID NO: 3, 5 or 7.

The term "hybridize" means that a DNA or an RNA corresponding thereto binds to other DNA or RNA molecule by hydrogen bond interaction in a solution or on a solid support. The intensity of such interaction may be evaluated by changing the stringency in hybridization conditions. Hybridization conditions of various degrees of stringency may be used depending on desired specificity and selectivity. The stringency may be adjusted by changing the concentrations of salts or denaturing agents. Such methods of adjusting stringency are well-known in the art and described, for example, in "Molecular Cloning: A Laboratory Manual", 2nd Ed., Cold Spring Harbor Laboratory, Sambrook, Fritsch & Maniatis, eds., 1989.

The term "stringent hybridization conditions" means in the presence of 50% formamide and in 700 mM NaCl at 42° C., or conditions equivalent thereto. One example of stringent hybridization conditions is overnight hybridization in a solution containing 50% formamide, 5×SSC, 50 mM $NaH_2PO_4$, pH 6.8, 0.5% SDS, 0.1 mg/ml sonicated salmon sperm DNA and 5× Denhardt's solution at 42° C.; washing with a solution containing 2×SSC and 0.1% SDS at 45° C.; and washing with a solution containing 0.2×SSC and 0.1% SDS at 45° C.

Laminin-5 is capable of promoting at least one activity selected from the group consisting of the growth activity, adhesion activity and extension activity of mesenchymal stem cells. The cell growth promotive activity of laminin-5 may be assayed by adding laminin-5 to a culture medium for culturing cells and determining the cell growth rate relative to the control (laminin-5 not added). When the cell growth rate is larger than that of the control, it is possible to judge that laminin-5 promotes cell growth activity. The cell adhesion promotive activity of laminin-5 may be assayed by coating a plate with laminin-5, seeding cells in this plate, incubating the plate for a specific period of time, and counting the number of cells adhering thereto. When the number of cells adhering to the plate is larger than that in the control (laminin-5 not added), it is possible to judge that laminin-5 promotes cell adhesion activity. The cell spreading promotive activity of laminin-5 may be assayed by coating a plate with laminin-5, seeding cells in this plate, incubating the plate for a specific period of time, and observing the shapes of cells adhering thereto. When cells are flattened, it is possible to judge that laminin-5 promotes cell spreading activity.

In order to promote at least one activity selected from the group consisting of the growth activity, adhesion activity and extension activity of mesenchymal stem cells using laminin-5, laminin-5 may be added to the culture medium of mesenchymal stem cells, or coated or immobilized on a culture vessel (such as culture plate) or a culture sheet. Laminin-5 to be added to the culture medium may be either a recombinant protein or a natural protein, and may be either purified or unpurified. It is also possible to use a culture supernatant (conditioned medium) of laminin-5-secreting cells as a laminin-5 solution. Immobilization of laminin-5 may be performed by applying a solution containing one of these laminin-5 proteins directly to a culture vessel or culture sheet. Alternatively, a culture vessel or culture sheet on which laminin-5-producing cells are deposited (laminin-5 matrix) may be used. For most animal cells, adhesion to a matrix (scaffold) is essential for their survival. Further, they divide upon receipt of stimuli from growth factors. As seen from the result of Example 2 described later, normal cells are generally low in growth rate. Since laminin-5 has both cell adhesion activity and growth promotive activity as a growth factor, it is effective as a growth promotive agent for mesenchymal stem cells. Therefore, laminin-5 may be used in culturing mesenchymal stem cells.

When laminin-5 is added to a culture medium, the concentration of laminin-5 in the culture medium is not particularly limited. Usually, concentrations of 0.01 μg/ml or more may be appropriate. Optimal growth effect is obtained at concentrations of 0.1-1 μg/ml. Other components in the culture medium are not particularly limited as long as they are suitable for culturing mesenchymal stem cells. Immobilized laminin-5 may also be prepared by culturing laminin-5-producing cells (e.g., LN5-HEK cells, LN5B-HEK cells, epidermal cells, squamous carcinoma cells, gastric cancer cells and the like) in an appropriate culture vessel or on a culture sheet at a saturated state for more than several hours (preferably, 2 days or more) and then removing the cells by EDTA treatment or the like. As a culture medium, a basal medium such as Dulbecco's modified Eagle medium (DMEM) or DMEM/F12 may be used. Further, glucose, fetal calf serum (FCS), human serum, horse serum, antibiotics (e.g., penicillin, streptomycin) and growth factors (e.g., FGF-2, HB-EGF, CYR61/CCN1) may also be added to the medium.

By using laminin-5, it is possible to grow mesenchymal stem cells in a serum-containing or serum-free medium, When mesenchymal stem cells are seeded in a laminin-5-added growth medium at a density of 5,000-6,000 cells/$cm^2$ and cultured at 37° C. under 5% $CO_2$, the cells usually reach saturation in 5-6 days.

Generally, cell culture methods are classified into monolayer static culture, roller bottle culture, agitation culture, carrier culture and so on. In the present invention, any culture method may be used.

When mesenchymal stem cells are cultured in a culture vessel (such as culture plate) or on a culture sheet on each of which laminin-5 has been coated or immobilized, the amount of laminin-5 is not particularly limited. The amount may be appropriately adjusted depending on the size of the culture vessel or culture sheet. Usually, good growth is obtained when the culture vessel or sheet has been treated with a laminin-5 solution of a concentration of 0.05 μg/ml or more, preferably 0.5-3 μg/ml. Laminin-5 may be coated or immobilized on the culture vessel or sheet at a concentration of 5 ng/$cm^2$ or more, preferably at a concentration of 50-300 ng/$cm^2$. As a medium for culturing mesenchymal stem cells, a basal medium such as Dulbecco's modified Eagle medium (DMEM) or DMEM/F12 may be used. Further, glucose, fetal calf serum (FCS), human serum, horse serum, antibiotics (e.g., penicillin, streptomycin) and growth factors (e.g., FGF-2, HB-EGF, CYR61/CCN1) may also be added to the medium.

Using laminin-5 immobilized in any of the above-described methods, mesenchymal stem cells can be grown in a serum-containing or serum-free medium. When mesenchymal stem cells are seeded in a laminin-5-coated plate at a density of 5,000-6,000 cells/$cm^2$ and cultured at 37° C. under 5% $CO_2$, the cells usually reach saturation in 5-6 days.

Since laminin-5 allows effective adhesion of mesenchymal stem cells thereto, laminin-5 is applicable to isolation/preparation of mesenchymal stem cells from the bone marrow or the like. For example, a cell mire containing mesenchymal stem cells (such as bone marrow) is seeded on a laminin-5-coated (immobilized) culture vessel or culture sheet and incubated for 5 min to 2 hrs. After removal of unadhered cells, mesenchymal stem cells adhering to the plate are separated from other cells. Those mesenchymal stem cells grown on the plate may be recovered by conventional trypsin treatment.

EXAMPLES

Hereinbelow, the present invention will be described in more detail with reference to the following Examples. However, the present invention is not limited to these Examples.

Example 1

Preparation of Recombinant Human Laminin-5A and -5B

Laminin-5A was prepared according to the previously described method (Kariya, K. et al., J. Biochem., 132 (2002), 607-612). Briefly, a serum-free culture supernatant of a human embryonic kidney cell strain HEK293 (LN5-HEK) transfected with cDNAs encoding α3A chain, β3 chain and γ2 chain was recovered. Proteins contained therein were concentrated by ammonium sulfate precipitation and then fractionated by gel filtration using a Sepharose 4B (Amersham) column. Laminin-5A-containing fractions were applied to a gelatin column to remove fibronectin and then applied to an anti-laminin α3A chain monoclonal antibody (LSα3-immobilized affinity column to absorb laminin-5A, followed by elution. The purified laminin-5A was subjected to reducing SDS-PAGE on 6% gel and immunoblotting to thereby confirm that the resultant protein is almost pure (FIG. 2). The immunoblotting was performed using an α3A chain antibody (LSα3; prepared by the present inventors), a β3 chain antibody (Kalinin B31, Transduction Laboratories) and a γ2 chain antibody (D4B5; prepared by the present inventors). It should be noted that a purified sample almost equal to the above-described purified protein could be obtained when the culture supernatant was directly fractionated with the gelatin column and the antibody column. In the thus prepared and purified laminin-5A, α3 chain was completely cleaved to yield a 160 kDa chain; and γ2 chain became a 105 kDa truncated chain (cleaved between Asp(435) and Glu(436) in the amino acid sequence as shown in SEQ ID NO: 6) for the most part. The cleavage of α3A chain occurs between Gln (1337) and Asp(1338) located between G4 domain and G5 domain (Tsubota, Y et al., Biochem. Biophys. Res. Commun., 278 (2000), 614-620).

Preparation and purification of laminin-5B were performed in the same manner as described above using a culture supernatant recovered from a human embryonic kidney cell strain HEK293 (LN5B-HEK) transfected with cDNAs encoding encoding α3B chain, β3 chain and γ2 chain (Kariya, Y et al., J. Biol. Chem., 279 (2004), 24774-24784). In the purified laminin-5B, about one half of the γ2 chains were a truncated γ2 chain (FIG. 2). Since G4-G5 regions were pre-deleted from the α3B chain-encoding cDNA, the major component of the expressed α3B chain was a truncated 335 kDa protein (however, the C-terminal sequence of this α3B#3 was Phe2944 which is shorter than the C-terminal sequence Gln2957 generated by protease cleavage). A 145 kDa α3B chain further cleaved at the N-terminal was also observed. This cleavage occurs between Lys(1811) and Asp(1812) (Kariya, Y. et al., J. Biol. Chem., 279 (2004), 24774-24784).

The following Examples, the term "laminin-5" refers to the laminin-5A prepared in this Example unless otherwise stated.

Example 2

Assay of Growth Activity on Mesenchymal Stem Cells

Human mesenchymal stem cells (hMSC; Cambrex) were seeded in 24-well plates at a density of $5\times10^3$ cells/well and cultured in a maintenance medium (Cambrex) for 12 days. Briefly, cells were treated as described below. The number of cells was counted in every 4 days.

(A) The 24-well plates were coated with laminin-5 as follows. Zero point five milliliters of 1.0 μg/ml laminin-5 solution (diluted with physiological saline (PBS)) was added to each well (0.5 μg laminin-5/well) and left overnight at 4° C. After removal of the solution, 0.5 ml of 12 mg/ml bovine serum albumin (BSA) solution was added to each well and incubated at room temperature for 2 hours (BSA blocking). Each well was washed twice with PBS, and then cells were seeded therein. Control was treated with PBS. It should be noted here that BSA blocking is not necessarily required for practical use of laminin-5.

(B) Plates were coated with laminin-5 solutions with concentrations of 0.5, 1.0 and 2.0 μg/ml as described above (0.25, 0.5 and 1.0 μg/well, respectively).

(C) Cells were cultured on plates each well of which had been coated with 0.5 ml of 1.0 μg/ml laminin-5 solution as described above (0.5 μg/well) (Insoluble), or cultured on a medium to which laminin-5 had been added to give a concentration of 0.5 μg/ml (Soluble).

(D) Cells were cultured on plates coated with 1.0 μg/ml laminin-5 (LN5) (0.5 μg/well), or with 2.0 μg/ml (1.0 μg/well) laminin-1 (LN1; Chemicon), laminin-2/4 (LN2/4; Chemicon) or laminin-10/11 (LN10/11; Sigma-Aldrich).

(E) Plates were coated with 0.5 ml of 1.0 μg/ml laminin-5 solution or 1.5 μg/ml laminin-5B solution (0.5 μg/well or 0.75 μg/well), and cells were cultured thereon (Soluble).

Figure 3:
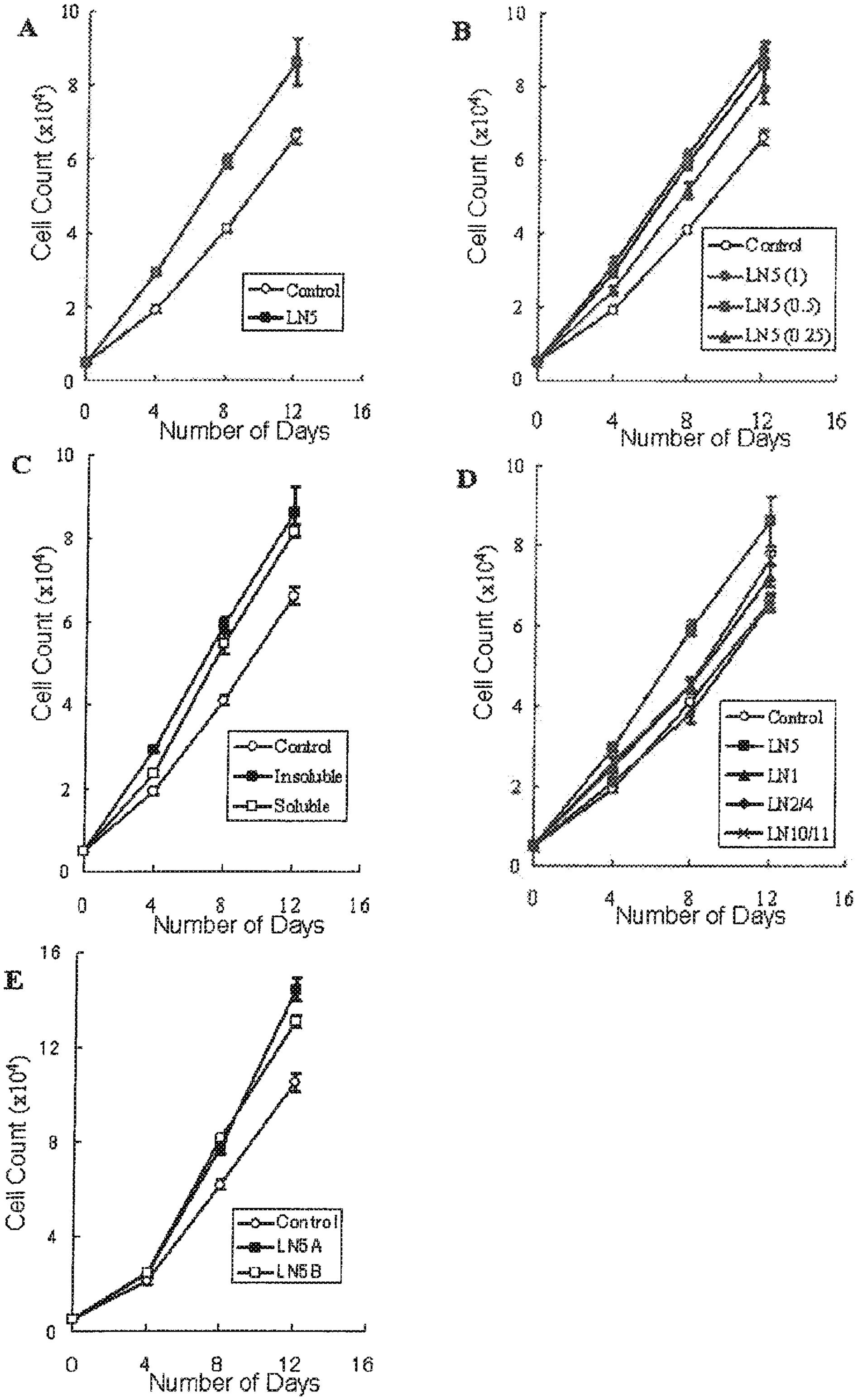
FIG. 3 shows the results of assay of growth activity on mesenchymal stem cells.

Throughout (A) to E) above, Control was treated with PBS alone instead of laminin solution. From FIG. 3A, it has become cleat that the growth rate of hMSC cells on laminin-5-coated plates was higher than that of Control. Further, from FIG. 3B, it was demonstrated that the effect was concentration dependent This growth promotive effect was also observed when laminin-5 was directly added to the medium (FIG. 3C). It was demonstrated that the growth promotive activity of laminin-5 was higher than other laminin proteins (FIG. 3D). When laminin-5B was used at the same molar concentrations as laminin-5 (laminin-5A), the two laminin proteins showed almost equivalent growth promotive activity (FIG. 3E).

Figure 4:
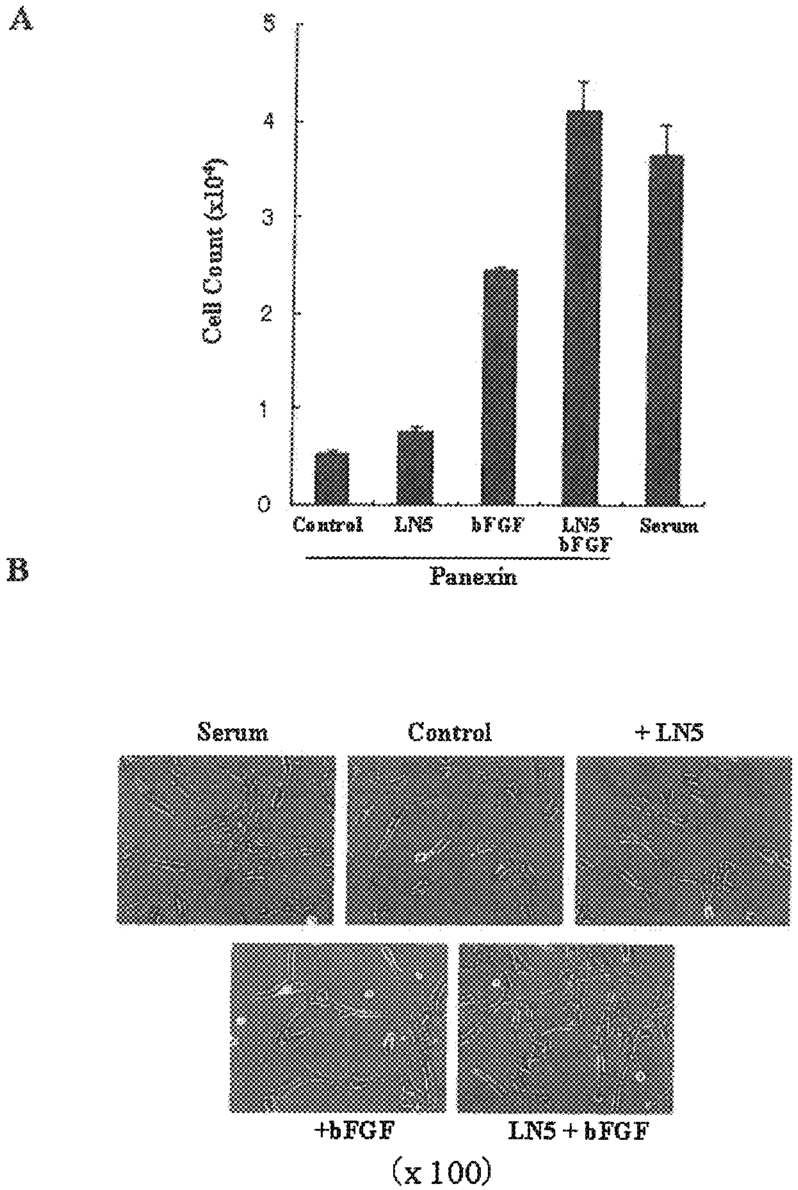
FIG. 4 shows the results of assay of growth activity on mesenchymal stem cells cultured in 5% panexin-containing, serum-free medium (panel A) and the morphology of the cells (panel B).

Subsequently, for elucidation of the growth promotive activity of laminin-5 in serum-free media, a medium was used to which a commercial serum-free additive for stem cells (Panexin; PAN-biotech) had been added. hMSC cells once washed with serum-free MSCBM medium (Cambrex) were suspended in 5% Panexin-containing, serum-free MSCBM medium, seeded on non-treated or laminin-5-coated (0.5 μg/ml) (LN5) plates and cultured for 8 days. For each plate, bFGF (basic fibroblast growth factor) (Wako Pure Chemical) was added to the medium to give a final concentration of 1 ng/ml, followed by examination of the effect thereof (FIGS. 4A and 4B). For the purpose of comparison, hMSC cells once washed with serum-free medium were seeded in 5% serum-containing maintenance medium (MSCBM+MSCGM) (Cambrex) in the same manner and cultured for 8 days (Serum). As a result, laminin-5 addition showed a certain growth promotion compared to serum-free MSCBM medium alone (Control), but the growth promotive activity of bFGF was more remarkable. In the presence of both laminin-5 and bFGF, cell growth was promoted synergistically, and growth promotion almost equivalent to that seen in serum-containing media was observed FIG. 4A). Morphologically, while cells became flat on laminin-5, a slightly thin and distinct cellular shape was obtained in the presence of both laminin-5 and bFGF (FIG. 4B). These results revealed that is possible to grow hMSC cells in serum-free media by a combined use of laminin-5 with bFGF and other growth factors.

Figure 5:
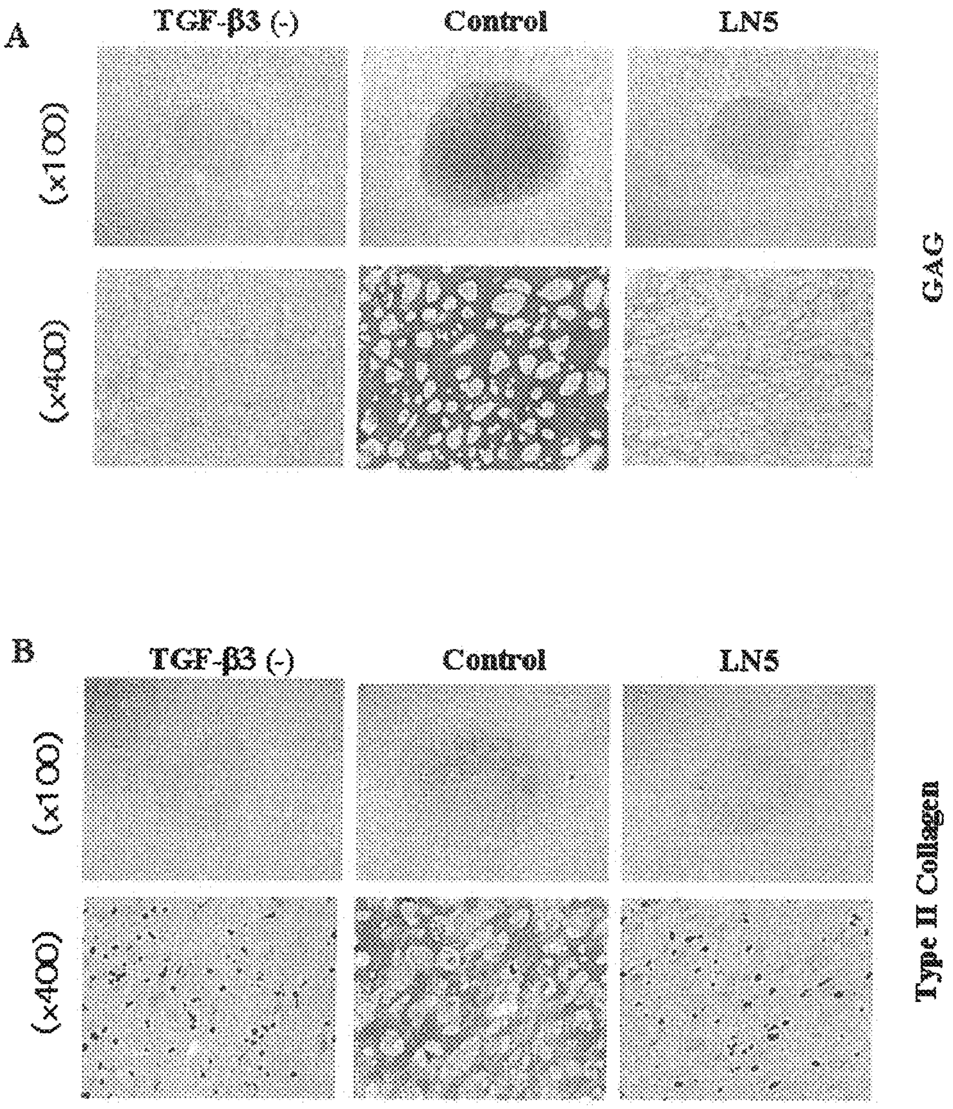
FIG. 5 shows the accumulation of glycosaminoglycan (GAG) (panel A) and the accumulation of type II collagen (panel B) when mesenchymal stem cells have been cultured for 3 weeks in a chondrocyte differentiation medium in the absence (Control) or presence (LN5) of laminin-5.

Further, the effect of laminin-5 on the differentiation of hMSC cells into chondrocytes and fibroblasts was examined. hMSC cells cultured in serum-containing maintenance medium (MSCBM+MSCGM) (Cambrex) were scraped off from the culture dish, washed with TGF-β3-not-added incomplete cartilage differentiation medium (dexamethasone, ascorbate, insulin, transferrin, sodium selenite, sodium pyruvate, proline, L-glutamine) (Cambrex) once, and then suspended in 10 ng/ml TGF-β3-added complete cartilage differentiation medium (Cambrex). Cells were transferred to polypropylene tubes at a concentration of $2.5\times10^5$ cells/tube and centrifuged. The resultant cell pellet was incubated at 37° C. for 24 hr or more to thereby allow formation of spherical cell masses. Laminin-5 (1 μg/ml) was added after the formation of cell masses, and cells were cultured. The medium was exchanged with laminin-5-added complete cartilage differentiation medium once in 2 or 3 days. After a three-week culture, sections were prepared from the cells. Cartilage-specific glycosaminoglycan was stained with Alcian blue, and type II collagen was stained with a specific antibody (Lab Vision). As a result, growth of cell masses was inhibited in laminin-5-added medium (LN5) compared to the growth in laminin-5-free complete cartilage differentiation medium (Control) (FIGS. 5A and 5B). Further, accumulations of glycosaminoglycan (FIG. 5A) and type II collagen (FIG. 5B) were inhibited remarkably by laminin-5; the degrees of staining were equivalent to those seen in TGF-β3-not-added incomplete cartilage differentiation medium (TGF-β3(−)). From these results, it was shown that laminin-5 inhibits the cartilage differentiation of hMSC cells.

Subsequently, the effect of laminin-5 on the fibroblast differentiation of hMSC cells was examined. Cells were dispersed in fibroblast differentiation medium (dexamethasone, ascorbate, β-glycerophosphate) (Cambrex), seeded on non-treated or laminin-5-coated (0.5 μg/ml) plates at a concentration of $3\times10^5$ cells/cm$^2$ and cultured for 3 weeks. Alkaline phosphatase, a fibroblast differentiation marker, was detected with a mixed solution of naphth ASBI and Fast Red TR (Sigma-Aldrich), and osteopontin, another fibroblast differentiation marker, was detected by immunoblotting using a specific antibody (IBL). As a result, it was demonstrated that laminin-5 does not affect the production of these proteins, i.e., does not affect the fibroblast differentiation of hMSC cells.

Figure 6:
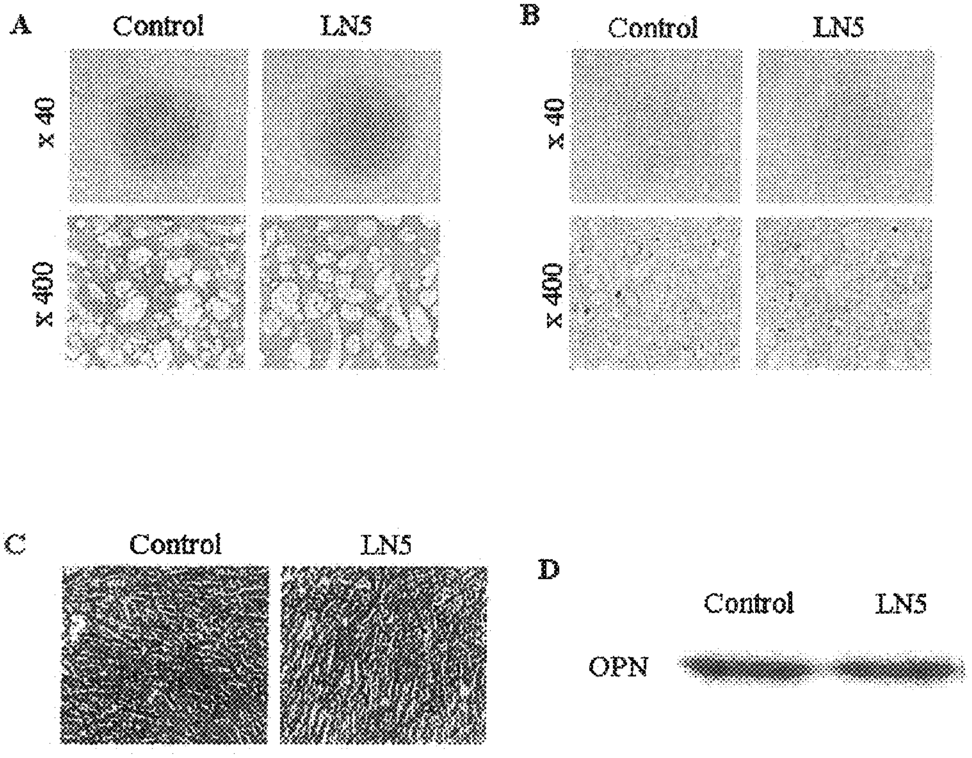
FIG. 6 shows the accumulation of glycosaminoglycan (GAG) (panel A) and the accumulation of type II collagen (panel B) when mesenchymal stem cells cultured for 8 days in the absence (Control) or presence (LN5) of laminin-5 have been cultured for 3 weeks in a chondrocyte differentiation medium. Further, the expression of alkaline phosphatase (panel C) and the expression of osteopontin (OPN; panel D) when each cell has been cultured for three weeks in an osteoblast differentiation medium are also shown.

Since laminin-5 inhibits chondrocyte differentiation, whether treatment with laminin-5 affects the differentiation ability of hMSC cells or not was examined. First, hMSC cells were cultured in a maintenance medium on non-treated (Control) or laminin-5 (1 μg/ml)-coated plates (LN5) for 8 days. Both cells were scraped off from the plates and examined on differentiation into chondrocytes and fibroblasts in the absence of laminin-5. When hMSC cells cultured in the absence (Control) or presence (LN5) of laminin-5 were cultured in complete cartilage differentiation medium (containing TGF-β3) for 3 weeks, no difference was observed between the two cells on accumulations of glycosaminoglycan (FIG. 6A) and type II collagen (FIG. 6B). When both cells were cultured in fibroblast differentiation medium for 3 weeks, no difference was observed between the two cells on expressions of alkaline phosphatase (FIG. 6C) and osteopontin (FIG. 6D; OPN). This means that treatment with laminin-5 did not affect the ability of hMSC cells to differentiate into chondrocytes and fibroblasts. From these results, it was demonstrated that laminin-5 promotes the cell growth of hMSC cells while retaining the differentiation ability thereof.

Example 3

Assay of Adhesion Activity on Mesenchymal Stem Cells 96-well plates were coated with 0.1 ml of 1.6 μg/ml laminin-1 (LN1), laminin-2/4 (LN2/4) or laminin-10/11 (LN10/11) solution (0.5 μg/cm$^2$) or 0.1 ml of 0.8 μg/ml laminin-5 (LN5) solution (0.25 μg/cm$^2$) and then blocked with 12 mg/ml BSA. To each well, hMSC cells washed twice with serum-free DMEM (Nissui) were seeded at a concentration of $2\times10^4$ cells/well. About 5 minutes later, non-adhering cells were floated by light vortexing and removed from the well surface by Percoll treatment. Cells adhering to the wells were fixed with formalin and stained with Hoechst 33432, followed by determination of the relative number of cells. A plate treated with PBS instead of laminin solution and blocked with BSA was used as control (None).

Figure 7A:
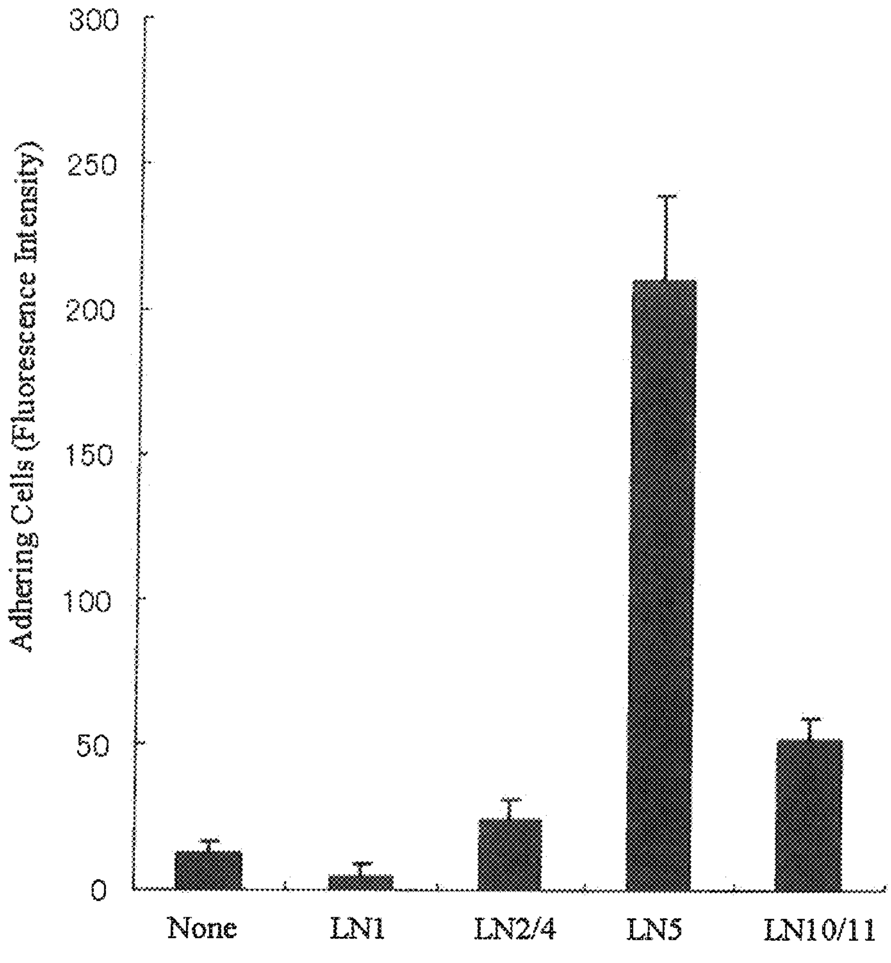
FIG. 7A shows the results of assay of adhesion activity on mesenchymal stem cells.

The results are shown in FIG. 7A. It has become clear that laminin-5 is remarkably high in adhesion activity, compared to other laminin proteins.

Example 4

Assay of Extension Activity on Mesenchymal Stem Cells hMSC cells were seeded at a concentration of $3\times10^3$ cells/cm$^2$ on plates coated with laminin solutions of the same concentrations as used in Example 3. After 10 minutes, cell morphology was observed. A plate treated with PBS instead of laminin solution was used as control (None).

Figure 7B:
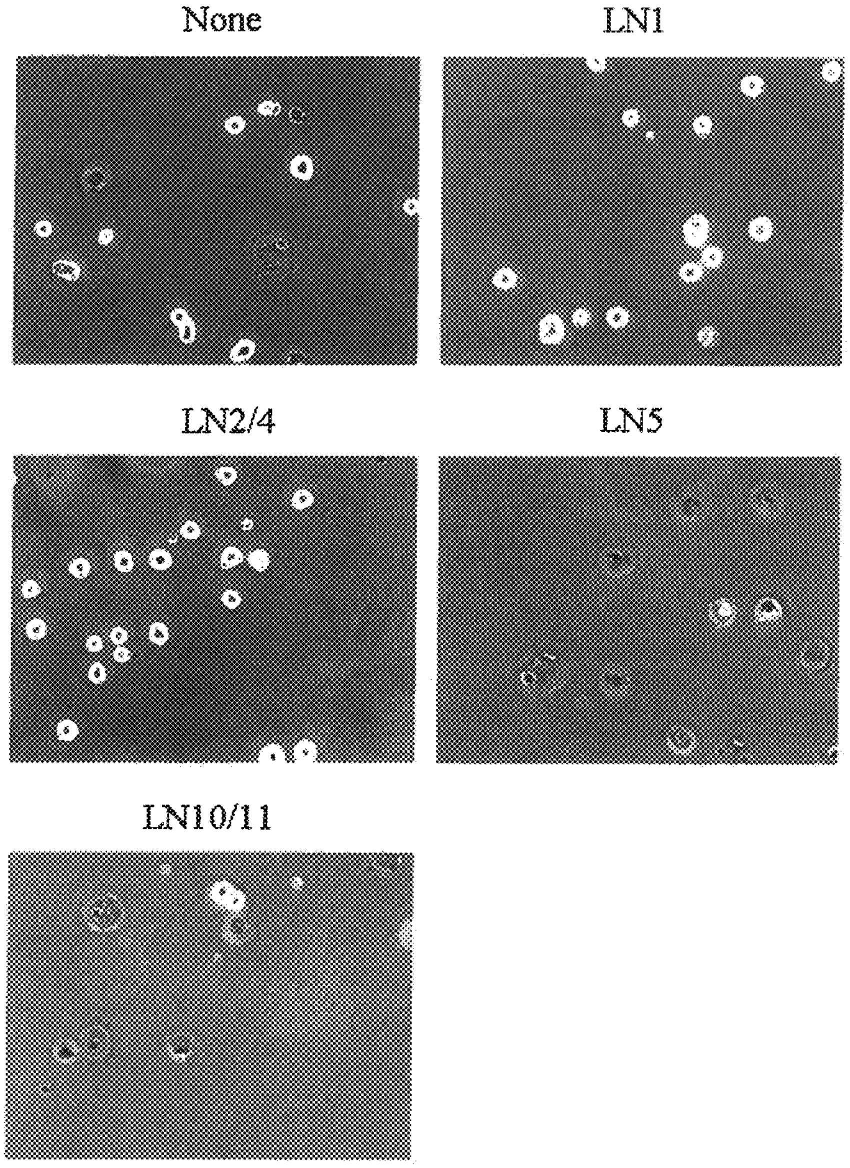
FIG. 7B shows the results of assay of extension activity on mesenchymal stem cells.

The results are shown in FIG. 7B. While most cells exhibit a spherical shape and no extension is observed in one, laminin-1 and laminin-2/4, most cells are spreading on plates and extension could be observed in laminin-5. Laminin-10/11 exhibited extension activity close to that of laminin-5.

Example 5

Influence of Anti-Integrin Inhibitory Antibody

Laminin-5 receptors of hMSC were examined using anti-integrin inhibitory antibodies, Before seeding cells on laminin-5 (LN5), hMSC was pre-incubated for about 5 minutes with anti-integrin inhibitory antibody (anti-α3 integrin antibody (P1B5)), anti-β1 integrin antibody (6S6), anti-β4 integrin antibody (3E1) (these three antibodies are produced by Chemicon) or anti-α6 integrin antibody (GoH3) (Pharmingen). Then, cell adhesion activity was determined in the same manner as in Example 3. A plate treated with PBS instead of laminin solution was used as control (None).

Figure 8:
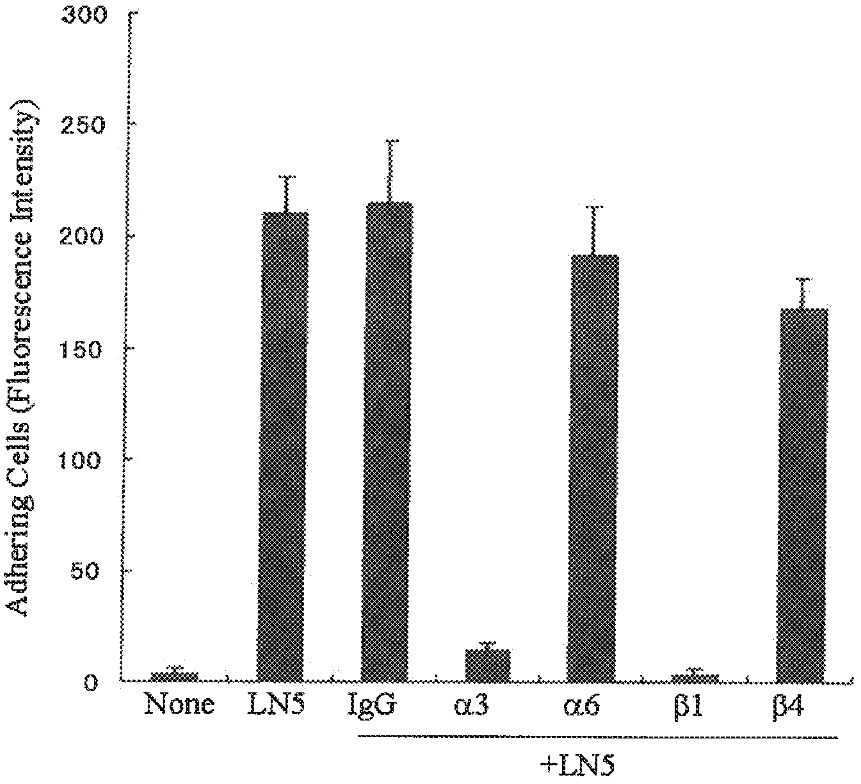
FIG. 8 shows the effect of anti-integrin inhibitory antibody upon assay of adhesion activity on mesenchymal stem cell.

The results are shown in FIG. 8. When treated with anti-α3 integrin antibody or anti-β1 integrin antibody, the adhesion promotive activity of laminin-5 as shown in FIG. 7A was remarkably inhibited. From these results, it has become clear that the cell adhesion promotive activity of laminin-5 is based on its binding to integrin α3β1.

All publications, patents and patent applications cited herein are incorporated herein by reference in their entirety.

INDUSTRIAL APPLICABILITY

By using laminin-5, it has become possible to culture mesenchymal stem cells efficiently. Mesenchymal stem cells have the ability to differentiate into various cells such as osteocytes, chondrocytes, adipocytes and myocytes. Application of mesenchymal stem cells to regenerative medicine for bone injury, osteoarthritis, osteoporosis, myopathy, etc. is expected.

Sequence Listing Free Text
<SEQ ID NO:1>
  SEQ ID NO: 1 shows the full-length nucleotide sequence of human laminin α3B chain.
<SEQ ID NO: >
  SEQ ID NO: 2 shows the full-length amino acid sequence of human laminin α3B chain.
<SEQ ID NO: 3>
  SEQ ID NO: 3 shows the full-length nucleotide sequence of human laminin β3 chain.
<SEQ ID NO: 4>
  SEQ ID NO: 4 shows the full-length amino acid sequence of human laminin β3 chain.
<SEQ ID NO: 5>
  SEQ ID NO: 5 shows the full-length nucleotide sequence of human laminin γ2 chain.
<SEQ ID NO: 6>
  SEQ ID NO: 6 shows the full-length amino acid sequence of human laminin γ2 chain.
<SEQ ID NO: 7>
  SEQ ID NO: 7 shows the nucleotide sequence of human laminin α3B#3 chain.
<SEQ ID NO: 8>
  SEQ ID NO: 8 shows the amino acid sequence of human laminin α3B#3 chain.
<SEQ ID NO: 9>
  SEQ ID NO: 9 shows the nucleotide sequence of human laminin α3A chain,
<SEQ ID NO: 10>
  SEQ ID NO: 10 shows the amino acid sequence of human laminin α3A chain.
<SEQ ID NO, 11>
  SEQ ID NO: 11 shows the nucleotide sequence of human laminin α3A#3 chain (human laminin α3A chain from which G3 and G4 have been cleaved out).
<SEQ ID NO: 12>
  SEQ ID NO: 12 shows the amino acid sequence of human laminin α3A#3 chain.

The invention claimed is:

1. A method of culturing mesenchymal stem cells, comprising:

providing laminin-5 at a concentration of 0.01 to 1 μg/ml to a culture medium containing mesenchymal stem cells and a serum substitute; and growing mesenchymal stem cells while retaining their differentiation ability.

2. A method of culturing mesenchymal stem cells, comprising:

providing laminin-5 at a concentration of 0.01 to 1 μg/ml to a culture medium containing mesenchymal stem cells, a fibroblast growth factor, and a serum substitute; and growing mesenchymal stem cells while retaining their differentiation ability in a serum-free medium.

3. A method of isolating mesenchymal stem cells, comprising culturing the cells by the method according to claim 1; and isolating the resultant mesenchymal stem cells from the medium.

4. The method according to claim 1, wherein the serum substitute is Panexin.

5. The method according to claim 1, wherein the medium further comprises a fibroblast growth factor.

6. A method of culturing mesenchymal stem cells, comprising:

applying laminin-5 at a concentration of 5 to 300 ng/cm$^2$ on a vessel or a sheet to coat or immobilize laminin-5 thereon;

applying a medium containing mesenchymal stem cells and a serum substitute to the vessel or the sheet; and growing the mesenchymal stem cells with laminin-5 as an active ingredient while retaining their differentiation ability.

7. The method of claim 6, wherein the serum substitute is Panexin.

8. The method of claim 6, wherein laminin-5 is immobilized by culturing laminin-5 producing cells in the vessels or the sheet to saturation, removing the cells, and culturing in a basal medium.

9. The method of claim 6, wherein laminin-5 (LN-5) is immobilized by culturing LN-5-HEK cells, LN5B-HEK cells, epidermal cells, squamous carcinoma cells, or gastric cancer cells in the vessel or the sheet to saturation, removing the cells with EDT A, and culturing the cells in Delbecco's Modified Eagle Medium (DMEM) or DMEM/F12.

10. The method of claim 1, wherein laminin-5 is either laminin-5A or laminin-5B, wherein laminin-5A has its a3A chain cleaved or laminin-5B has its α3B chain cleaved to lose sub-domains G4 and G5.

11. The method of claim 6, wherein laminin-5 is either laminin-5A or laminin-5B, wherein laminin-5A has its α3A chain cleaved or laminin-5B has its α3B chain cleaved to lose sub-domains G4 and G5.

12. The method according to claim 2, the serum substitute is Panexin.

13. The method according to claim 6, wherein the vessel or the sheet is coated or immobilized thereon with laminin-5 at a concentration of 50 to 300 ng/cm$^2$.

* * * * *